(12) United States Patent
Edinger et al.

(10) Patent No.: US 11,723,930 B2
(45) Date of Patent: Aug. 15, 2023

(54) TREATMENT OF INFLAMMATORY DISEASES USING PLACENTAL STEM CELLS

(71) Applicant: CELULARITY, INC., Warren, NJ (US)

(72) Inventors: James W. Edinger, Belford, NJ (US); Robert J. Hariri, Bernardsville, NJ (US); Jia-Lun Wang, Cherry Hill, NJ (US); Qian Ye, Livingston, NJ (US); Herbert Faleck, West Orange, NJ (US)

( * ) Notice: Subject to any disclaimer, the term of this patent is extended or adjusted under 35 U.S.C. 154(b) by 681 days.

(21) Appl. No.: 16/752,326

(22) Filed: Jan. 24, 2020

(65) Prior Publication Data

US 2020/0397830 A1 Dec. 24, 2020

Related U.S. Application Data

(63) Continuation of application No. 15/271,429, filed on Sep. 21, 2016, now abandoned, which is a continuation of application No. 14/550,524, filed on Nov. 21, 2014, now abandoned, which is a continuation of application No. 13/891,732, filed on May 10, 2013, now Pat. No. 8,916,146, which is a continuation of application No. 12/030,161, filed on Feb. 12, 2008, now Pat. No. 8,460,650.

(60) Provisional application No. 60/901,067, filed on Feb. 12, 2007.

(51) Int. Cl.
| | | |
|---|---|---|
| A61K 35/50 | (2015.01) | |
| A61K 45/06 | (2006.01) | |
| A61K 35/644 | (2015.01) | |
| A61K 38/21 | (2006.01) | |
| C12N 5/073 | (2010.01) | |
| A61K 35/12 | (2015.01) | |

(52) U.S. Cl.
CPC ............ *A61K 35/50* (2013.01); *A61K 35/644* (2013.01); *A61K 38/21* (2013.01); *A61K 45/06* (2013.01); *C12N 5/0605* (2013.01); *A61K 2035/122* (2013.01); *C12N 2500/25* (2013.01); *C12N 2500/36* (2013.01); *C12N 2501/11* (2013.01); *C12N 2501/135* (2013.01); *C12N 2501/39* (2013.01)

(58) Field of Classification Search
None
See application file for complete search history.

(56) References Cited

U.S. PATENT DOCUMENTS

2003/0180269 A1 * 9/2003 Hariri ..................... A61M 1/02
435/372

OTHER PUBLICATIONS

Braun-Moscovici et al., Current Opinion in Rheumatology 2002, 14:711-716 (Year: 2002).*
Tyndall et al., British Journal of Rheumatology 1997;36:390-392 (Year: 1997).*
Van Laar, Ann Rheum Dis 2005;64:1513-1515 (Year: 2005).*

* cited by examiner

*Primary Examiner* — James D Schultz
(74) *Attorney, Agent, or Firm* — Geoffry T. Knudsen

(57) ABSTRACT

Provided herein are methods of treatment of individuals having an immune-related disease, disorder or condition, for example, inflammatory bowel disease, graft-versus-host disease, multiple sclerosis, rheumatoid arthritis, psoriasis, lupus erythematosus, diabetes, mycosis fungoides (Alibert-Bazin syndrome), or scleroderma using placental stem cells or umbilical cord stem cells.

5 Claims, 28 Drawing Sheets

Figure 1:
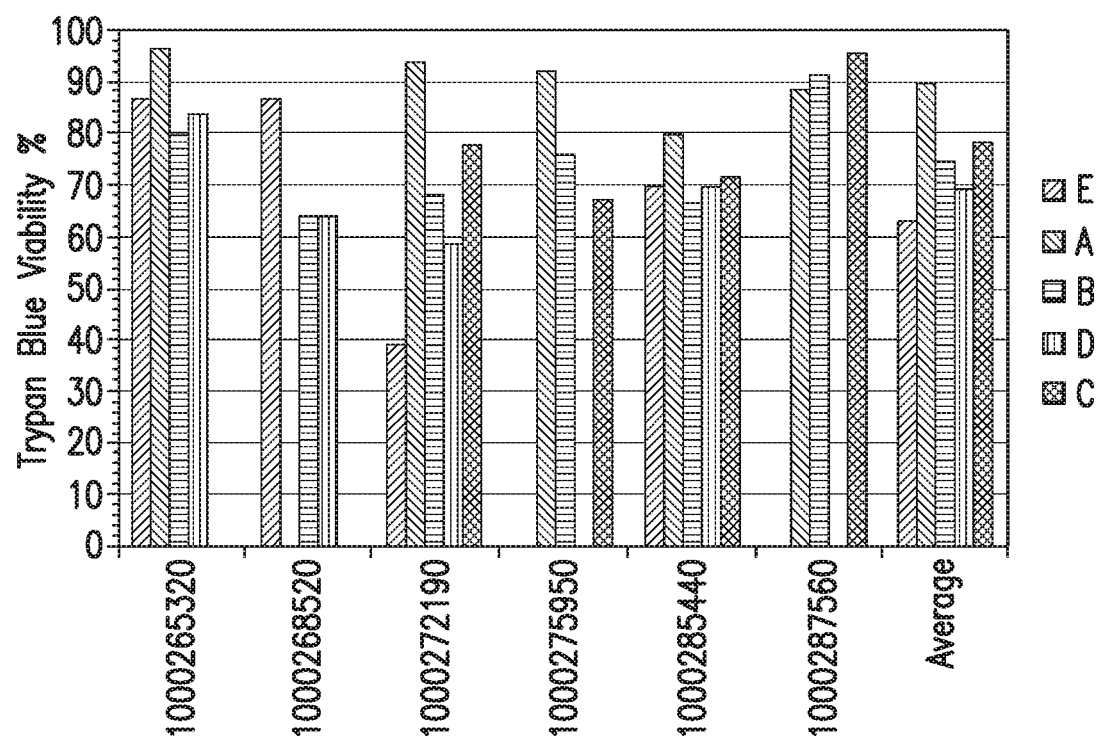

TREATMENT OF INFLAMMATORY DISEASES USING PLACENTAL STEM CELLS

This application claims benefit of U.S. Provisional Application No. 60/901,067, filed Feb. 12, 2007, which is incorporated herein in its entirety by reference.

1. FIELD

Provided herein are methods of using human placental stem cells to treat individuals having a disease, disorder or condition caused by, or relating to, an unwanted or harmful immune response, for example, inflammatory bowel disease, graft-versus-host disease, multiple sclerosis, rheumatoid arthritis, psoriasis, lupus erythematosus, diabetes, mycosis fungoides (Alibert-Bazin syndrome), or scleroderma.

2. BACKGROUND

Human stem cells are totipotential or pluripotential precursor cells capable of generating a variety of mature human cell lineages. Evidence exists that demonstrates that stem cells can be employed to repopulate many, if not all, tissues and restore physiologic and anatomic functionality.

Many different types of mammalian stem cells have been characterized. See, e.g., Caplan et al., U.S. Pat. No. 5,486,359 (human mesenchymal stem cells); Boyse et al., U.S. Pat. No. 5,004,681 (fetal and neonatal hematopoietic stem and progenitor cells); Boyse et al., U.S. Pat. No. 5,192,553 (same); Beltrami el al., $Cell$ 114(6):763-766 (2003) (cardiac stem cells); Forbes et al., $J. Pathol.$ 197(4):510-518 (2002) (hepatic stem cells). Umbilical cord blood, and total nucleated cells derived from cord blood, have been used in transplants to restore, partially or fully, hematopoietic function in patients who have undergone ablative therapy.

The placenta is a particularly attractive source of stem cells. Because mammalian placentas are plentiful and are normally discarded as medical waste, they represent a unique source of medically-useful stem cells. Provided herein are such isolated placental stem cells, populations of the placental stem cells, and methods of using the same to treat disease, disorder or condition caused by, or relating to, an unwanted or deleterious immune response, for example, inflammatory bowel disease, graft-versus-host disease, multiple sclerosis, rheumatoid arthritis, psoriasis, lupus erythematosus, diabetes, mycosis fungoides (Alibert-Bazin syndrome), or scleroderma.

3. SUMMARY

Provided herein are methods of treating, managing, ameliorating or preventing diseases, disorders and/or conditions associated with or caused by an immune response, e.g., associated with, resulting in or caused by inflammation. In one embodiment, provided herein is a method of treating an individual having or at risk of developing a disease, disorder or condition associated with or caused by harmful, deleterious, inappropriate or unwanted immune response, e.g., inflammation, comprising administering to the individual a therapeutically effective amount of placental stem cells, or medium conditioned by placental stem cells, wherein the therapeutically effective amount is an amount sufficient to cause a detectable improvement in one or more symptoms of, or a reduction in the progression of one or more symptoms of, said disease, disorder or condition. Also provided herein is the use of placental stem cells in the manufacture of a medicament for treating, managing, ameliorating or preventing diseases, disorders and/or conditions associated with or caused by an immune response, e.g., associated with, resulting in or caused by inflammation. In a specific embodiment, said placental stem cells are $CD10^+$, $CD34^-$, $CD105^+$, $CD200^+$ placental stem cells. In another specific embodiment, said placental stem cells express CD200 and HLA-G, or express CD73, CD105, and CD200, or express CD200 and OCT-4, or express CD73, CD105 and HLA-G, or express CD73 and CD105 and facilitate the formation of one or more embryoid-like bodies in a population of placental cells comprising said stem cell when said population is cultured under conditions that allow for the formation of an embryoid-like body, or express OCT-4 and (c) facilitate the formation of one or more embryoid-like bodies in a population of placental cells comprising said stem cell when said population is cultured under conditions that allow for the formation of an embryoid-like body. In a more specific embodiment, the placental stem cells suppress the activity of an immune cell, e.g., suppress proliferation of a T cell.

In a specific embodiment, said disease, disorder or condition is an inflammatory bowel disease. In a more specific embodiment, said inflammatory bowel disease is Crohn's disease. In another more specific embodiment, said Crohn's disease is gastroduodenal Crohn's disease. In another more specific embodiment, said Crohn's disease is jejunoileitis. In another more specific embodiment, said Crohn's disease is ileitis. In another more specific embodiment, said Crohn's disease is ileocolitis. In another more specific embodiment, said Crohn's disease is Crohn's colitis. In another specific embodiment, said inflammatory bowel disease is ulcerative colitis.

In a more specific embodiment, said symptom of inflammatory bowel disease is one or more of inflammation and swelling of a part of the GI tract, abdominal pain, frequent emptying of the bowel, diarrhea, rectal bleeding, anemia, weight loss, arthritis, skin problems, fever, thickening of the intestinal wall, formation of scar tissue in the intestines, formation of sores or ulcers in the intestine, development of one or more fistulas in the intestinal wall, development of one or more fissures in the anus, development of a nutritional deficiency, development of kidney stones, development of gallstones, development of a disease of the liver or biliary system, bloody diarrhea, nausea, abdominal cramps, anemia, fatigue, weight loss, loss of appetite, loss of bodily fluids and nutrients, skin lesions, joint pain, growth failure, development of osteoporosis, or eye inflammation.

In another specific embodiment, said symptom of inflammatory bowel disease, and is one or more of pruritic or painful rash, fever, generalized erythroderma, desquamation, raised (e.g., higher than normal) levels of bilirubin, raised levels of alanine aminotransferase (ALT), raised levels of aspartate aminotransferase (AST), raised levels of alkaline phosphatase (AP), diarrhea, internal bleeding, cramping, abdominal pain, and ileus, burning sensation in the eye, eye irritation, photophobia, eye pain due to decreased tear secretion; dryness of the mouth, sensitivity to spicy or acidic foods, abdominal pain, dysphagia, odynophagia, weight loss, obstructive lung disease, muscular weakness, neuropathic pain, or muscle cramps.

In another specific embodiment, said disease, disorder or condition is graft-versus-host disease. In a more specific embodiment, said graft-versus-host disease develops after an allogeneic bone marrow transplant. In another more specific embodiment, said graft-versus-host disease develops after a solid organ transplant. In another more specific embodiment, said graft-versus-host disease develops after a composite tissue allograft. In another more specific embodiment, said graft-versus-host disease is reduced in grade by at least one step by said administering. In another more specific embodiment, said graft-versus-host disease does not progress beyond grade II within 100 days after transplantation as a result of said administering. In another more specific embodiment, said graft-versus-host disease does not progress beyond grade I within 100 days after transplantation as a result of said administering.

In another specific embodiment, said disease, disorder or condition is rheumatoid arthritis (RA). In a more specific embodiment, the administration is sufficient to cause a detectable improvement in one or more symptoms of RA, or sufficient to detectably reduce the onset of one or more symptoms of RA, in at least one joint in the individual with RA. In another specific embodiment, the administration is sufficient to cause a detectable improvement in one or more symptoms of RA, or sufficient to detectably reduce the onset of one or more symptoms of RA, in at least one non-joint tissue in the individual with RA. In a more specific embodiment, said non-joint tissue is skin (dermis), lungs, autoimmune system or blood, renal tissue, cardiovascular tissue, ocular tissue, or neurological tissue. In a more specific embodiment, said symptom of RA is a condition adjunct to RA. In a more specific embodiment, said condition adjunct to RA is pyoderma gangrenosum, neutrophilic dermatosis, Sweet's syndrome, viral infection, erythema nodosum, lobular panniculitis, atrophy of digital skin, palmar erythema, diffuse thinning (rice paper skin), skin fragility, subcutaneous nodules on an exterior surface, e.g., on the elbows, fibrosis of the lungs (e.g., as a consequence of methotrexate therapy), Caplan's nodules, vasculitic disorders, nail fold infarcts, neuropathy, nephropathy, amyloidosis, muscular pseudohypertrophy, endoscarditis, left ventricular failure, valulitis, scleromalacia, mononeuritis multiplex, atlanto-axial subluxation. In another specific embodiment of the method, a plurality of the placental or umbilical cord stem cells has been genetically engineered to express a fusion protein comprising IL-1Ra and DHFR.

In another specific embodiment, the disease, disorder or condition is multiple sclerosis. In a more specific embodiment, said multiple sclerosis is relapsing/remitting multiple sclerosis, secondary progressive multiple sclerosis, primary progressive multiple sclerosis, or progressive/relapsing multiple sclerosis. In another specific embodiment, said symptom of multiple sclerosis is one or more of a sensory disturbance in a limb, optic nerve dysfunction, pyramidal tract dysfunction, bladder dysfunction, bowel dysfunction, sexual dysfunction, ataxia, or diplopia.

In another specific embodiment, the disease, disorder or condition is lupus erythematosus. In a more specific embodiment, said symptom of lupus erythematosus is one or more of malar rash, butterfly rash, discoid lupus, alopecia, mouth, nasal, and vaginal ulcers, lesions on the skin, joint pain anemia and/or iron deficiency, lower than normal platelet and white blood cell counts, antiphospholipid antibody syndrome, presence of anticardiolipin antibody in the blood, pericarditis, myocarditis, endocarditis, lung and/or pleural inflammation, pleuritis, pleural effusion, lupus pneumonitis, chronic diffuse interstitial lung disease, pulmonary hypertension, pulmonary emboli, pulmonary hemorrhage, painless hematuria or proteinuria, lupus nephritis, renal failure, and/or development of membranous glomerulonephritis with "wire loop" abnormalities); neurological manifestations (e.g., seizures, psychosis, abnormalities in the cerebrospinal fluid); T-cell abnormalities (e.g., deficiency in CD45 phosphatase and/or increased expression of CD40 ligand); and/or nonspecific manifestations (e.g., lupus gastroenteritis, lupus pancreatitis, lupus cystitis, autoimmune inner ear disease, parasympathetic dysfunction, retinal vasculitis, systemic vasculitis, increased expression of FcεRIγ, increased and sustained calcium levels in T cells, increase of inositol triphosphate in the blood, reduction in protein kinase C phosphorylation, reduction in Ras-MAP kinase signaling, and/or a deficiency in protein kinase A I activity.

In another specific embodiment, said disease, disorder or condition is scleroderma. In a more specific embodiment, the scleroderma is diffuse scleroderma. In a more specific embodiment, the scleroderma is limited scleroderma (CREST syndrome). In a more specific embodiment, the scleroderma is morphea/linear scleroderma. In another more specific embodiment, said symptom is one or more of hardening of the skin of the face, hardening of the skin of the fingers, Reynaud's syndrome, inappropriate vasoconstriction in an extremity, calcinosis, telangiectasia, esophageal dysmotility, or presence in the blood of an anti-centromere antibody or an anti-scl70/anti-topoisomerase antibody. In another more specific embodiment, the method comprises administering a second therapeutic agent to said individual. In a more specific embodiment, said second therapeutic agent is an anti-inflammatory drug, a proton pump inhibitor, an immunosuppressant compound, or a vasodilator.

In another specific embodiment, said disease, disorder or condition is mycosis fungoides (Alibert-Bazin syndrome). In a more specific embodiment, said mycosis fungoides is in the patch phase. In a more specific embodiment, said mycosis fungoides is in the skin tumor phase. In another more specific embodiment, said mycosis fungoides is in the skin redness (erythroderma) stage. In another more specific embodiment, said mycosis fungoides is in the lymph node stage. In another more specific embodiment, said symptom is one or more of development of flat, red patches that are itchy; development of flat, red patches that are raised and hard (plaques); development of raised lumps (nodules) appear; development of large red, itchy, scaly areas over the body; cracking of the skin of the palms and soles; thickening of the skin of the palms and soles; and crack; or inflammation of the lymph nodes. In another more specific embodiment, the method comprises administering a second therapeutic agent to said individual. In a more specific embodiment, said second therapeutic agent is an anti-inflammatory drug, an immunosuppressant compound, exposure to sunlight, exposure to ultraviolet light, a topical steroid, local superficial radiotherapy, total skin electron beam radiation, application of organic honey to skin affected by erythroderma, an interferon, a retinoid, a rexinoid, or vorinostat.

In another embodiment, said disease, disorder or condition is diabetes. In a specific embodiment, said diabetes is diabetes mellitus Type 1.

In another embodiment, said disease, disorder or condition is psoriasis. In a more specific embodiment, the psoriasis is plaque psoriasis (psoriasis vulgaris). In another more specific embodiment, said psoriasis is flexural psoriasis (inverse psoriasis). In another more specific embodiment, said psoriasis is guttate psoriasis. In another more specific embodiment, said psoriasis is pustular psoriasis. In another more specific embodiment, said psoriasis is nail psoriasis. In another more specific embodiment, said psoriasis is psoriatic arthritis. In another more specific embodiment, said psoriasis is erythrodermic psoriasis. In another specific embodiment, the therapeutically effective amount of placental stem cells or umbilical cord stem cells, or culture medium conditioned by placental stem cells or umbilical cord stem cells is an amount sufficient to cause a 5, 10, 15, 20, 25, 30, 35, 40 or more point reduction in the Psoriasis Area Severity Index. In one embodiment, the invention provides for the administration of an effective dose placental stem cells to an individual affected with psoriasis, wherein said effective dose is an amount of placental stem cells sufficient, e.g., to cause a detectable improvement in, reduce the severity of, or reduce the progression of, one or more of the symptoms of psoriasis. In a more specific embodiment, said one or more symptoms is development of one or more of raised areas of inflamed skin covered with silvery white scaly skin; development of plaques; smooth inflamed patches of skin occurring in skin folds; development of one or more small oval spots; development of one or more pustules; a change in the appearance of one or more finger nails or toe nails; onycholysis; crumbling of one or more nails; joint and connective tissue inflammation; dactylitis; spondylitis; widespread inflammation and exfoliation of the skin over most of the body surface; or severe itching, swelling and/or pain. In another specific embodiment, the method comprises additionally administering one or more therapeutic agents or therapies, wherein said therapeutic agents or therapies comprise one or more of a cream or ointment comprising a corticosteroid, a cream or ointment comprising a vitamin $D_3$ analog, a cream or ointment comprising a anthralin, a cream or ointment comprising a argan oil, a cream or ointment comprising a retinoid, or a cream or ointment comprising coal tar; one or more exposures, e.g., for about 1, 2, 3, 4, 5, 6, 7, 8, 9, 10, 12, 14, 16, 18 or 20 minutes, to ultraviolet light, e.g., UVB of a wavelength between about 280 nm to about 315 nm, particularly about 311 nm to about 312 nm; topical administration of psoralen in combination with exposure to UVA light; or one or more systemic administrations of one or more of methotrexate, cyclosporine, a retinoid, tioguanine, hydroxyurea, sulfasalazine, mycophenolate mofetil, azathioprine, oral tacrolimus and/or a fumaric acid ester.

In another specific embodiment of any of the above methods, the method comprises administration of a second therapeutic agent to the individual having the disease, disorder or condition. In a more specific embodiment, said second therapeutic agent is an anti-inflammatory agent, an immunomodulatory agent, and immunosuppressive agent, a pain medication, or an antibiotic. In a more specific embodiment, the second therapeutic agent is an immunomodulatory agent. In a more specific embodiment, said immunomodulatory agent is an immune suppressant. In an even more specific embodiment, said immune suppressive agent is an anti-CD3 antibody (e.g., OKT3, muronomab), an anti-IL-2 receptor antibody (e.g., basiliximab (SIMTJILECT®) and daclizumab (ZENAPAX®)), an anti T cell receptor antibody (e.g., Muromonab-CD3), azathioprine, a calcineurin inhibitor, a corticosteroid, cyclosporine, methotrexate, mercaptopurine, mycophenolate mofetil, tacrolimus, or sirolimus. In another more specific embodiment, the second therapeutic agent comprises a stem cell of another type, e.g., a bone marrow-derived mesenchymal stem cell, bone marrow, or a hematopoietic stem cell.

3.1 Definitions

As used herein, the term "SH2" refers to an antibody that binds an epitope on the marker CD105. Thus, cells that are referred to as SH2$^+$ are CD105$^+$.

As used herein, the terms "SH3" and SH4" refer to antibodies that bind epitopes present on the marker CD73. Thus, cells that are referred to as SH3$^+$ and/or SH4$^+$ are CD73$^+$.

As used herein, the term "isolated stem cell" means a stem cell that is substantially separated from other, non-stem cells of the tissue, e.g., placenta, from which the stem cell is derived. A stem cell is "isolated" if at least 50%, 60%, 70%, 80%, 90%, 95%, or at least 99% of the non-stem cells with which the stem cell is naturally associated are removed from the stem cell, e.g., during collection and/or culture of the stem cell.

As used herein, the term "isolated population of cells" means a population of cells that is substantially separated from other cells of the tissue, e.g., placenta, from which the population of cells is derived. A population of, e.g., stem cells is "isolated" if at least 50%, 60%, 70%, 80%, 90%, 95%, or at least 99% of the cells with which the population of stem cells are naturally associated are removed from the population of stem cells, e.g., during collection and/or culture of the population of stem cells.

As used herein, the term "placental stem cell" refers to a stem cell or progenitor cell that is derived from a mammalian placenta, regardless of morphology, cell surface markers, or the number of passages after a primary culture, which adheres to a tissue culture substrate (e.g., tissue culture plastic or a fibronectin-coated tissue culture plate). The term "placenta stem cell" as used herein does not, however, refer to a trophoblast, a cytotrophoblast, embryonic germ call, or embryonic stem cell, as those cells are understood by persons of skill in the art. A cell is considered a "stem cell" if the cell retains at least one attribute of a stem cell, e.g., a marker or gene expression profile associated with one or more types of stem cells; the ability to replicate at least 10-40 times in culture; multipotency, e.g., the ability to differentiate, either in vitro, in vivo or both, into cells of one or more of the three germ layers; the lack of adult (i.e., differentiated) cell characteristics, or the like. The terms "placental stem cell" and "placenta-derived stem cell" may be used interchangeably. Unless otherwise noted herein, the term "placental" includes the umbilical cord. The placental stem cells disclosed herein are, in certain embodiments, multipotent in vitro (that is, the cells differentiate in vitro under differentiating conditions), multipotent in vivo (that is, the cells differentiate in vivo), or both.

As used herein, a stem cell is "positive" for a particular marker when that marker is detectable. For example, a placental stem cell is positive for, e.g., CD73 because CD73 is detectable on placental stem cells in an amount detectably greater than background (in comparison to, e.g., an isotype control). A cell is also positive for a marker when that marker can be used to distinguish the cell from at least one other cell type, or can be used to select or isolate the cell when present or expressed by the cell.

As used herein, "immunomodulation" and "immunomodulatory" mean causing, or having the capacity to cause, a detectable change in an immune response, and the ability to cause a detectable change in an immune response.

As used herein, "immunosuppression" and "immunosuppressive" mean causing, or having the capacity to cause, a detectable reduction in an immune response, and the ability to cause a detectable suppression of an immune response.

4. BRIEF DESCRIPTION OF THE FIGURES

FIG. 1: Viability of placental stem cells from perfusion (A), amnion (B), chorion (C), or amnion-chorion plate (D), or umbilical cord stem cells (E). Numbers on X-axis designate placenta from which stem cells were obtained.

Figure 2:
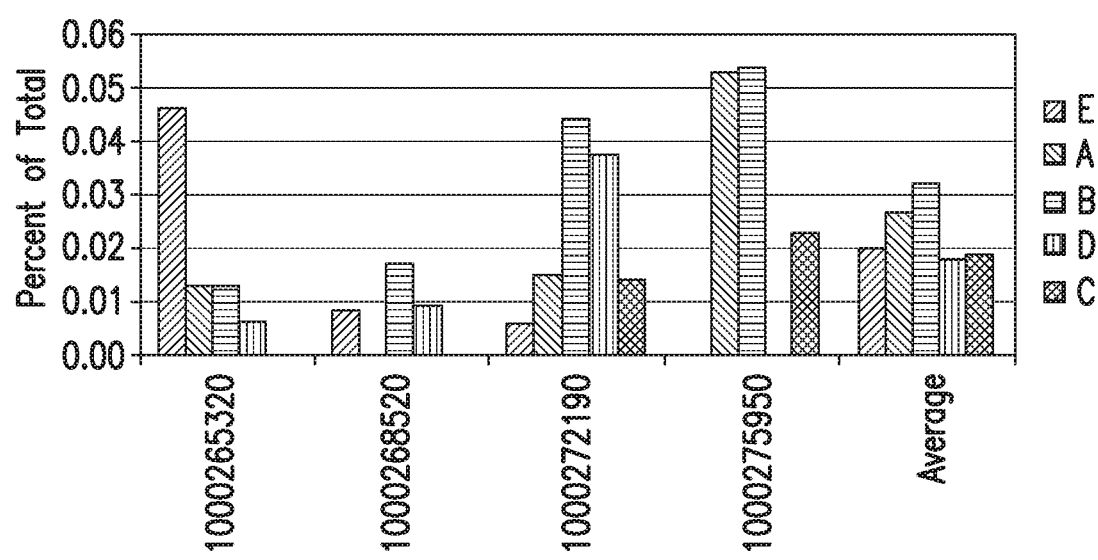

FIG. 2: Percent HLA ABC−/CD45−/CD34−/CD133+ cells from perfusion (A), amnion (B), chorion (C), or amnion-chorion plate (D), or umbilical cord stem cells (E) as determined by FACSCalibur. Numbers on X-axis designate placenta from which stem cells were obtained.

Figure 3:
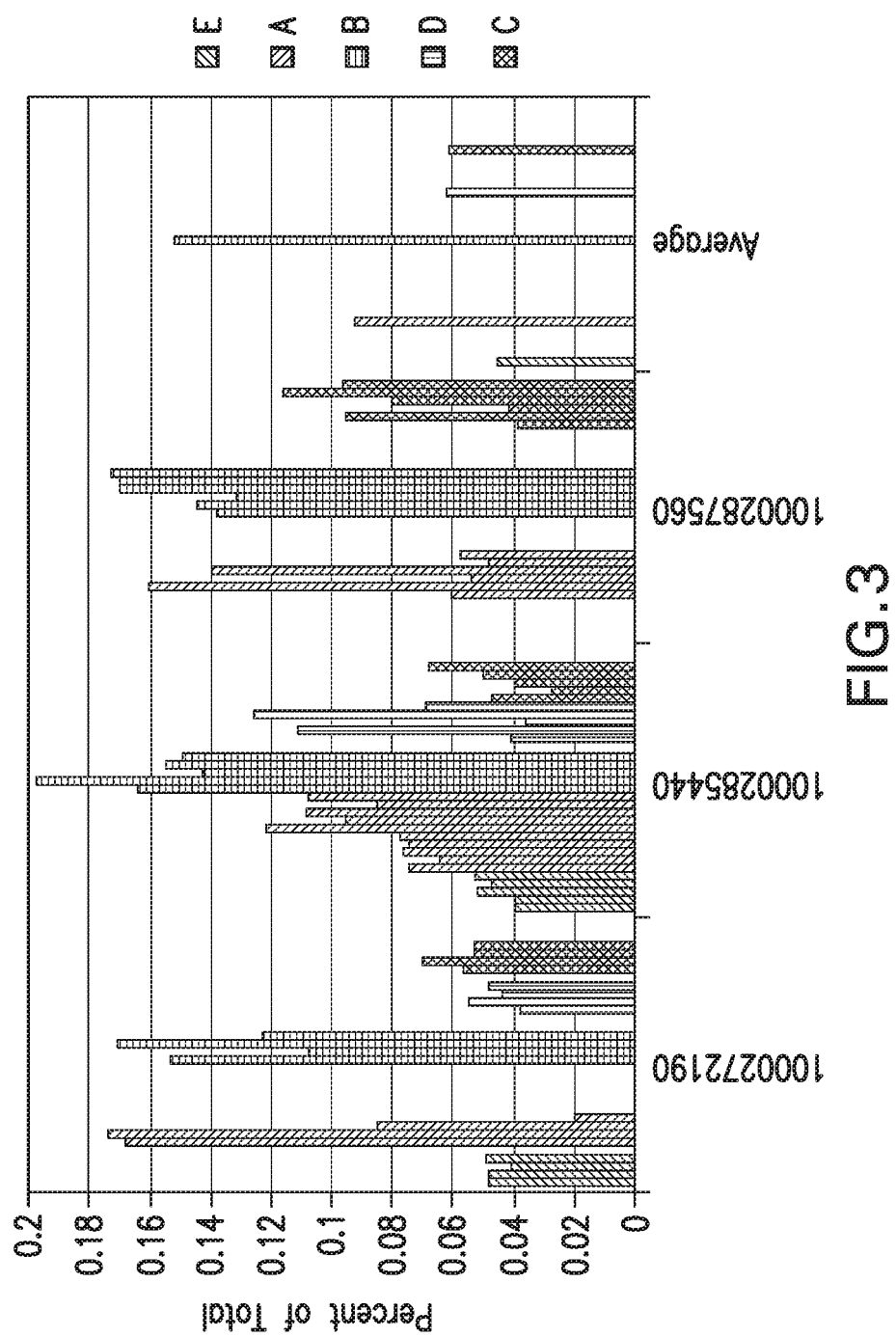

FIG. 3: Percent HLA ABC−/CD45−/CD34−/CD133+ cells from perfusion (A), amnion (B), chorion (C), or amnion-chorion plate (D), or umbilical cord stem cells (E), as determined by FACS Aria. Numbers on X-axis designate placenta from which stem cells were obtained.

Figure 4:
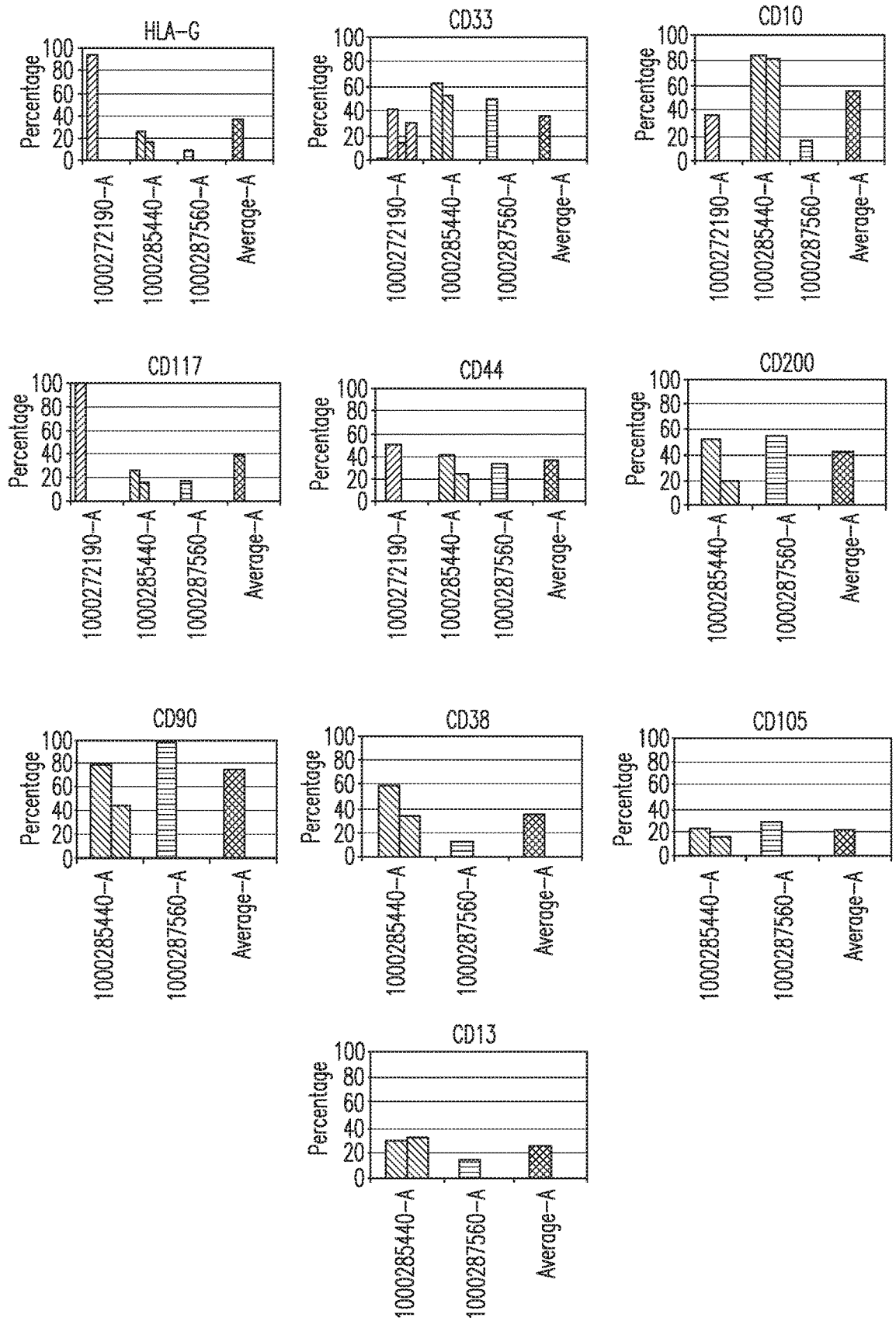

FIG. 4: HLA-G, CD10, CD13, CD33, CD38, CD44, CD90, CD105, CD117, CD200 expression in stem cells derived from placental perfusate.

Figure 5:
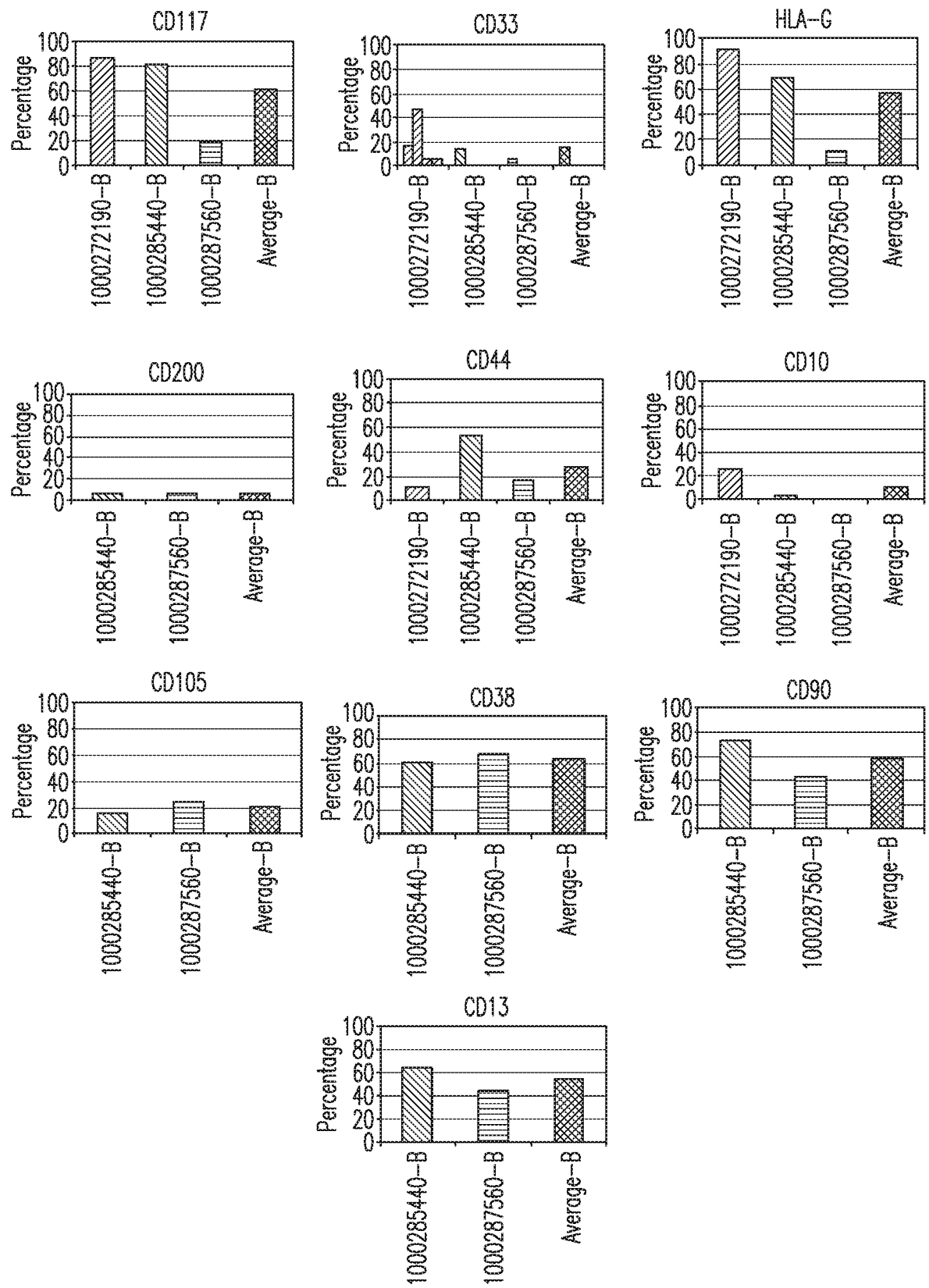

FIG. 5: HLA-G, CD10, CD13, CD33, CD38, CD44, CD90, CD105, CD117, CD200 expression in stem cells derived from amnion.

Figure 6:
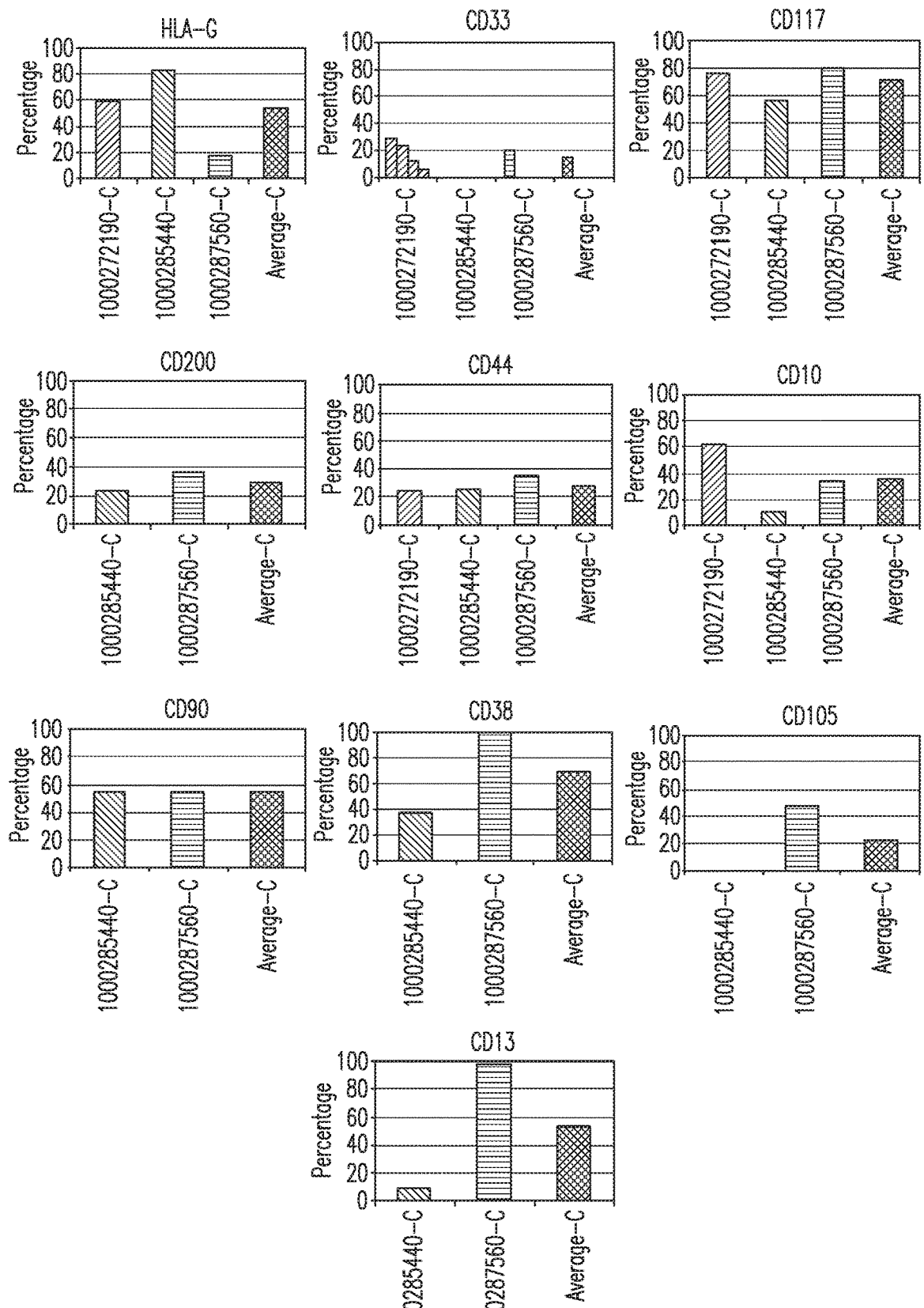

FIG. 6: HLA-G, CD10, CD13, CD33, CD38, CD44, CD90, CD105, CD117, CD200 expression in stem cells derived from chorion.

Figure 7:
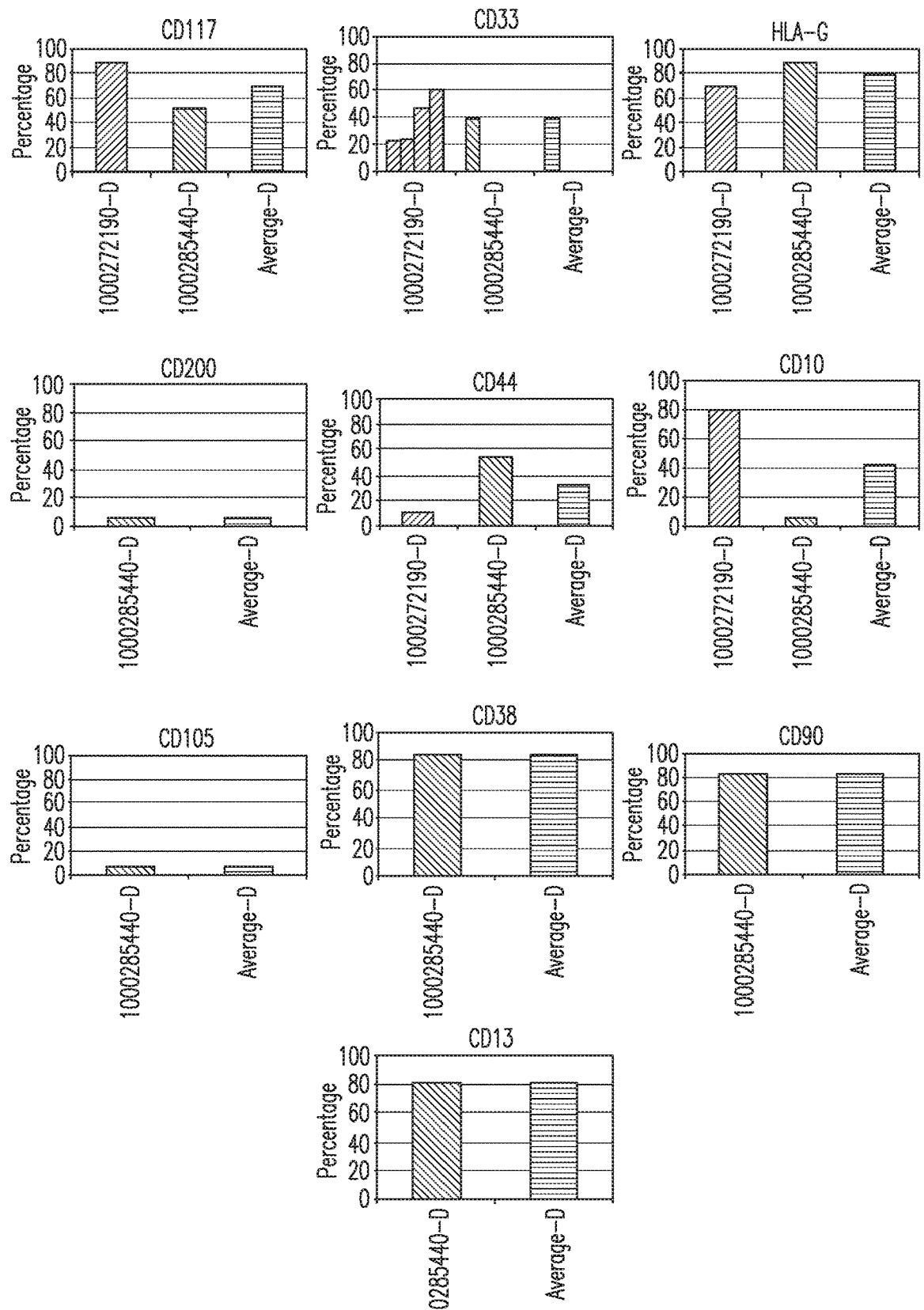

FIG. 7: HLA-G, CD10, CD13, CD33, CD38, CD44, CD90, CD105, CD117, CD200 expression in stem cells derived from amnion-chorion plate.

Figure 8:
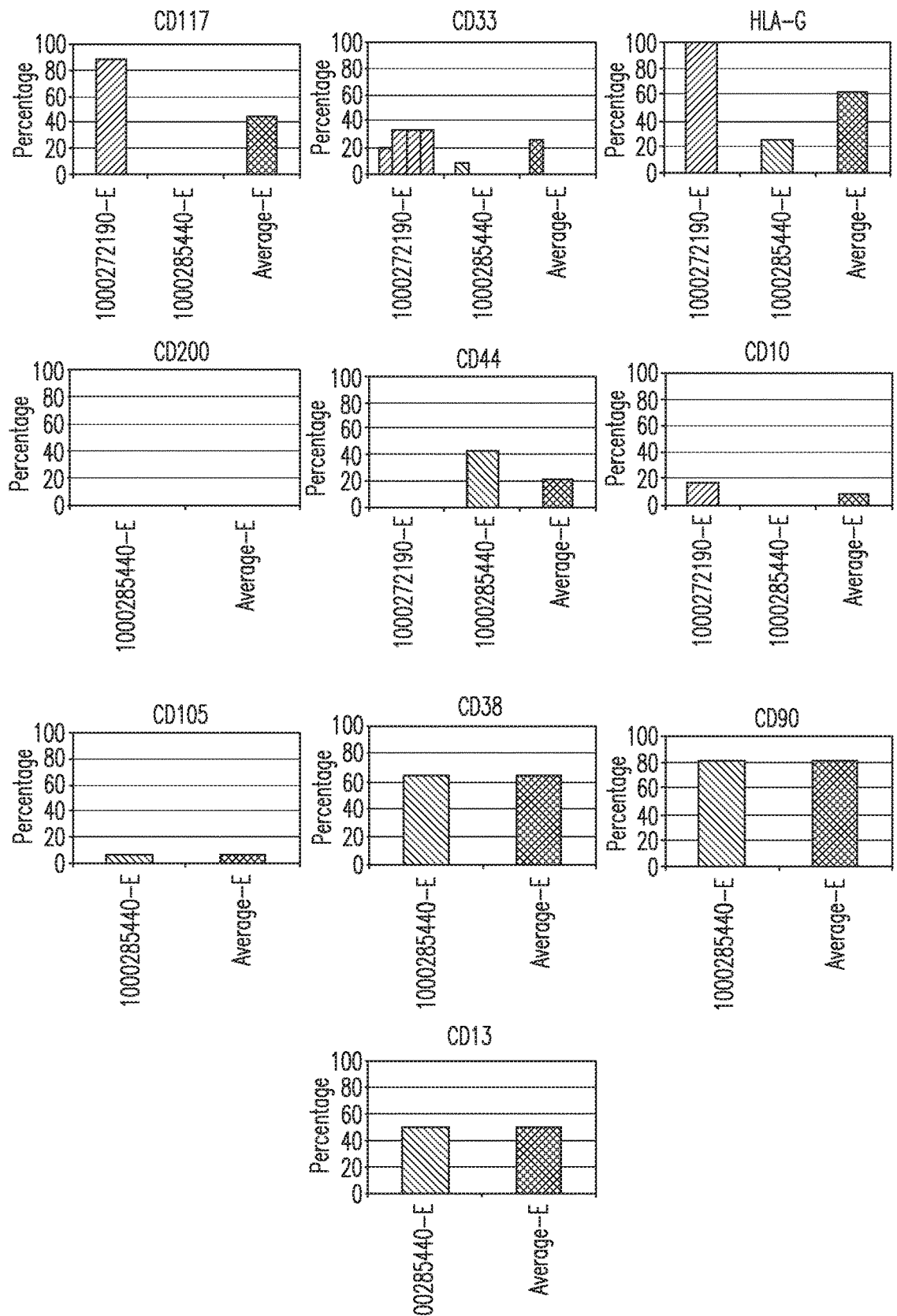

FIG. 8: HLA-G, CD10, CD13, CD33, CD38, CD44, CD90, CD105, CD117, CD200 expression in stem cells derived from umbilical cord.

Figure 9:
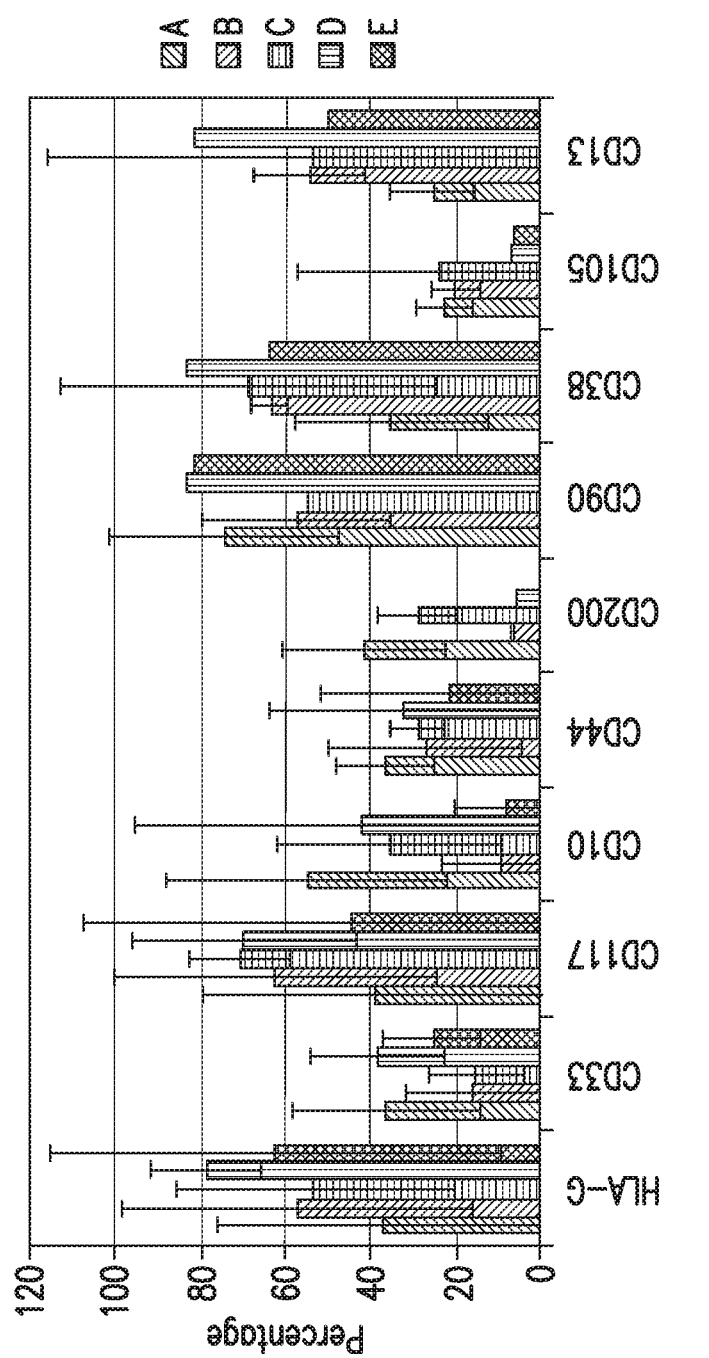

FIG. 9: Average expression of HLA-G, CD10, CD13, CD33, CD38, CD44, CD90, CD105, CD117, CD200 expression in stem cells derived from perfusion (A), amnion (B), chorion (C), amnion-chorion plate (D) or umbilical cord (E).

Figure 10A:
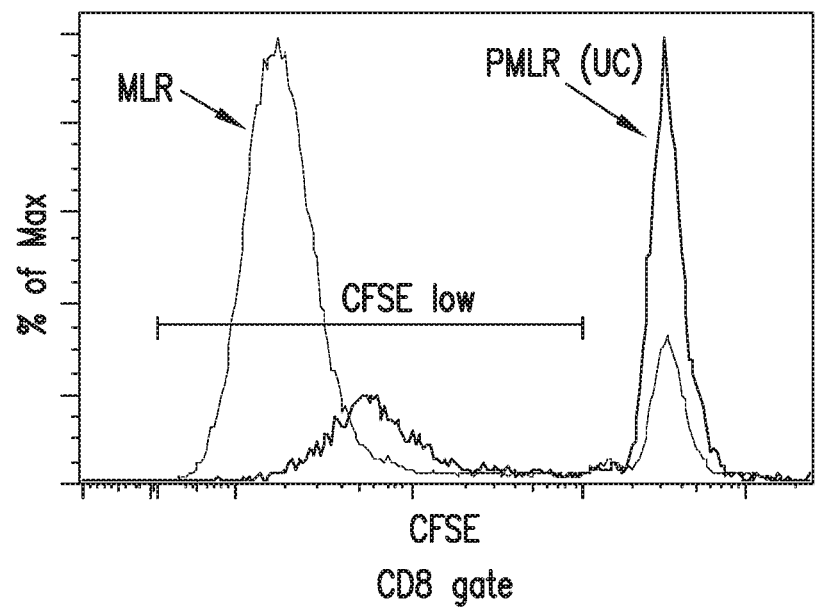
Figure 10B:
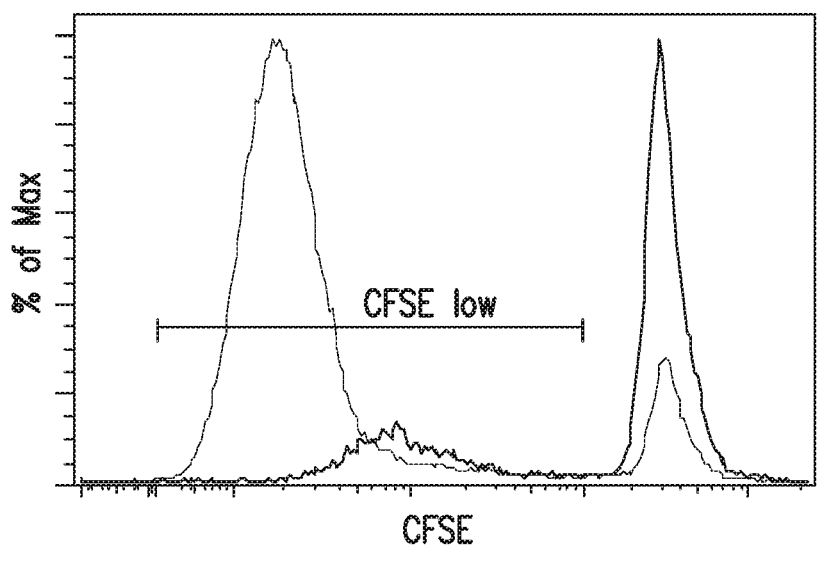

FIGS. 10A and 10B: The mixed lymphocyte reaction (MLR) is a model for the naïve immune response, and is inhibited by placental stem cells. From the gated "live" and CD8+ and CD4+ T cell gates, the percentage of carboxyfluorescein succinimidyl ester (CFSE)$^{LOW}$ cells was monitored (FIGS. 10A and 10B, respectively).

Figure 11:
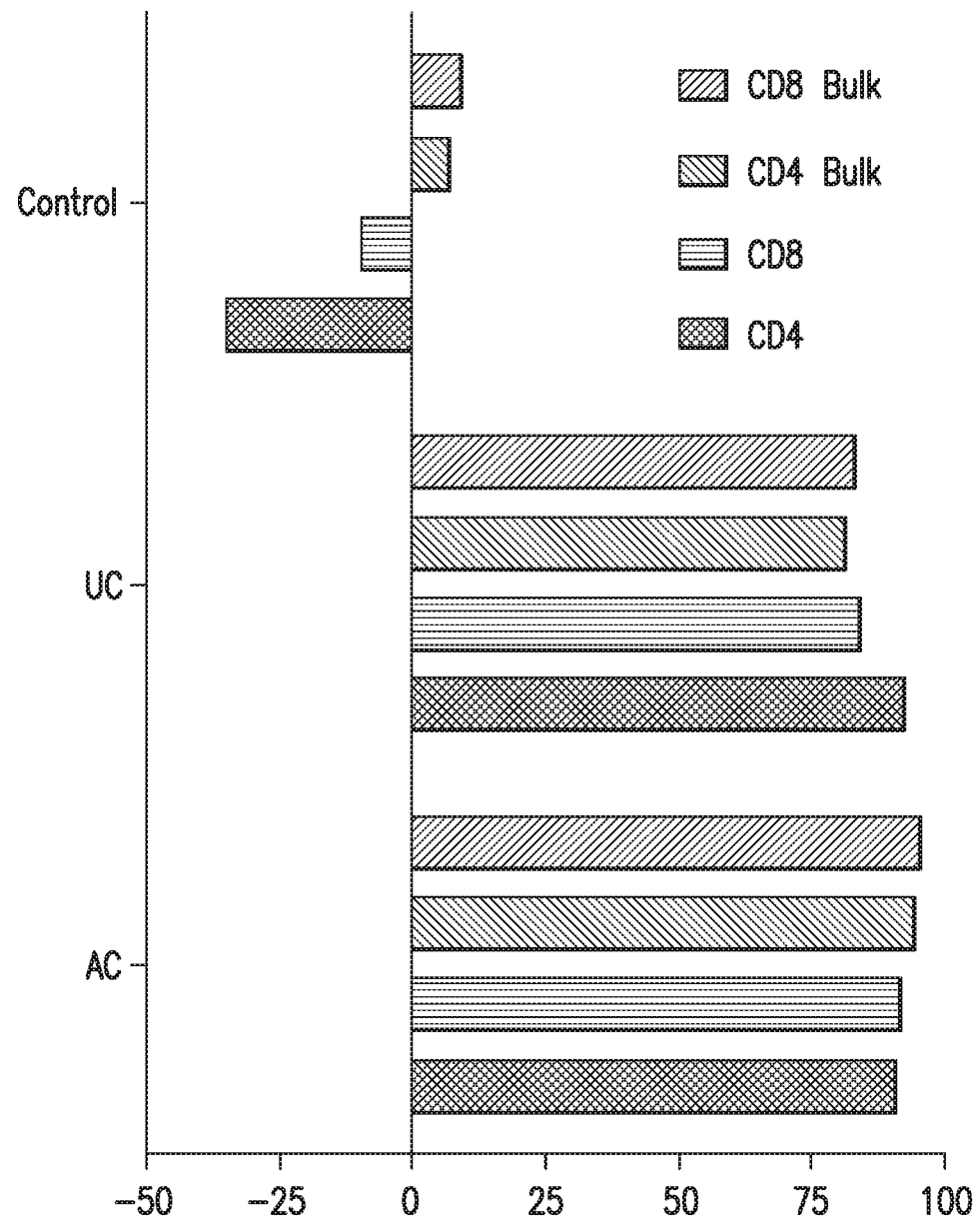

FIG. 11: Placenta-derived stem cells from amnion chorionic plate (AC) and umbilical cord stroma (UC) suppress the allo-MLR. The MLR is performed with either CD4+ T cells, CD8+ T cells, or equal amounts of CD4+ and CD8+ T cells. Abscissa: percent suppression of proliferation.

Figure 12A:
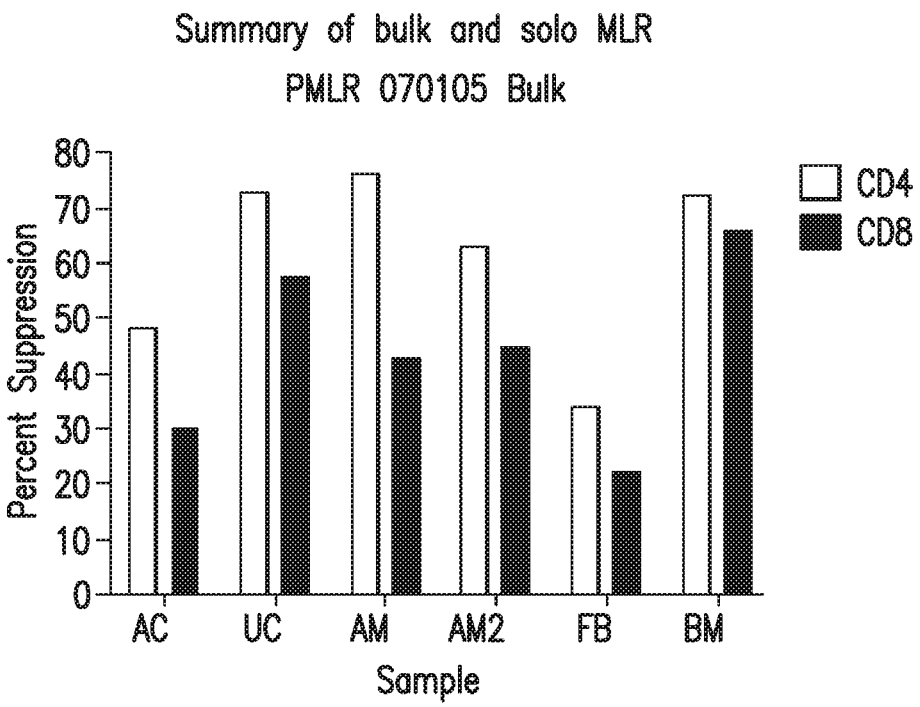
Figure 12B:
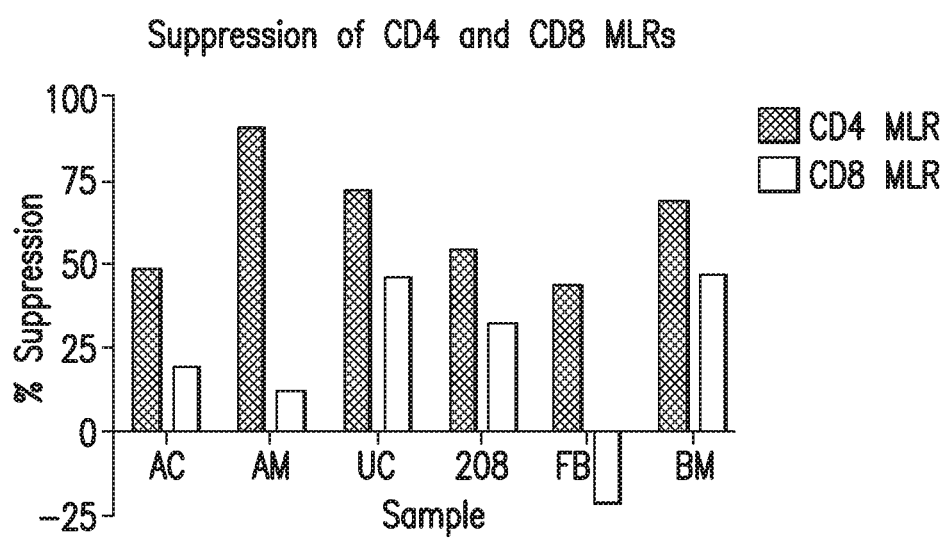

FIG. 12A and FIG. 12B: Placental stem cells and umbilical cord stem cells inhibit the allo-MLR. A six day assay in round bottom 96 well plate wells. Placental cells:T cells:Dendritic cells=approximately 1:10:1. Stem cells were obtained from amnion-chorion (AC), amniotic membrane (AM) or umbilical cord (UC). FB=fibroblast. BM=bone marrow-derived mesenchymal stem cells.

Figure 13:
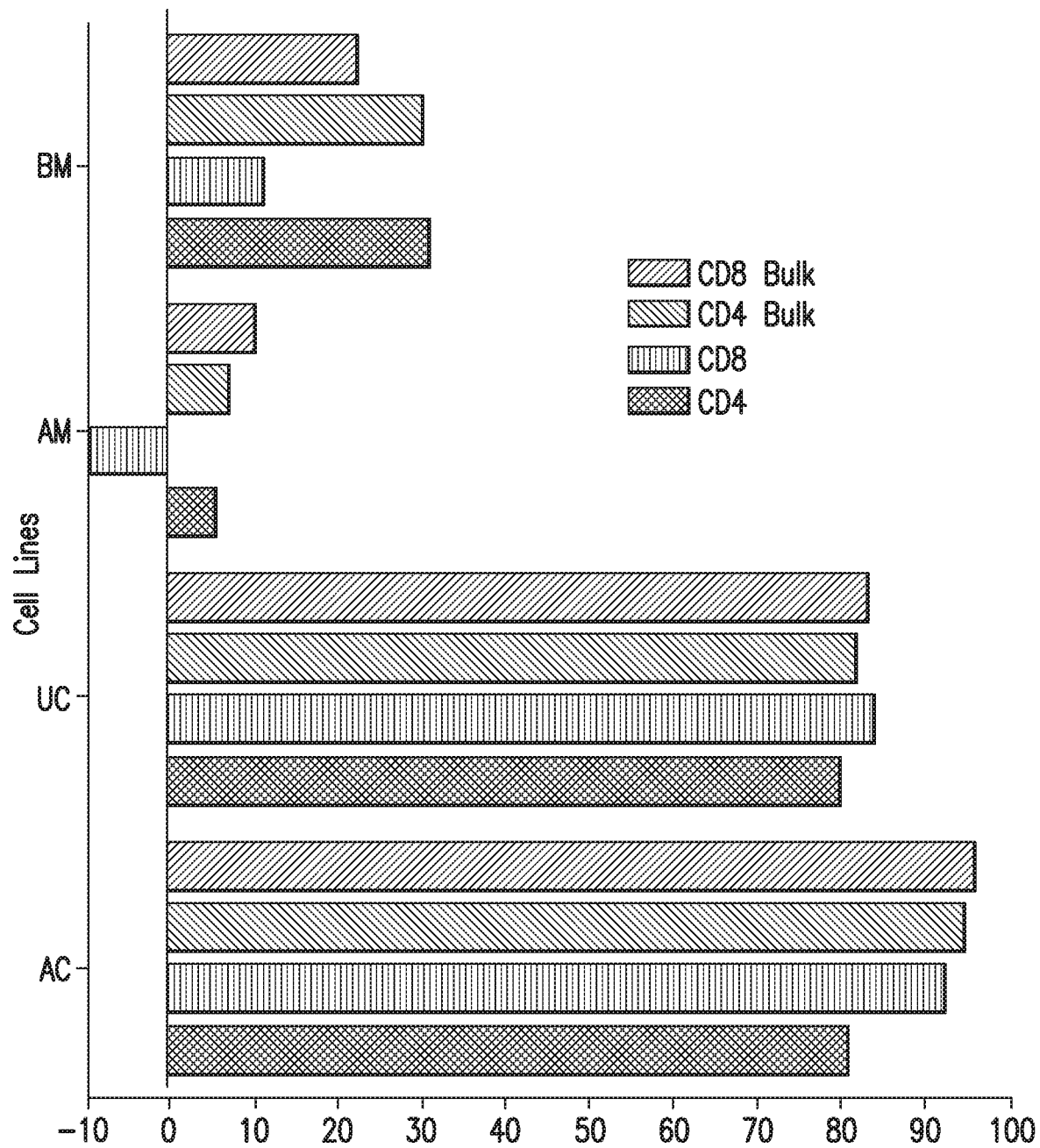

FIG. 13: Placental stem cells from different donors suppress the allo-MLR to different extents. The figure compares suppression in an MLR by placental stem cells from two placental donors, designated 61665 and 63450. Stem cells from placenta 63450 appears to suppress the MLR to a greater degree than stem cells from placenta 61665.

Figure 14:
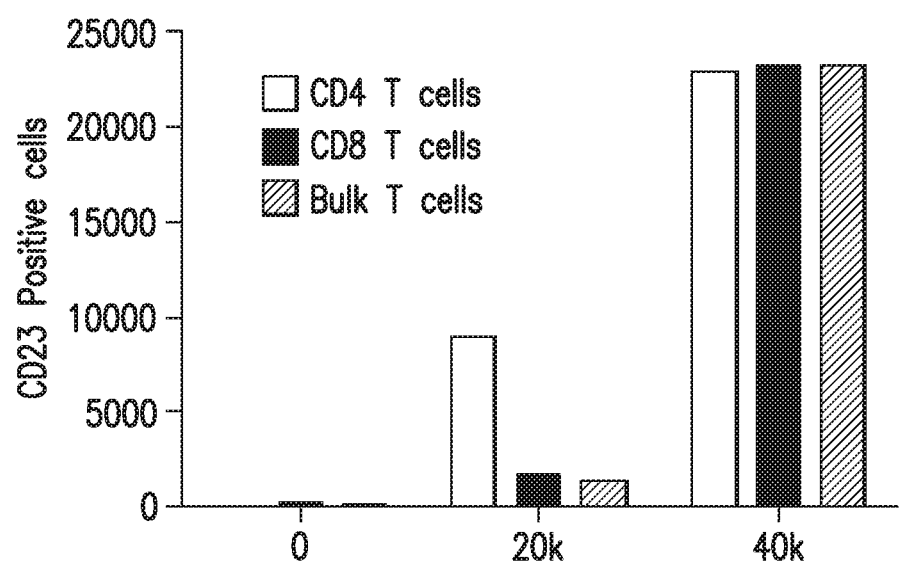

FIG. 14: Seventeen day regression assay and the modified placental stem cell regression assay. The x axis represents the number of placental stem cells added to the assay. The number of surviving CD23+ LCL (lymphoblastoid cell line, an artificially-created transformed B cell line) is measured on the Y axis.

Figure 15:
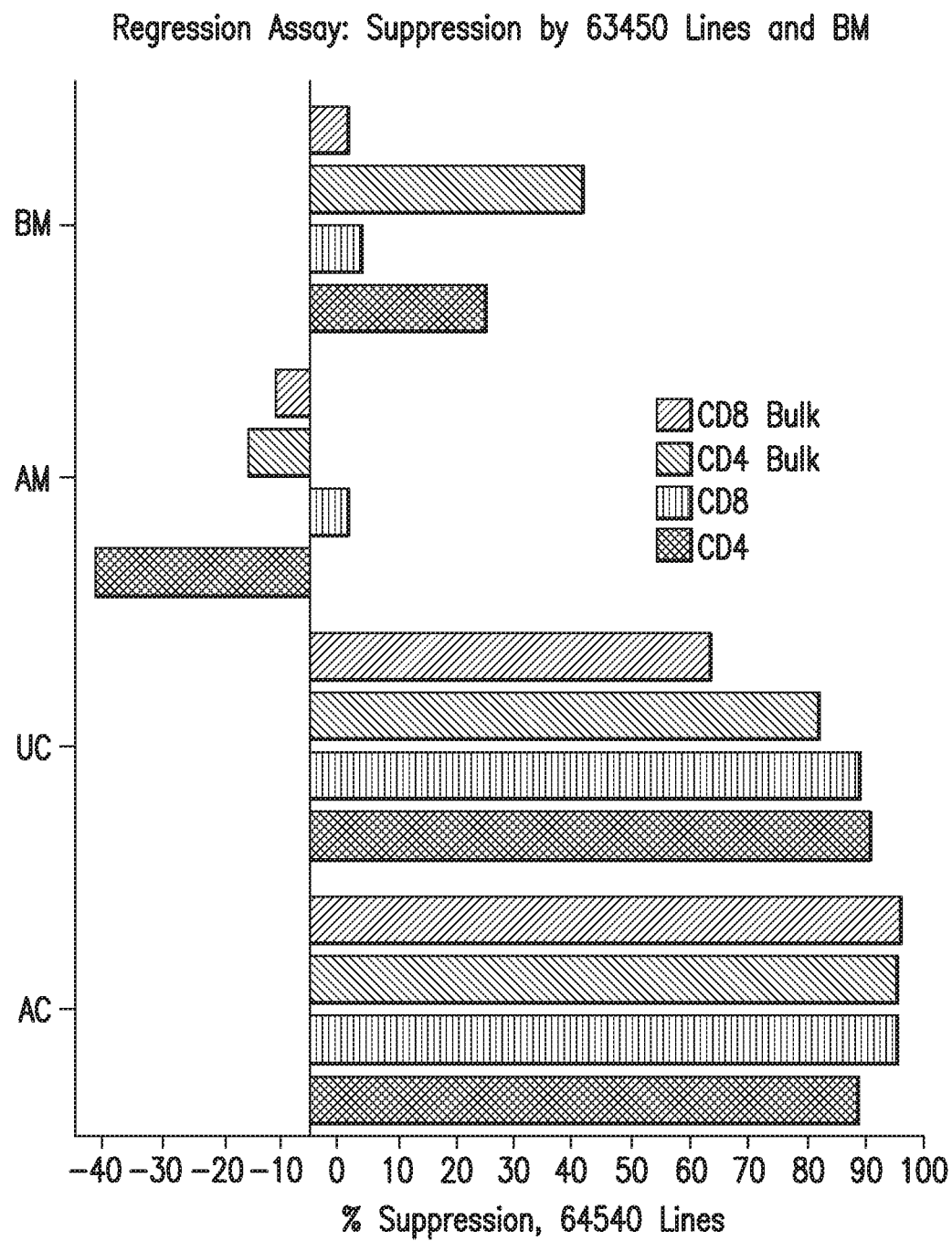

FIG. 15: Placental stem cell suppression of T cell proliferation in the six day regression assay. A regression assay was set up using CFSE stained T cells. After six days, T cell proliferation was assessed. Relative suppression of T cell proliferation by stem cells from amnion-chorion (AC), umbilical cord (UC), amniotic membrane (AM), or bone marrow (BM) is shown.

Figure 16:
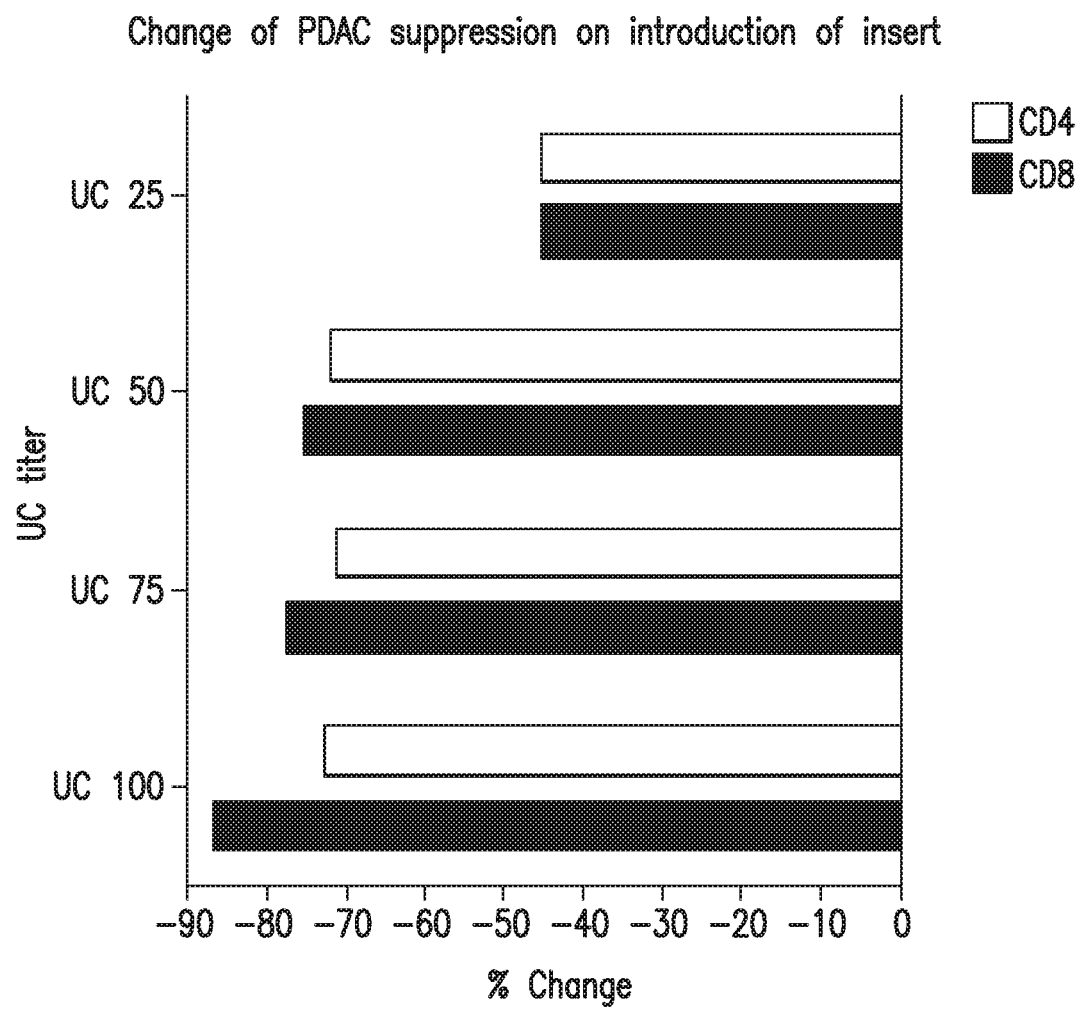

FIG. 16: Percentage change in suppression on introduction of transwell insert in the MLR, separating placental cells from T cells but allowing exchange of culture medium. Umbilical cord stem cells at 25,000, 50,000, 75,000 or 100,000 per reaction show both a relatively high degree of suppression and a relatively high degree of need for cell to cell contact in the high titers to accomplish the suppression.

Figure 17:
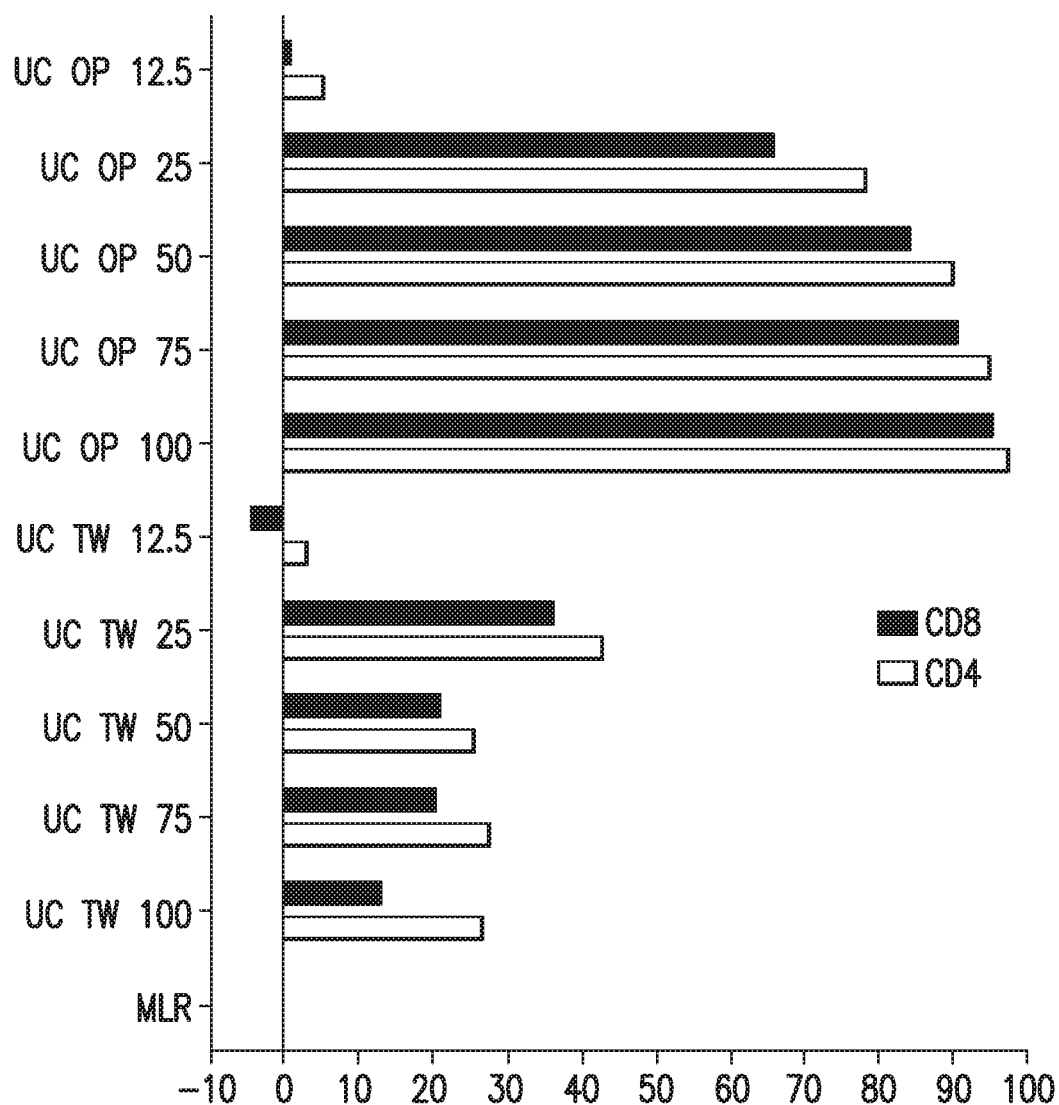

FIG. 17: Umbilical cord stroma stem cells (UC) added at 12,500 (UC OP/TW 12.5) to 100,000 (UC OP/TW 100) were either separated from the NLR by a membrane (TW) or in contact with the MLR (OP). Equal numbers of CD4+ T cells and CD8+ T cells were used, and the percentage suppression of the MLR (% CFSE$^{Low}$=89%) was calculated.

Figure 18:
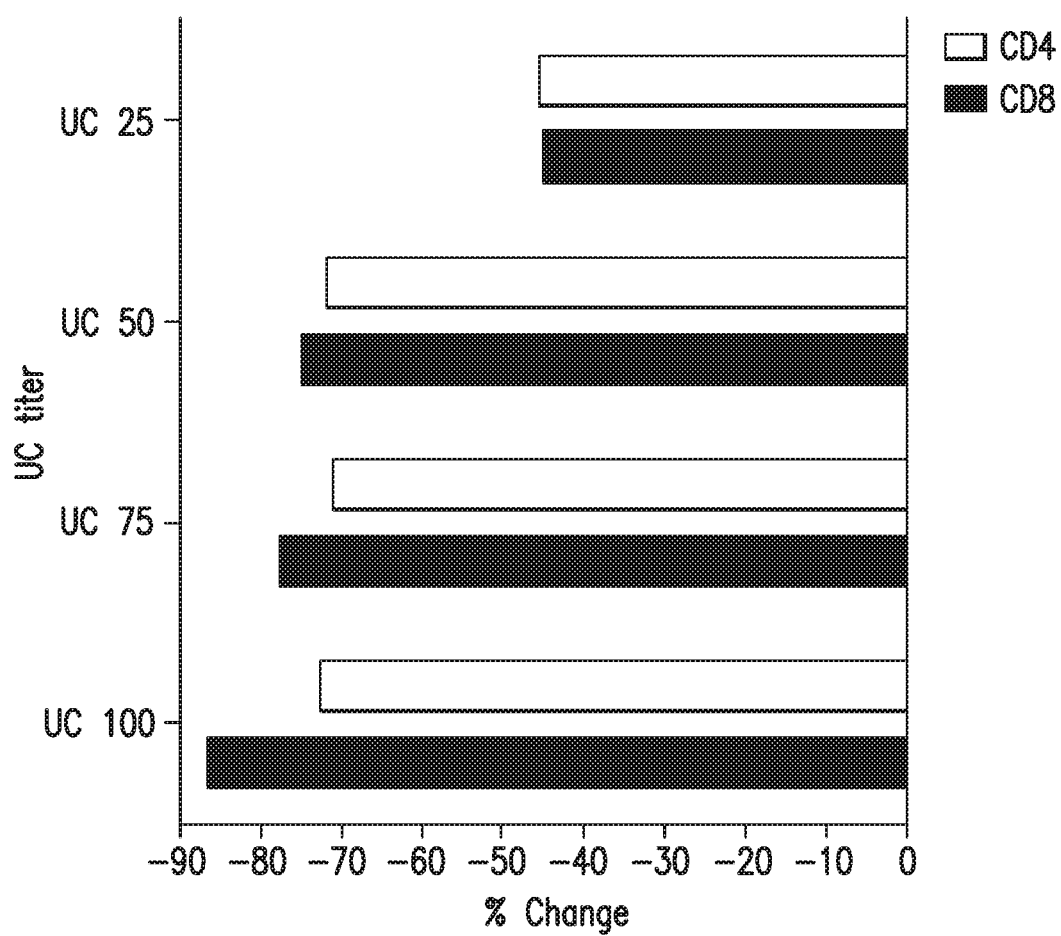

FIG. 18: The relationship between placental stem cell dose and cell to cell contact dependency is not linear. The changes in MLR suppression on introduction of the insert are calculated from the values given in FIG. 17.

Figure 19:
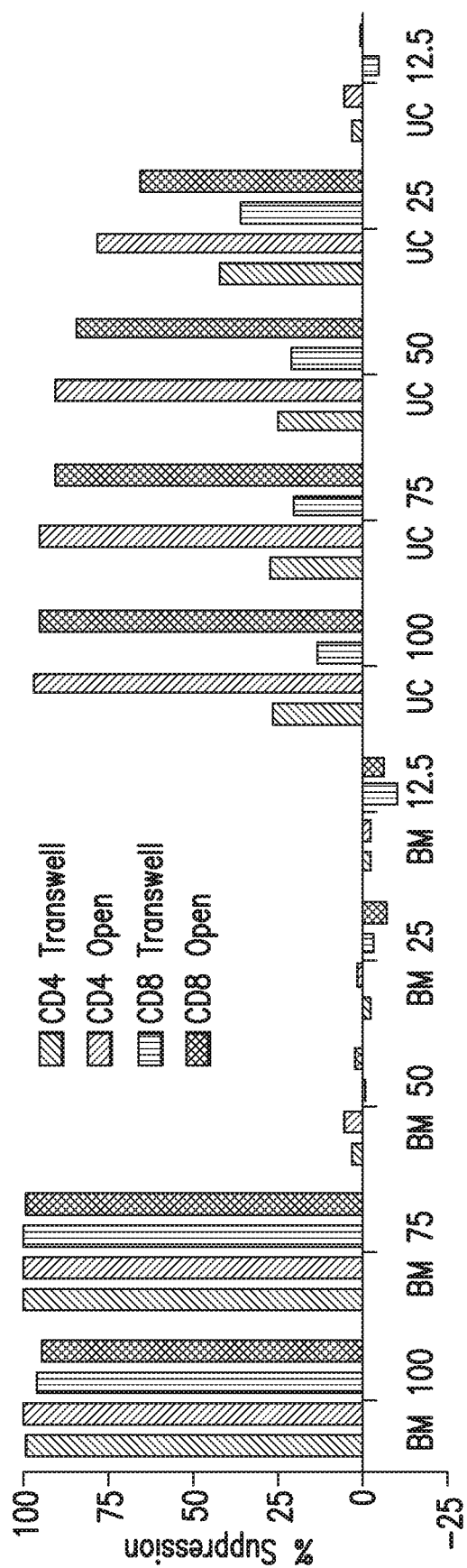

FIG. 19: Differential suppression of T cell responses by placental stem cells and BMSCs. The degree of suppression conferred by placental stem cells or BMSCs was calculated comparing the percentage of MLR T cells in the CFSE$^{Lo}$ gate, more than 70%, to that of the adherent cell MLRs. The MLR was either separated from the adherent cells (transwell), or was performed in an open well (open). The X axis gives the numbers of adherent cells, in thousands, added to 500,000 T cells and 50,000 DCs. The ratio of adherent cells to T cells goes from 1:5 to 1:40.

Figure 20:
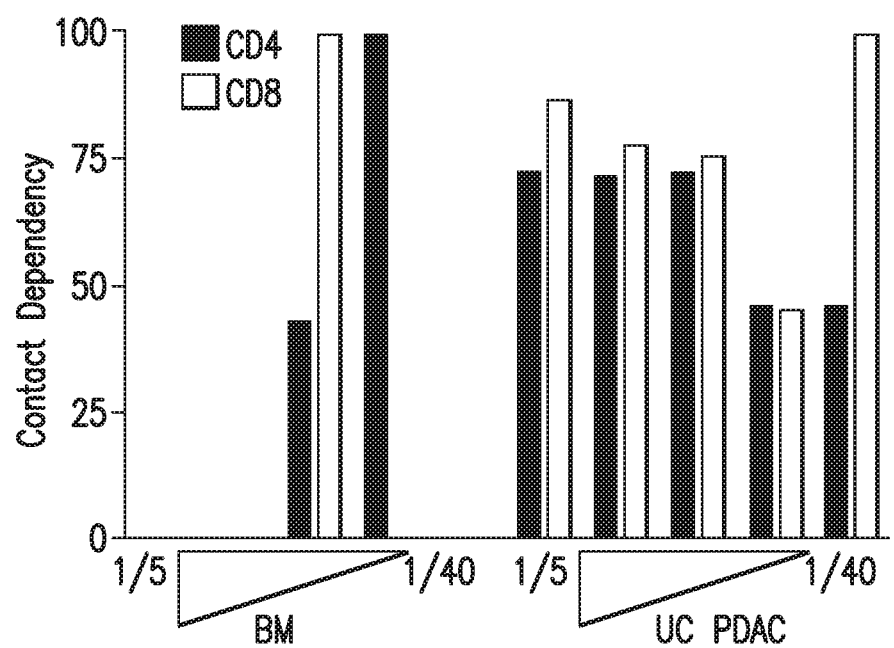

FIG. 20: Differential cell to cell contact requirements for placental stem cell and bone marrow-derived stem cell immune suppression. From the suppression data given in FIG. 15, the contact dependency was calculated and displayed against the adherent cell/T cell ratio (n=3, except UC: n=2).

Figure 21:
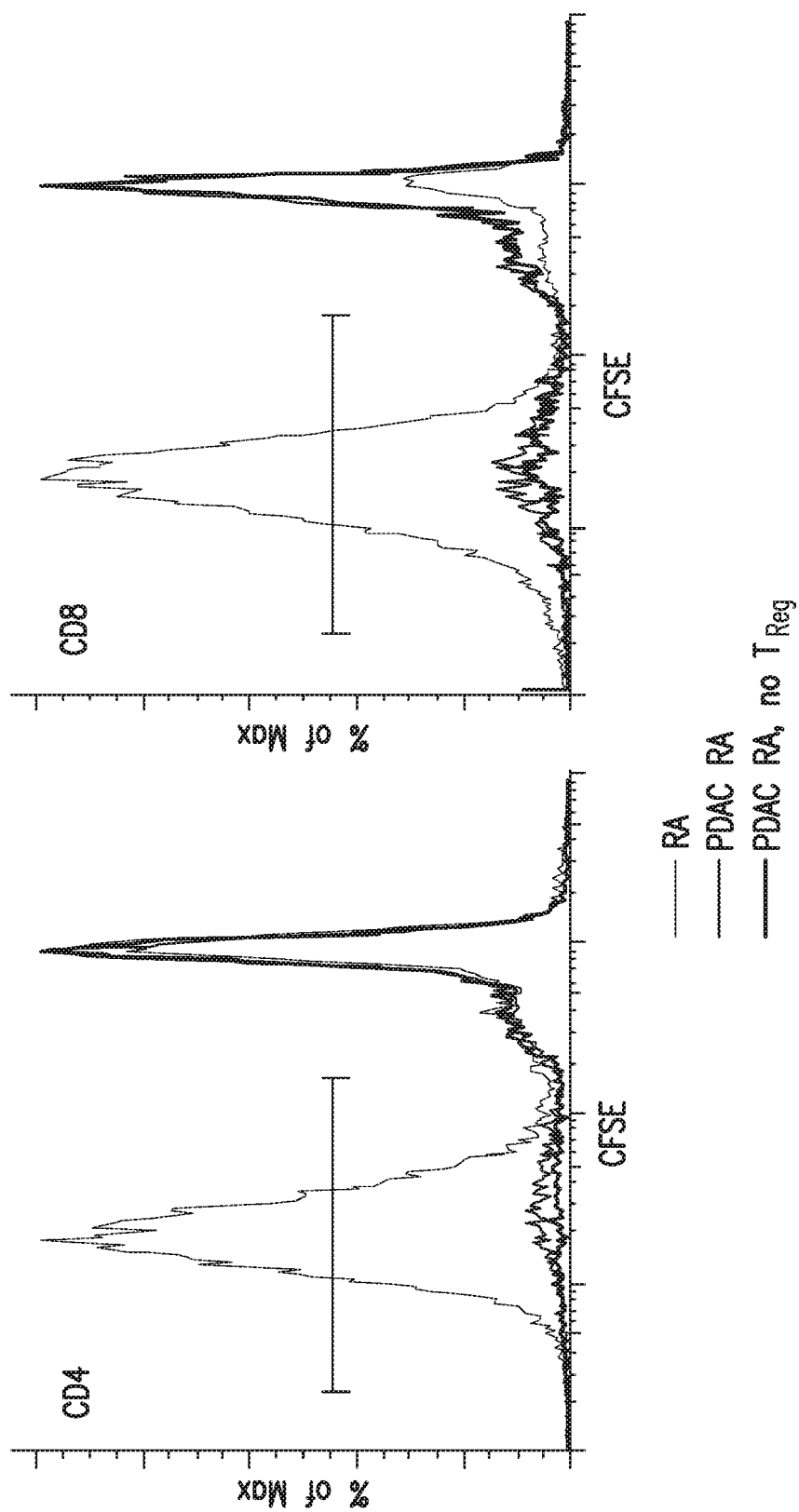

FIG. 21: T regulatory cells are not required for placental stem cell-mediated T cell suppression. A regression assay was performed using either whole PBMCs or PBMCs depleted of T regulatory cells, both CFSE stained, adding UC placental stem cells to some conditions. N=1.

Figure 22:
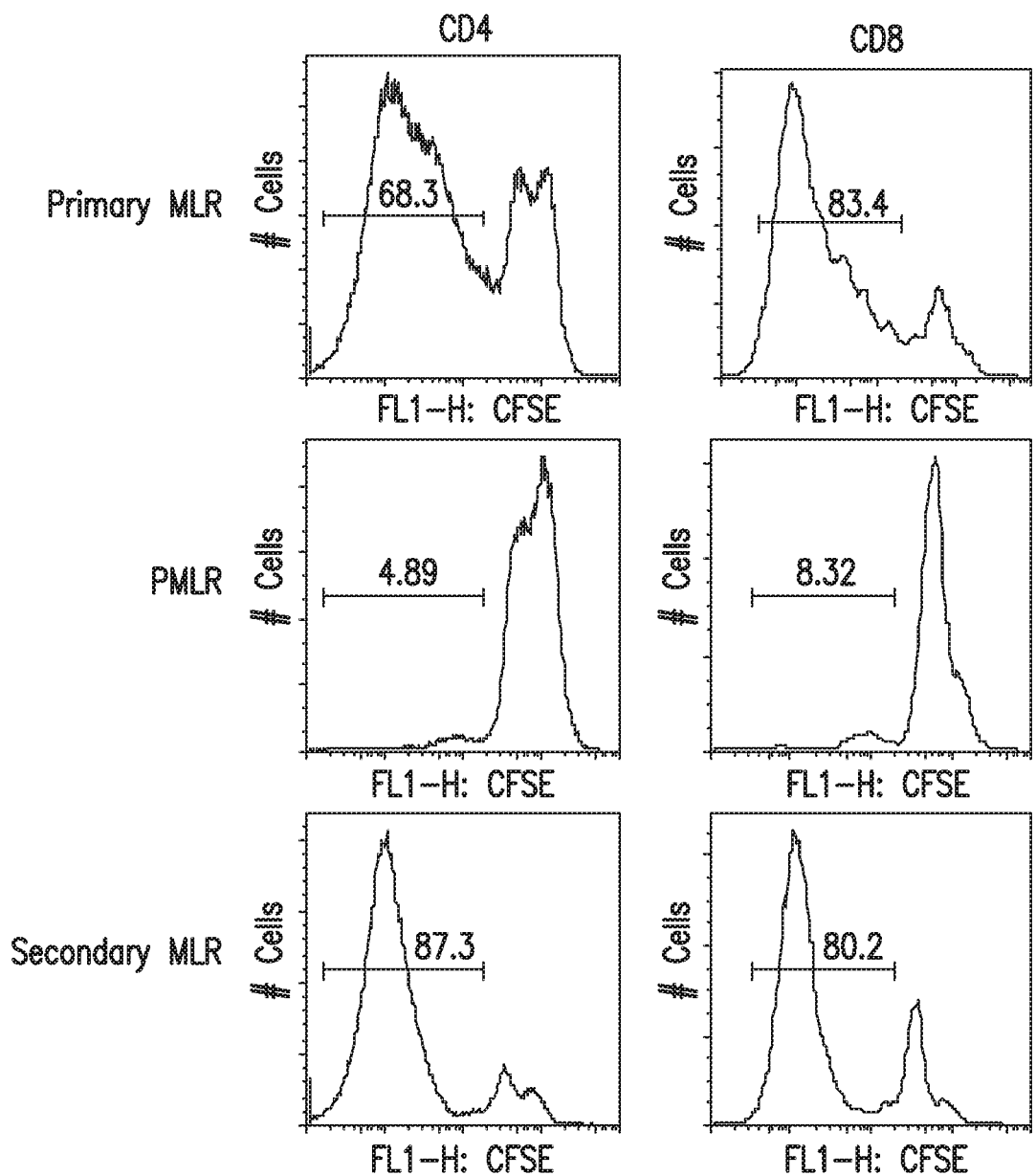

FIG. 22: CFSE$^{Hi}$ cells proliferate in a secondary MLR. From an placental stem cell MLR using CFSE stained cells, the CFSE$^{Hi}$ T cells were isolated on a FACS Aria. The cells were used in an MLR. N=1.

Figure 23:
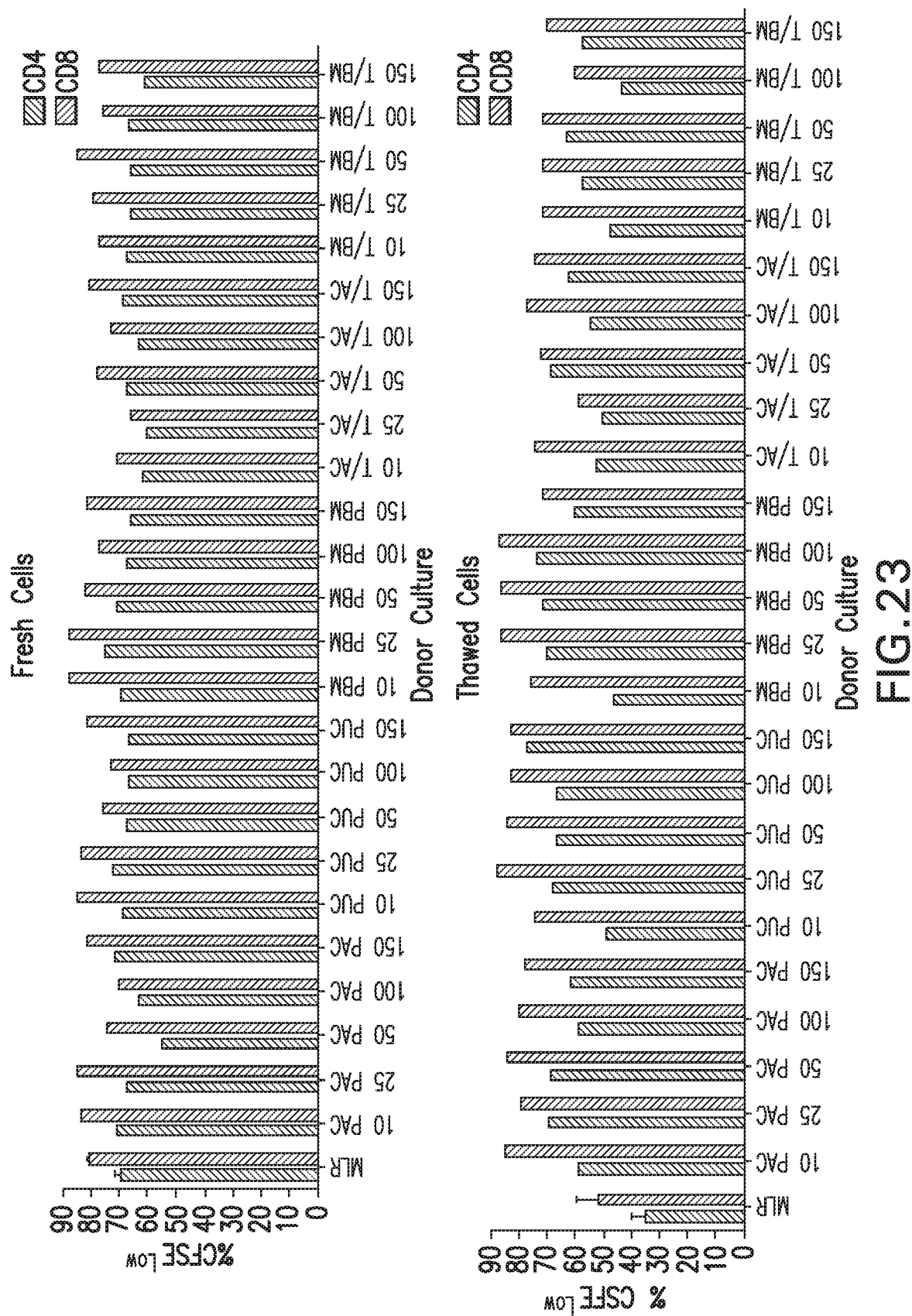

FIG. 23: Supernatant from suppressed stem cell MLR does not suppress MLR at 75% replacement. UC (PUC), AC (PAC), and BMSC (PBM) MLRs were performed, and all suppressed the MLR more than 50%. Supernatant from the experiments were used to replace from 10 to 150 µl of the 200 µl medium used for a fresh MLR. As controls, medium from T cell and AC (T/AC) or T cell and bone marrow-derived stem cell (T/BM) cocultures were also used in the same way (N=2).

Figure 24A:
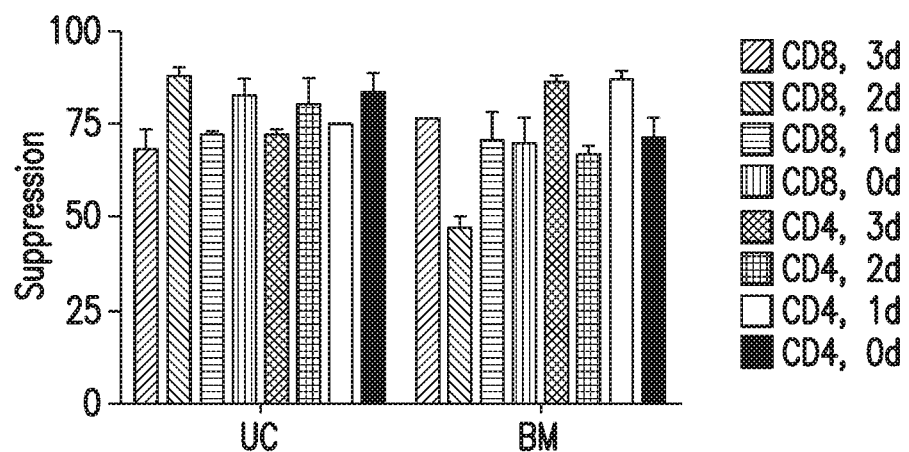
Figure 24B:
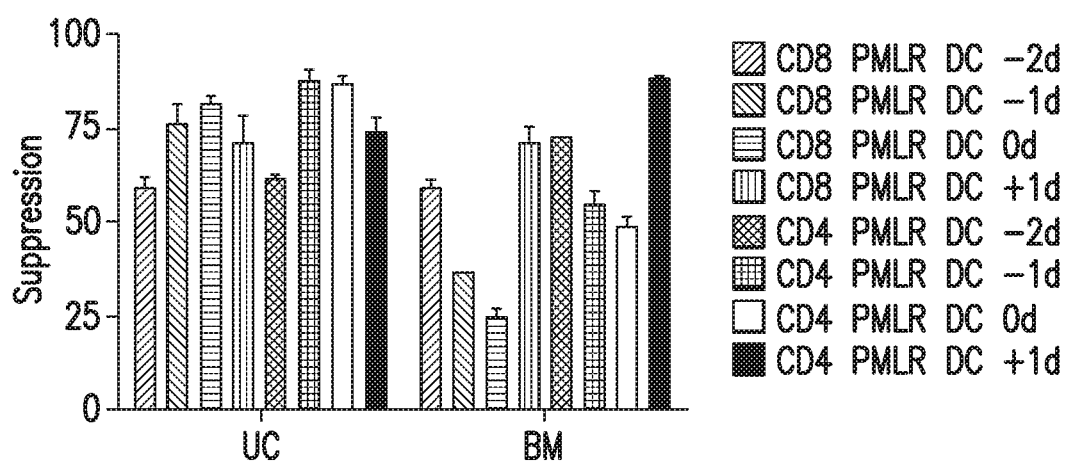

FIGS. 24A, 24B: Pre-incubating T cells and adherent cells does not influence MLR suppression. T cells from 2 donors were used in two independent experiments. Mature DCs (A) or CFSE stained CD3+ T cells (B) were incubated with umbilical cord stem cells (UC) or bone marrow-derived stem cells for the indicated number of days before adding DCs (on day 0, A) or CFSE CD3+ T cells (B, thereby starting the MLR. The adherent cell MLRs then proceeded for six days, as normal. N=2.

Figure 25A:
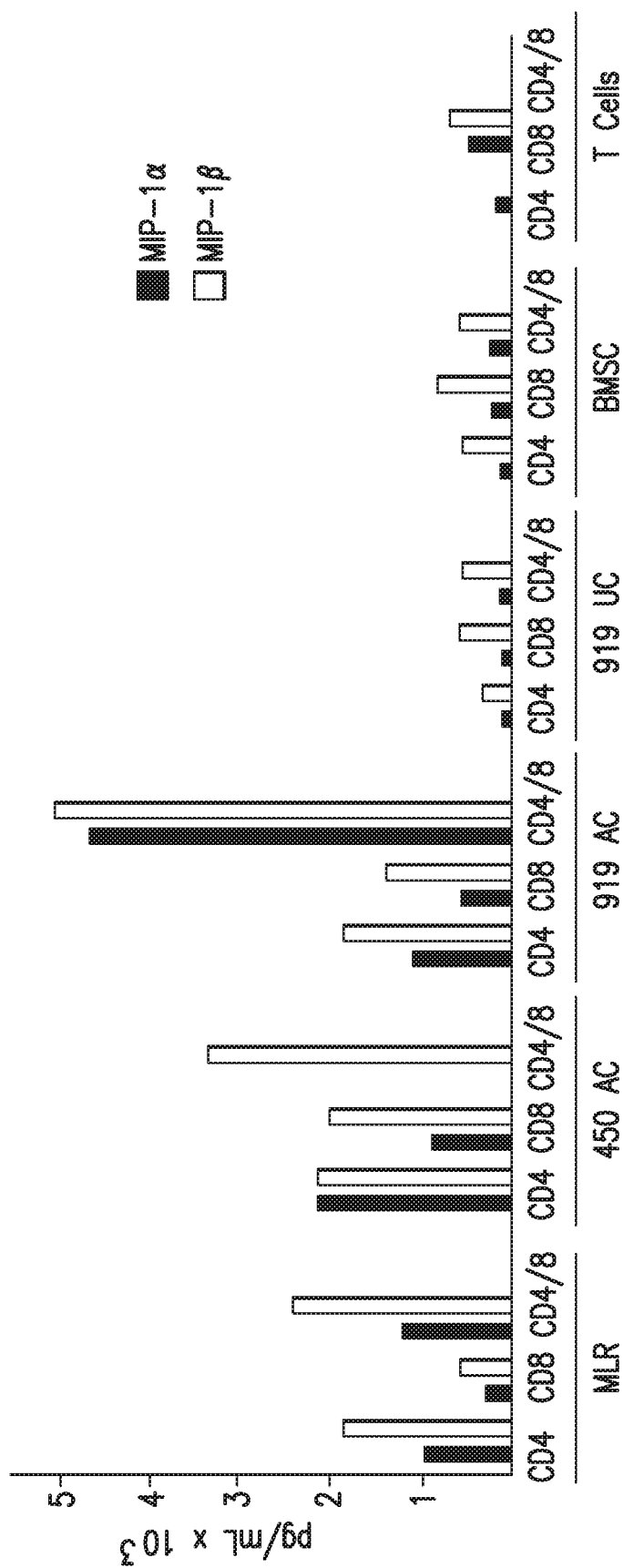
Figure 25B:
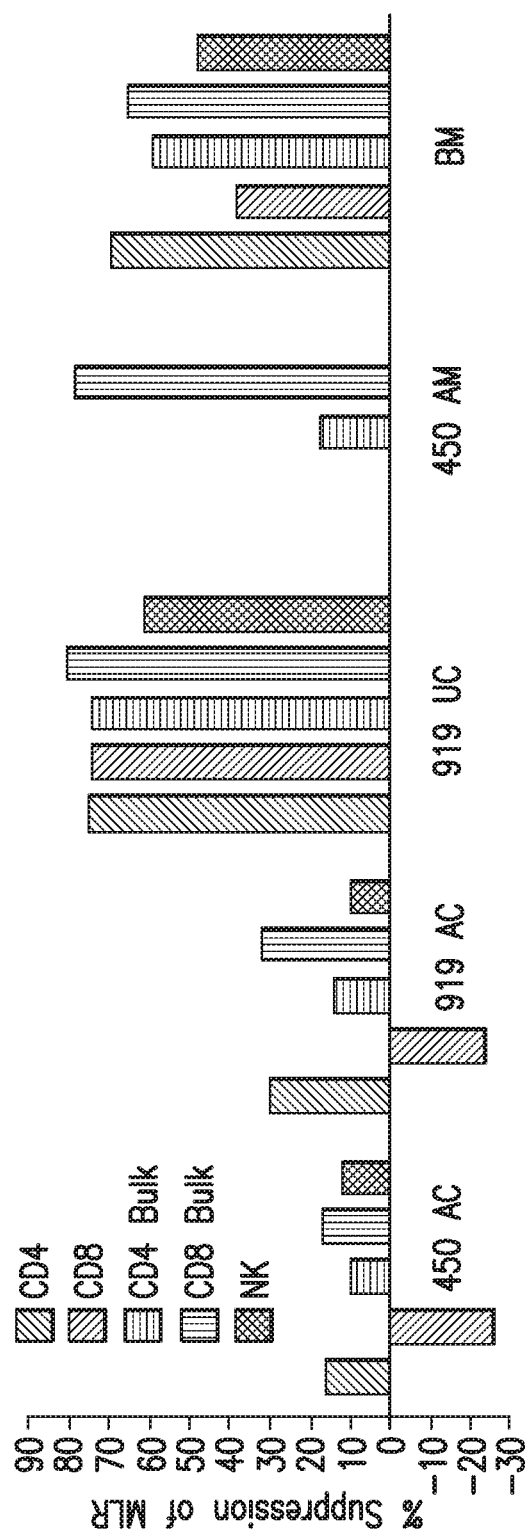

FIGS. 25A, 25B: A. MIP-1α and MIP-1β secretion in the MLR, and MLR with placental stem cells or bone marrow-derived stem cells, correlates inversely with MLR suppression. B: T cell and NK cell CFSE data from the same experiment. Supernatants were harvested from the MLR shown in FIG. 24B, and analyzed for MIP-1α and MIP-1β: MLR was performed as described, and on average 55% (T cells) or 83% (NK cells) CFSE$^{Low}$ cells were observed. The suppressive effect of stem cell addition was calculated. N=2 (NK part: N=1).

Figure 26:
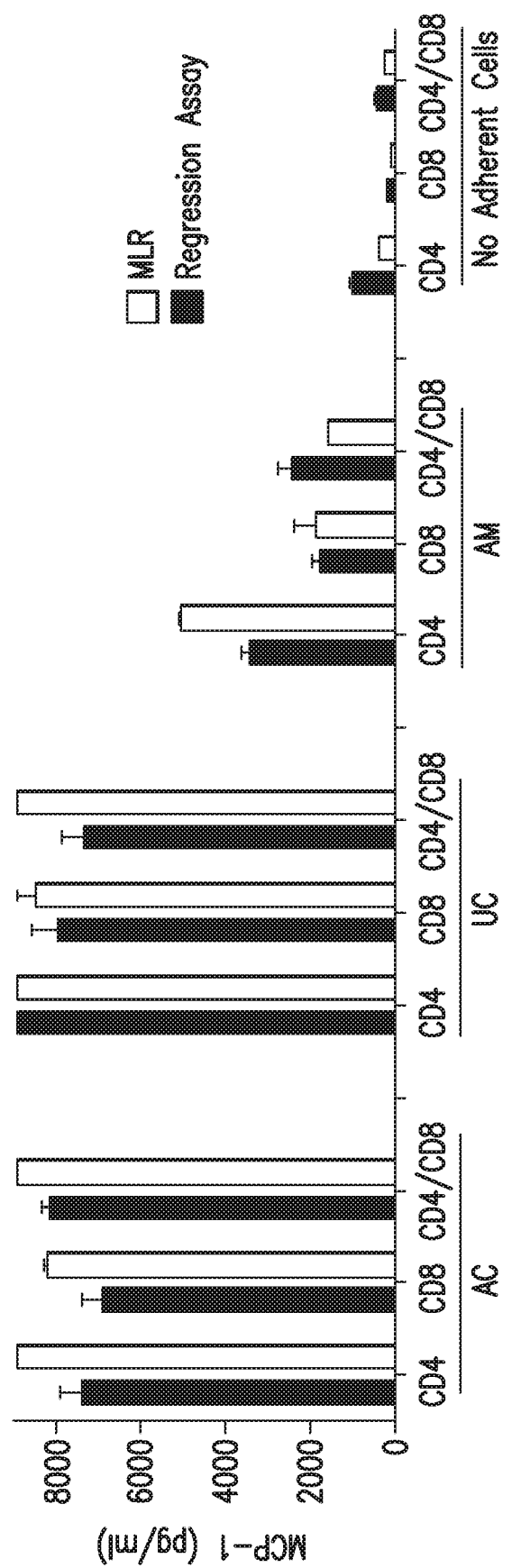

FIG. 26: In the modified regression assay and MLR supernatants, MCP-1 was measured. The placental stem cell suppression of the MLR and regression assay correlates with secretion of the chemoattractant MCP-1. AC: stem cells from amnion-chorion plate. UC: stem cells from umbilical cord. Light bars: MLR assay results. Dark bars: regression assay results. Y axis: pg of MCP-1 in assay solution.

Figure 27:
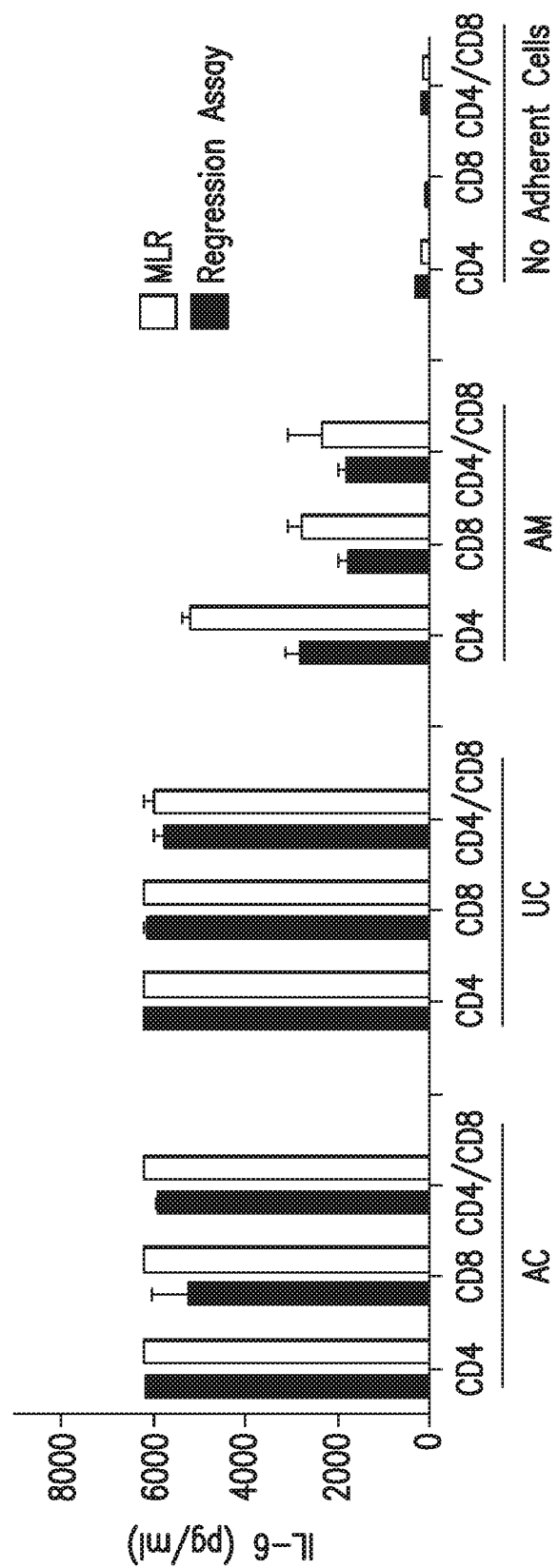

FIG. 27: IL-6 measurement in the supernatant of the modified MLR and regression assay. The placental stem cell suppression of the MLR and regression assay correlates with IL-6 secretion. AC: stem cells from amnion-chorion plate. UC: stem cells from umbilical cord. Light bars: MLR assay results. Dark bars: regression assay results. Y axis: pg of IL-6 in assay solution.

5. DETAILED DESCRIPTION

Provided herein are methods for the treatment of an individual having a disease, disorder or condition associated with, arising from, or related to an inappropriate, unwanted, harmful or deleterious immune response, e.g., an autoimmune disease, comprising administering to the individual having the disease, disorder or condition one or more doses of placental stem cells and/or umbilical cord stem cells. Methods for the treatment of such individuals, and for the administration of such stem cells, alone or in combination with other therapies, are discussed in detail below.

5.1 Immunomodulation Using Placental Stem Cells

Provided herein are methods for the modulation, e.g., suppression, of the activity, e.g., proliferation, of an immune cell, or plurality of immune cells, by contacting the immune cell(s) with a plurality of placental stem cells. Such immunomodulation is useful in the treatment of an individual having a disease, disorder or condition caused by, or relating to, an unwanted or harmful immune response, for example, inflammatory bowel disease, graft-versus-host disease, multiple sclerosis, rheumatoid arthritis, psoriasis, lupus erythematosus, diabetes, mycosis fungoides (Alibert-Bazin syndrome), or scleroderma. Such immunomodulation is also useful, e.g., in the reduction or elimination of a host immune response against allogenic tissue, e.g., a transplanted organ, composite tissue allograft, and the like.

In one embodiment, provided herein is a method of suppressing an immune response comprising contacting a plurality of immune cells with a plurality of placental stem cells for a time sufficient for said placental stem cells to detectably suppress an immune response, wherein said placental stem cells detectably suppress T cell proliferation in a mixed lymphocyte reaction (MLR) assay or a regression assay.

Placental stem cells are, e.g., the placental stem cells described elsewhere herein (see Section 5.2). Placental stem cells used for immunosuppression can be derived or obtained from a single placenta or multiple placentas. Placental stem cells used for immunosuppression can also be derived from a single species, e.g., the species of the intended recipient or the species of the immune cells the function of which is to be reduced or suppressed, or can be derived from multiple species.

An "immune cell" in the context of this method means any cell of the immune system, particularly T cells and NK (natural killer) cells. Thus, in various embodiments of the method, placental stem cells are contacted with a plurality of immune cells, wherein the plurality of immune cells are, or comprises, a plurality of T cells (e.g., a plurality of CD3$^+$ T cells, CD4$^+$ T cells and/or CD8$^+$ T cells) and/or natural killer cells. An "immune response" in the context of the method can be any response by an immune cell to a stimulus normally perceived by an immune cell, e.g., a response to the presence of an antigen. In various embodiments, an immune response can be the proliferation of T cells (e.g., CD3$^+$ T cells, CD4$^+$ T cells and/or CD8$^+$ T cells) in response to a foreign antigen, such as an antigen present in a transfusion or graft, or to a self-antigen, as in an autoimmune disease. The immune response can also be a proliferation of T cells contained within a graft. The immune response can also be any activity of a natural killer (NK) cell, the maturation of a dendritic cell, or the like. The immune response can also be a local, tissue- or organ-specific, or systemic effect of an activity of one or more classes of immune cells, e.g., the immune response can be graft versus host disease, inflammation, formation of inflammation-related scar tissue, an autoimmune condition (e.g., rheumatoid arthritis, Type I diabetes, lupus erythematosus, etc.). and the like.

"Contacting" in this context encompasses bringing the placental stem cells and immune cells together in a single container (e.g., culture dish, flask, vial, etc.) or in vivo, for example, the same individual (e.g., mammal, for example, human). In a preferred embodiment, the contacting is for a time sufficient, and with a sufficient number of placental stem cells and immune cells, that a change in an immune function of the immune cells is detectable. More preferably, in various embodiments, said contacting is sufficient to suppress immune function (e.g., T cell proliferation in response to an antigen) by at least 50%, 60%, 70%, 80%, 90% or 95%, compared to the immune function in the absence of the placental stem cells. Such suppression in an in vivo context can be determined in an in vitro assay (see below); that is, the degree of suppression in the in vitro assay can be extrapolated, for a particular number of placental stem cells and a number of immune cells in a recipient individual, to a degree of suppression in the individual.

In certain embodiments, provided herein are methods of using placental stem cells to modulate an immune response, or the activity of a plurality of one or more types of immune cells, in vitro. Contacting the placental stem cells and plurality of immune cells can comprise combining the placental stem cells and immune cells in the same physical space such that at least a portion of the plurality of placental stem cells interacts with at least a portion of the plurality of immune cells; maintaining the placental stem cells and immune cells in separate physical spaces with common medium; or can comprise contacting medium from one or a culture of placental stem cells or immune cells with the other type of cell (for example, obtaining culture medium from a culture of placental stem cells and resuspending isolated immune cells in the medium). In a specific example, the contacting is performed in a Mixed Lymphocyte Reaction (MLR). In another specific example, the contacting is performed in a regression assay.

Such contacting can, for example, take place in an experimental setting designed to determine the extent to which a particular plurality of placental stem cells is immunomodulatory, e.g., immunosuppressive. Such an experimental setting can be, for example, a mixed lymphocyte reaction (MLR) or regression assay. Procedures for performing the MLR and regression assays are well-known in the art. See, e.g. Schwarz, "The Mixed Lymphocyte Reaction: An In Vitro Test for Tolerance," *J. Exp. Med.* 127(5):879-890 (1968); Lacerda et al., "Human Epstein-Barr Virus (EBV)-Specific Cytotoxic T Lymphocytes Home Preferentially to and Induce Selective Regressions of Autologous EBV-Induced B Lymphoproliferations in Xenografted C.B-17 *Scid/Scid Mice,*" *J. Exp. Med.* 183:1215-1228 (1996). In a preferred embodiment, an MLR is performed in which a plurality of placental stem cells are contacted with a plurality of immune cells (e.g., lymphocytes, for example, $CD3^+$, $CD4^+$ and/or $CD8^+$ T lymphocytes).

The MLR can be used to determine the immunosuppressive capacity of a plurality of placental stem cells. For example, a plurality of placental stem cells can be tested in an MLR comprising combining $CD4^+$ or $CD8^+$ T cells, dendritic cells (DC) and placental stem cells in a ratio of about 10:1:2, wherein the T cells are stained with a dye such as, e.g., CFSE that partitions into daughter cells, and wherein the T cells are allowed to proliferate for about 6 days. The plurality of placental stem cells is immunosuppressive if the T cell proliferation at 6 days in the presence of placental stem cells is detectably reduced compared to T cell proliferation in the presence of DC and absence of placental stem cells. In such an MLR, placental stem cells are either thawed or harvested from culture. About 20,000 placental stem cells are resuspended in 100 µl of medium (RPMI 1640, 1 mM HEPES buffer, antibiotics, and 5% pooled human serum), and allowed to attach to the bottom of a well for 2 hours. $CD4^+$ and/or $CD8^+$ T cells are isolated from whole peripheral blood mononuclear cells Miltenyi magnetic beads. The cells are CFSE stained, and a total of 100,000 T cells ($CD4^+$ T cells alone, $CD8^+$ T cells alone, or equal amounts of $CD4^+$ and $CD8^+$ T cells) are added per well. The volume in the well is brought to 200 µl, and the MLR is allowed to proceed.

In one embodiment, therefore, provided herein is a method of suppressing an immune response comprising contacting a plurality of immune cells with a plurality of placental stem cells for a time sufficient for said placental stem cells to detectably suppress T cell proliferation in a mixed lymphocyte reaction (MLR) assay or in a regression assay. In one embodiment, said placental stem cells used in the MLR represent a sample or aliquot of placental stem cells from a larger population of placental stem cells.

Populations of placental stem cells obtained from different placentas, or different tissues within the same placenta, can differ in their ability to modulate an activity of an immune cell, e.g., can differ in their ability to suppress T cell activity or proliferation or NK cell activity. It is thus desirable to determine, prior to use, the capacity of a particular population of placental stem cells for immunosuppression. Such a capacity can be determined, for example, by testing a sample of the placental stem cell population in an MLR or regression assay. In one embodiment, an MLR is performed with the sample, and a degree of immunosuppression in the assay attributable to the placental stem cells is determined. This degree of immunosuppression can then be attributed to the placental stem cell population that was sampled. Thus, the MLR can be used as a method of determining the absolute and relative ability of a particular population of placental stem cells to suppress immune function. The parameters of the MLR can be varied to provide more data or to best determine the capacity of a sample of placental stem cells to immunosuppress. For example, because immunosuppression by placental stem cells appears to increase roughly in proportion to the number of placental stem cells present in the assay, the MLR can be performed with, in one embodiment, two or more numbers of placental stem cells, e.g., $1\times10^3$, $3\times10^3$, $1\times10^4$ and/or $3\times10^4$ placental stem cells per reaction. The number of placental stem cells relative to the number of T cells in the assay can also be varied. For example, placental stem cells and T cells in the assay can be present in any ratio of, e.g. about 10:1 to about 1:10, preferably about 1:5, though a relatively greater number of placental stem cells or T cells can be used.

The regression assay can be used in similar fashion.

Provided herein are methods of using placental stem cells to modulate an immune response, or the activity of a plurality of one or more types of immune cells, in vivo. Placental stem cells and immune cells can be contacted, e.g., in an individual that is a recipient of a plurality of placental stem cells. Where the contacting is performed in an individual, in one embodiment, the contacting is between exogenous placental stem cells (that is, placental stem cells not derived from the individual) and a plurality of immune cells endogenous to the individual. In specific embodiments, the immune cells within the individual are $CD3^+$ T cells, $CD4^+$ T cells, $CD8^+$ T cells, and/or NK cells.

Such immunosuppression using placental stem cells would be advantageous for any condition caused or worsened by, or related to, an inappropriate or undesirable immune response. Placental stem cell-mediated immunomodulation, e.g., immunosuppression, would, for example, be useful in the suppression of an inappropriate immune response raised by the individual's immune system against one or more of its own tissues. In various embodiments, therefore, provided herein is a method of suppressing an immune response, wherein the immune response is an autoimmune disease, e.g., lupus erythematosus, diabetes, rheumatoid arthritis, or multiple sclerosis.

The contacting of the plurality of placental stem cells with the plurality of one or more types of immune cells can occur in vivo in the context of, or as an adjunct to, for example, grafting or transplanting of one or more types of tissues to a recipient individual. Such tissues may be, for example, bone marrow or blood; an organ; a specific tissue (e.g., skin graft); composite tissue allograft (i.e., a graft comprising two or more different types of tissues); etc. In this regard, the placental stem cells can be used to suppress one or more immune responses of one or more immune cells contained within the recipient individual, within the transplanted tissue or graft, or both. The contacting can occur before, during and/or after the grafting or transplanting. For example, placental stem cells can be administered at the time of the transplant or graft. The placental stem cells can also, or alternatively, be administered prior to the transplanting or grafting, e.g., about 1, 2, 3, 4, 5, 6 or 7 days prior to the transplanting or grafting. Placental stem cells can also, or alternatively, be administered to a transplant or graft recipient after the transplantation or grafting, for example, about 1, 2, 3, 4, 5, 6 or 7 days after the transplanting or grafting. Preferably, the plurality of placental stem cells are contacted with the plurality of placental stem cells before any detectable sign or symptom of an immune response, either by the recipient individual or the transplanted tissue or graft, e.g., a detectable sign or symptom of graft-versus-host disease or detectable inflammation, is detectable.

In another embodiment, the contacting within an individual is primarily between exogenous placental stem cells and exogenous progenitor cells or stem cells, e.g., exogenous progenitor cells or stem cells that differentiate into immune cells. For example, individuals undergoing partial or full immunoablation or myeloablation as an adjunct to cancer therapy can receive placental stem cells in combination with one or more other types of stem or progenitor cells. For example, the placental stem cells can be combined with a plurality of CD34+ cells, e.g., CD34+ hematopoietic stem cells. Such CD34+ cells can be, e.g., CD34+ cells from a tissue source such as peripheral blood, umbilical cord blood, placental blood, or bone marrow. The CD34+ cells can be isolated from such tissue sources, or the whole tissue source (e.g., units of umbilical cord blood or bone marrow) or a partially purified preparation from the tissue source (e.g., white blood cells from cord blood) can be combined with the placental stem cells. Combinations of placental stem cells and cord blood, or stem cells from cord blood, are described in Hariri, U.S. Application Publication No. 2003/0180269.

The placental stem cells can be administered to the individual in a ratio, with respect to the known or expected number of immune cells, e.g., T cells, in the individual, of from about 10:1 to about 1:10, preferably about 1:5. However, a plurality of placental stem cells can be administered to an individual in a ratio of, in non-limiting examples, about 10,000:1, about 1,000:1, about 100:1, about 10:1, about 1:1, about 1:10, about 1:100, about 1:1,000 or about 1:10,000. Generally, about $1\times10^5$ to about $1\times10^8$ placental stem cells per recipient kilogram, preferably about $1\times10^6$ to about $1\times10^7$ placental stem per recipient kilogram can be administered to effect immunosuppression. In various embodiments, a plurality of placental stem cells administered to an individual or subject comprises at least, about, or no more than, $1\times10^5$, $3\times10^5$, $1\times10^6$, $3\times10^6$, $1\times10^7$, $3\times10^7$, $1\times10^8$, $3\times10^8$, $1\times10^9$, $3\times10^9$ placental stem cells, or more.

The placental stem cells can also be administered with one or more second types of stem cells, e.g., mesenchymal stem cells from bone marrow. Such second stem cells can be administered to an individual with placental stem cells in a ratio of, e.g., about 1:10 to about 10:1.

To facilitate contacting the placental stem cells and immune cells in vivo, the placental stem cells can be administered to the individual by any route sufficient to bring the placental stem cells and immune cells into contact with each other. For example, the placental stem cells can be administered to the individual, e.g., intravenously, intramuscularly, intraperitoneally, intraocularly, parenterally, or directly into an organ, e.g., pancreas. For in vivo administration, the placental stem cells can be formulated as a pharmaceutical composition, as described in Section 5.6.1, below.

The method of immunosuppression can additionally comprise the addition of one or more immunosuppressive agents, particularly in the in vivo context. In one embodiment, the plurality of placental stem cells are contacted with the plurality of immune cells in vivo in an individual, and a composition comprising an immunosuppressive agent is administered to the individual. Immunosuppressive agents are well-known in the art and include, e.g., anti-T cell receptor antibodies (monoclonal or polyclonal, or antibody fragments or derivatives thereof), anti-IL-2 receptor antibodies (e.g., Basiliximab (SIMULECT®) or daclizumab (ZENAPAX)®), anti T cell receptor antibodies (e.g., Muromonab-CD3), azathioprine, corticosteroids, cyclosporine, tacrolimus, mycophenolate mofetil, sirolimus, calcineurin inhibitors, and the like. In a specific embodiment, the immunosuppressive agent is a neutralizing antibody to macrophage inflammatory protein (MIP)-1α or MIP-1β. Preferably, the anti-MIP-1α or MIP-1β antibody is administered in an amount sufficient to cause a detectable reduction in the amount of MIP-1α and/or MIP-1β in said individual, e.g., at the time of transplanting.

5.2 Placental Stem Cells and Placental Stem Cell Populations

The methods of immunosuppression provided herein use placental stem cells, that is, stem cells obtainable from a placenta or part thereof, that (1) adhere to a tissue culture substrate; (2) have the capacity to differentiate into non-placental cell types; and (3) have, in sufficient numbers, the capacity to detectably suppress an immune function, e.g., proliferation of CD4+ and/or CD8+ T cells in a mixed lymphocyte reaction assay or regression assay. Placental stem cells are not derived from blood, e.g., placental blood or umbilical cord blood. The placental stem cells used in the methods and compositions provided herein have the capacity, and are selected for their capacity, to suppress the immune system of an individual.

Placental stem cells can be either fetal or maternal in origin (that is, can have the genotype of either the mother or fetus). Populations of placental stem cells, or populations of cells comprising placental stem cells, can comprise placental stem cells that are solely fetal or maternal in origin, or can comprise a mixed population of placental stem cells of both fetal and maternal origin. The placental stem cells, and populations of cells comprising the placental stem cells, can be identified and selected by the morphological, marker, and culture characteristics discussed below.

5.2.1 Physical and Morphological Characteristics

The placental stem cells used as described herein, when cultured in primary cultures or in cell culture, adhere to the tissue culture substrate, e.g., tissue culture container surface (e.g., tissue culture plastic). Placental stem cells in culture assume a generally fibroblastoid, stellate appearance, with a number of cytoplasmic processes extending from the central cell body. The placental stem cells are, however, morphologically differentiable from fibroblasts cultured under the same conditions, as the placental stem cells exhibit a greater number of such processes than do fibroblasts. Morphologically, placental stem cells are also differentiable from hematopoietic stem cells, which generally assume a more rounded, or cobblestone, morphology in culture.

5.2.2 Cell Surface, Molecular and Genetic Markers

Placental stem cells, and populations of placental stem cells, useful in the methods and compositions provided herein, express a plurality of markers that can be used to identify and/or isolate the stem cells, or populations of cells that comprise the stem cells. The placental stem cells, and stem cell populations (that is, two or more placental stem cells) include stem cells and stem cell-containing cell populations obtained directly from the placenta, or any part thereof (e.g., amnion, chorion, placental cotyledons, and the like). Placental stem cell populations also includes populations of (that is, two or more) placental stem cells in culture, and a population in a container, e.g., a bag. Placental stem cells are not, however, trophoblasts.

Placental stem cells generally express the markers CD73, CD105, CD200, HLA-G, and/or OCT-4, and do not express CD34, CD38, or CD45. Placental stem cells can also express HLA-ABC (MHC-1) and HLA-DR. These markers can be used to identify placental stem cells, and to distinguish placental stem cells from other stem cell types. Because the placental stem cells can express CD73 and CD105, they can have mesenchymal stem cell-like characteristics. However, because the placental stem cells can express CD200 and HLA-G, a fetal-specific marker, they can be distinguished from mesenchymal stem cells, e.g., bone marrow-derived mesenchymal stem cells, which express neither CD200 nor HLA-G. In the same manner, the lack of expression of CD34, CD38 and/or CD45 identifies the placental stem cells as non-hematopoietic stem cells.

In one embodiment, provided herein is an isolated cell population comprising a plurality of immunosuppressive placental stem cells that are $CD200^+$, $HLA-G^+$, wherein said plurality detectably suppresses T cell proliferation in a mixed lymphocyte reaction (MLR) assay. In a specific embodiment of the isolated populations, said stem cells are also $CD73^+$ and $CD105^+$. In another specific embodiment, said stem cells are also $CD34^-$, $CD38^-$ or $CD45^-$. In a more specific embodiment, said stem cells are also $CD34^-$, $CD38^-$, $CD45^-$, $CD73^+$ and $CD105^+$. In another embodiment, said isolated population produces one or more embryoid-like bodies when cultured under conditions that allow the formation of embryoid-like bodies.

In another embodiment, provided herein is an isolated cell population comprising a plurality of immunosuppressive placental stem cells that are $CD73^+$, $CD105^+$, $CD200^+$, wherein said plurality detectably suppress T cell proliferation in a mixed lymphocyte reaction (MLR) assay. In a specific embodiment of said populations, said stem cells are $HLA-G^+$. In another specific embodiment, said stem cells are $CD34^-$, $CD38^-$ or $CD45^-$. In another specific embodiment, said stem cells are $CD34^-$, $CD38^-$ and $CD45^-$. In a more specific embodiment, said stem cells are $CD34^-$, $CD38^-$, $CD45^-$, and $HLA-G^+$. In another specific embodiment, said population of cells produces one or more embryoid-like bodies when cultured under conditions that allow the formation of embryoid-like bodies.

An isolated cell population useful in the compositions and methods provided herein can comprise a plurality of immunosuppressive placental stem cells that are $CD200^+$, $OCT-4^+$, wherein said plurality detectably suppresses T cell proliferation in a mixed lymphocyte reaction (MLR) assay. In a specific embodiment, said stem cells are $CD73^+$ and $CD105^+$. In another specific embodiment, said stem cells are $HLA-G^+$. In another specific embodiment, said stem cells are $CD34^-$, $CD38^-$ and $CD45^-$. In a more specific embodiment, said stem cells are $CD34^-$, $CD38^-$, $CD45^-$, $CD73^+$, $CD105^+$ and $HLA-G^+$. In another specific embodiment, the population produces one or more embryoid-like bodies when cultured under conditions that allow the formation of embryoid-like bodies.

Also provided herein is an isolated cell population comprising a plurality of immunosuppressive placental stem cells that are $CD73^+$, $CD105^+$ and $HLA-G^+$, wherein said plurality detectably suppresses T cell proliferation in a mixed lymphocyte reaction (MLR) assay. In a specific embodiment of the above plurality, said stem cells are also $CD34^-$, $CD38^-$ or $CD45^-$. In another specific embodiment, said stem cells are also $CD34^-$, $CD38^-$ and $CD45^-$. In another specific embodiment, said stem cells are also $OCT-4^+$. In another specific embodiment, said stem cells are also $CD200^+$ In a more specific embodiment, said stem cells are also $CD34^-$, $CD38^-$, $CD45^-$, $OCT-4^+$ and $CD200^+$.

Further provided herein is an isolated cell population comprising a plurality of immunosuppressive placental stem cells that are $CD73^+$, $CD105^+$ stem cells, wherein said plurality forms one or more embryoid-like bodies under conditions that allow formation of embryoid-like bodies, and wherein said plurality detectably suppresses T cell proliferation in a mixed lymphocyte reaction (MLR) assay. In a specific embodiment, said stem cells are also $CD34^-$, $CD38^-$ or $CD45^-$. In another specific embodiment, said stem cells are also $CD34^-$, $CD38^-$ and $CD45^-$. In another specific embodiment, said stem cells are also $OCT-4^+$. In a more specific embodiment, said stem cells are also $OCT-4^+$, $CD34^-$, $CD38^-$ and $CD45^-$.

Also provided herein is an isolated cell population comprising a plurality of immunosuppressive placental stem cells that are $OCT-4^+$ stem cells, wherein said population forms one or more embryoid-like bodies when cultured under conditions that allow the formation of embryoid-like bodies, and wherein said plurality detectably suppresses T cell proliferation in a mixed lymphocyte reaction (MLR) assay. In various embodiments, at least 10%, at least 20%, at least 30%, at least 40%, at least 50% at least 60%, at least 70%, at least 80%, at least 90%, or at least 95% of said isolated placental cells are $OCT4^+$ stem cells. In a specific embodiment of the above populations, said stem cells are $CD73^+$ and $CD105^+$. In another specific embodiment, said stem cells are $CD34^-$, $CD38^-$, or $CD45^-$ In another specific embodiment, said stem cells are $CD200^+$. In a more specific embodiment, said stem cells are $CD73^+$, $CD105^+$, $CD200^+$, $CD34^-$, $CD38^-$, and $CD45^-$. In another specific embodiment, said population has been expanded, for example, passaged at least once, at least three times, at least five times, at least 10 times, at least 15 times, or at least 20 times.

The immunosuppressive placental stem cells provided herein include isolated placental stem cells, populations of isolated placental stem cells, or isolated populations of cells comprising placental stem cells, wherein the placental stem cells are $CD10^+$, $CD34^-$, $CD105^+$ and $CD200^+$.

Provided herein also is an isolated cell population comprising a plurality of immunosuppressive placental stem cells that are $CD29^+$, $CD44^+$, $CD73^+$, $CD90^+$, $CD105^+$, $CD200^+$, $CD34^-$ and $CD133^-$.

In another embodiment, stem cells useful in the compositions and methods provided herein are isolated placental stem cell that is $HLA-A,B,C^-$, $CD45^-$, $CD133^-$ and $CD34^-$. Further provided herein is an isolated population of placental stem cells, wherein at least about 70%, at least about 80%, at least about 90%, at least about 95% or at least about 99% of said placental stem cells are $HLA-A,B,C^-$, $CD45^-$, $CD133^-$ and $CD34^-$. In a specific embodiment, said stem cell or population of placental stem cells is isolated away from placental cells that are not stem cells. In another specific embodiment, said population of placental stem cells is isolated away from placental stem cells that do not display these characteristics. In another specific embodiment, said isolated placental stem cell is non-maternal in origin. In another specific embodiment, at least about 90%, at least about 95%, or at least about 99% of said cells in said isolated population of placental stem cells, are non-maternal in origin. In another embodiment, provided herein is a method of obtaining a placental stem cell that is $HLA-A,B,C^-$, $CD45^-$, $CD133^-$ and $CD34^-$ comprising isolating said cell from placental perfusate.

In another embodiment, provided herein is an isolated placental stem cell that is $CD10^+$, $CD13^+$, $CD33^+$, $CD45^-$, $CD117^-$ and $CD133^-$. Further provided herein is an isolated population of placental stem cells, wherein at least about 70%, at least about 80%, at least about 90%, at least about 95% or at least about 99% of said placental stem cells are $CD10^+$, $CD13^+$, $CD33^+$, $CD45^-$, $CD117^-$ and $CD133^-$. In a specific embodiment, said stem cell or population of placental stem cells is isolated away from placental cells that are not stem cells. In another specific embodiment, said isolated placental stem cell is non-maternal in origin. In another specific embodiment, at least about 90%, at least about 95%, or at least about 99% of said cells in said isolated population of placental stem cells, are non-maternal in origin. In another specific embodiment, said stem cell or population of placental stem cells is isolated away from placental stem cells that do not display these characteristics. In another embodiment, provided herein is a method of obtaining a placental stem cell that is CD10$^+$, CD13$^+$, CD33$^+$, CD45$^-$, CD117$^-$ and CD133$^-$ comprising isolating said cell from placental perfusate.

In another embodiment, provided herein is an isolated placental stem cell that is CD10$^-$, CD33$^-$, CD44$^+$, CD45$^-$, and CD117$^-$. Also provided herein is an isolated population of placental stem cells, wherein at least about 70%, at least about 80%, at least about 90%, at least about 95% or at least about 99% of said placental stem cells are CD10$^-$, CD33$^-$, CD44$^+$, CD45$^-$, and CD117$^-$. In a specific embodiment, said stem cell or population of placental stem cells is isolated away from placental cells that are not stem cells. In another specific embodiment, said isolated placental stem cell is non-maternal in origin. In another specific embodiment, at least about 90%, at least about 95%, or at least 99% of said cells in said isolated population of placental stem cells, are non-maternal in origin. In another specific embodiment, said stem cell or population of placental stem cells is isolated away from placental stem cells that do not display these characteristics. In another embodiment, provided herein is a method of obtaining a placental stem cell that is CD10$^-$, CD33$^-$, CD44$^+$, CD45$^-$, CD117$^-$ comprising isolating said cell from placental perfusate.

In another embodiment, provided herein is an isolated placental stem cell that is CD10$^-$, CD13$^-$, CD33$^-$, CD45$^-$, and CD117$^-$. Further provided is an isolated population of placental stem cells, wherein at least about 70%, at least about 80%, at least about 90%, at least about 95% or at least about 99% of said placental stem cells are CD10$^-$, CD13$^-$, CD33$^-$, CD45$^-$, and CD117$^-$. In a specific embodiment, said stem cell or population of placental stem cells is isolated away from placental cells that are not stem cells. In another specific embodiment, said isolated placental stem cell is non-maternal in origin. In another specific embodiment, at least about 90%, at least about 95%, or at least 99% of said cells in said isolated population of placental stem cells, are non-maternal in origin. In another specific embodiment, said stem cell or population of placental stem cells is isolated away from placental stem cells that do not display these characteristics. In another embodiment, also provided herein is a method of obtaining a placental stem cell that is CD10$^-$, CD13$^-$, CD33$^-$, CD45$^-$, and CD117$^-$ comprising isolating said cell from placental perfusate.

In another embodiment, provided herein is an isolated placental stem cell that is HLA A,B,C$^-$, CD45$^-$, CD34$^-$, CD133$^-$, positive for CD10, CD13, CD38, CD44, CD90, CD105, CD200 and/or HLA-G, and/or negative for CD117. Also provided herein is an isolated population of placental stem cells, wherein said stem cells are HLA A,B,C$^-$, CD45$^-$, CD34$^-$, CD133$^-$, and at least about 20%, 25%, 30%, 35%, 40%, 45%, 50%, 55%, 60%, 65%, 70%, 75%, 80%, 85%, 90%, 95%, 98% or about 99% of the stem cells in the population are positive for CD10, CD13, CD38, CD44, CD90, CD105, CD200 and/or HLA-G, and/or negative for CD117. In a specific embodiment, said stem cell or population of placental stem cells is isolated away from placental cells that are not stem cells. In another specific embodiment, said isolated placental stem cell is non-maternal in origin. In another specific embodiment, at least about 90%, at least about 95%, or at least about 99%, of said cells in said isolated population of placental stem cells, are non-maternal in origin. In another specific embodiment, said stem cell or population of placental stem cells is isolated away from placental stem cells that do not display these characteristics. In another embodiment, provided herein is a method of obtaining a placental stem cell that is HLA A,B,C$^-$, CD45$^-$, CD34$^-$, CD133$^-$ and positive for CD10, CD13, CD38, CD44, CD90, CD105, CD200 and/or HLA-G, and/or negative for CD117, comprising isolating said cell from placental perfusate.

In another embodiment, provided herein is a placental stem cell that is CD200$^+$ and CD10$^+$, as determined by antibody binding, and CD117$^-$, as determined by both antibody binding and RT-PCR. In another embodiment, provided herein is a placental stem cell that is CD10$^+$, CD29$^-$, CD54$^+$, CD200$^+$, HLA-G$^+$, HLA class I$^-$ and β-2-microglobulin$^-$. In another embodiment, provided herein are placental stem cells, wherein the expression of at least one marker is at least two-fold higher than for a mesenchymal stem cell (e.g., a bone marrow-derived mesenchymal stem cell). In another specific embodiment, said isolated placental stem cell is non-maternal in origin. In another specific embodiment, at least about 90%, at least about 95%, or at least 99%, of said cells in said isolated population of placental stem cells, are non-maternal in origin.

In another embodiment, provided herein is an isolated population of placental stem cells, wherein a plurality of said placental stem cells are positive for aldehyde dehydrogenase (ALDH), as assessed by an aldehyde dehydrogenase activity assay. Such assays are known in the art (see, e.g., Bostian and Betts, *Biochem. J.*, 173, 787, (1978)). In a specific embodiment, said ALDH assay uses ALDEFLUOR® (Aldagen, Inc., Ashland, Oreg.) as a marker of aldehyde dehydrogenase activity. In a specific embodiment, said plurality is between about 3% and about 25% of cells in said population of cells. In another embodiment, provided herein is a population of umbilical cord stem cells, wherein a plurality of said umbilical cord stem cells are positive for aldehyde dehydrogenase, as assessed by an aldehyde dehydrogenase activity assay that uses ALDEFLUOR® as an indicator of aldehyde dehydrogenase activity. In a specific embodiment, said plurality is between about 3% and about 25% of cells in said population of cells. In another embodiment, said population of placental stem cells or umbilical cord stem cells shows at least three-fold, or at least five-fold, higher ALDH activity than a population of bone marrow-derived mesenchymal stem cells having the same number of cells and cultured under the same conditions.

For any of the above placental stem cells, or populations of placental stem cells, the stem cell or population of placental stem cells are, or can comprise, cells that have been passaged at least 1, 2, 3, 4, 5, 6, 7, 8, 9, 10, 12, 14, 16, 18, or 20 times, or more, or expanded for 1, 2, 3, 4, 5, 6, 7, 8, 9, 10, 12, 14, 16, 18, 20, 22, 24, 26, 28, 30, 32, 34, 36, 38 or 40 population doublings, or more.

In a specific embodiment of any of the above placental cells or cell populations, the karyotype of the cells, or at least about 95% or about 99% of the cells in said population, is normal. In another specific embodiment of any of the above placental cells or cell populations, the cells, or cells in the population of cells, are non-maternal in origin.

Isolated placental stem cells, or isolated populations of placental stem cells, bearing any of the above combinations of markers, can be combined in any ratio. Any two or more of the above placental stem cell populations can be isolated, or enriched, to form a placental stem cell population. For example, an isolated population of placental stem cells comprising a first population of placental stem cells defined by one of the marker combinations described above can be combined with a second population of placental stem cells defined by another of the marker combinations described above, wherein said first and second populations are combined in a ratio of about 1:99, 2:98, 3:97, 4:96, 5:95, 10:90, 20:80, 30:70, 40:60, 50:50, 60:40, 70:30, 80:20, 90:10, 95:5, 96:4, 97:3, 98:2, or about 99:1. In like fashion, any three, four, five or more of the above-described placental stem cells or placental stem cell populations can be combined.

In a specific embodiment of the above-mentioned placental stem cells, the placental stem cells constitutively secrete IL-6, IL-8 and monocyte chemoattractant protein (MCP-1).

The immunosuppressive pluralities of placental stem cells described above can comprise about, at least, or no more than, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more placental stem cells.

5.2.3 Selecting and Producing Placental Stem Cell Populations

In another embodiment, provided herein is a method of selecting a plurality of immunosuppressive placental stem cells from a plurality of placental cells, comprising selecting a population of placental cells wherein at least 10%, at least 20%, at least 30%, at least 40%, at least 50% at least 60%, at least 70%, at least 80%, at least 90%, or at least 95% of said cells are CD200$^+$, HLA-G$^+$ placental stem cells, and wherein said placental stem cells detectably suppresses T cell proliferation in a mixed lymphocyte reaction (MLR) assay. In a specific embodiment, said selecting comprises selecting stem cells that are also CD73$^+$ and CD105$^+$. In another specific embodiment, said selecting comprises selecting stem cells that are also CD34$^-$, CD38$^-$ or CD45$^-$. In another specific embodiment, said selecting comprises selecting placental stem cells that are also CD34$^-$, CD38$^-$, CD45$^-$, CD73$^+$ and CD105$^+$. In another specific embodiment, said selecting also comprises selecting a plurality of placental stem cells that forms one or more embryoid-like bodies when cultured under conditions that allow the formation of embryoid-like bodies.

In another embodiment, provided herein is a method of selecting a plurality of immunosuppressive placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are CD73$^+$, CD105$^+$, CD200$^+$ placental stem cells, and wherein said placental stem cells detectably suppresses T cell proliferation in a mixed lymphocyte reaction (MLR) assay. In a specific embodiment, said selecting comprises selecting stem cells that are also HLA-G$^+$. In another specific embodiment, said selecting comprises selecting placental stem cells that are also CD34$^-$, CD38$^-$ or CD45$^-$. In another specific embodiment, said selecting comprises selecting placental stem cells that are also CD34$^-$, CD38$^-$ and CD45$^-$. In another specific embodiment, said selecting comprises selecting placental stem cells that are also CD34$^-$, CD38$^-$, CD45$^-$, and HLA-G$^+$. In another specific embodiment, said selecting additionally comprises selecting a population of placental cells that produces one or more embryoid-like bodies when the population is cultured under conditions that allow the formation of embryoid-like bodies.

In another embodiment, also provided herein is a method of selecting a plurality of immunosuppressive placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are CD200$^+$, OCT-4$^+$ placental stem cells, and wherein said placental stem cells detectably suppresses T cell proliferation in a mixed lymphocyte reaction (MLR) assay. In a specific embodiment, said selecting comprises selecting placental stem cells that are also CD73$^+$ and CD105$^+$. In another specific embodiment, said selecting comprises selecting placental stem cells that are also HLA-G$^+$. In another specific embodiment, said selecting comprises selecting placental stem cells that are also CD34$^-$, CD38$^-$ and CD45$^-$. In another specific embodiment, said selecting comprises selecting placental stem cells that are also CD34$^-$, CD38$^-$, CD45$^-$, CD73$^+$, CD105$^+$ and HLA-G$^+$.

In another embodiment, provided herein is a method of selecting a plurality of immunosuppressive placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are CD73$^+$, CD105$^+$ and HLA-G$^+$ placental stem cells, and wherein said placental stem cells detectably suppresses T cell proliferation in a mixed lymphocyte reaction (MLR) assay. In a specific embodiment, said selecting comprises selecting placental stem cells that are also CD34$^-$, CD38$^-$ or CD45$^-$. In another specific embodiment, said selecting comprises selecting placental stem cells that are also CD34$^-$, CD38$^-$ and CD45$^-$. In another specific embodiment, said selecting comprises selecting placental stem cells that are also CD200$^+$. In another specific embodiment, said selecting comprises selecting placental stem cells that are also CD34$^-$, CD38$^-$, CD45$^-$, OCT-4$^+$ and CD200$^+$.

In another embodiment, also provided herein is provides a method of selecting a plurality of immunosuppressive placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are CD73$^+$, CD105$^+$ placental stem cells, and wherein said plurality forms one or more embryoid-like bodies under conditions that allow formation of embryoid-like bodies. In a specific embodiment, said selecting comprises selecting placental stem cells that are also CD34$^-$, CD38$^-$ or CD45$^-$ In another specific embodiment, said selecting comprises selecting placental stem cells that are also CD34$^-$, CD38$^-$ and CD45$^-$. In another specific embodiment, said selecting comprises selecting placental stem cells that are also OCT-4$^+$. In a more specific embodiment, said selecting comprises selecting placental stem cells that are also OCT-4$^+$, CD34$^-$, CD38$^-$ and CD45$^-$.

In another embodiment, provided herein is a method of selecting a plurality of immunosuppressive placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said isolated placental cells are OCT4$^+$ stem cells, and wherein said plurality forms one or more embryoid-like bodies under conditions that allow formation of embryoid-like bodies. In a specific embodiment, said selecting comprises selecting placental stem cells that are also CD73$^+$ and CD105$^+$. In another specific embodiment, said selecting comprises selecting placental stem cells that are also CD34$^-$, CD38−, or CD45−. In another specific embodiment, said selecting comprises selecting placental stem cells that are also CD200+. In a more specific embodiment, said selecting comprises selecting placental stem cells that are also CD73+, CD105+, CD200+, CD34−, CD38−, and CD45−.

Immunosuppressive populations, or pluralities, of placental stem cells can be produced according to the methods provided herein. For example, provided herein is method of producing a cell population, comprising selecting any of the pluralities of placental stem cells described above, and isolating the plurality of placental stem cells from other cells, e.g., other placental cells. In a specific embodiment, provided herein is a method of producing a cell population comprising selecting placental cells, wherein said placental cells (a) adhere to a substrate, (b) express CD200 and HLA-G, or express CD73, CD105, and CD200, or express CD200 and OCT-4, or express CD73, CD105, and HLA-G, or express CD73 and CD105 and facilitate the formation of one or more embryoid-like bodies in a population of placental cells that comprise the stem cell, when said population is cultured under conditions that allow formation of embryoid-like bodies, or express OCT-4 and facilitate the formation of one or more embryoid-like bodies in a population of placental cells that comprise the stem cell, when said population is cultured under conditions that allow formation of embryoid-like bodies; and (c) detectably suppress CD4+ or CD8+ T cell proliferation in an MLR (mixed lymphocyte reaction) or regression assay; and isolating said placental cells from other cells to form a cell population.

In a more specific embodiment, immunosuppressive placental stem cell populations can be produced by a method comprising selecting placental stem cells that (a) adhere to a substrate, (b) express CD200 and HLA-G, and (c) detectably suppress CD4+ or CD8+ T cell proliferation in an MLR (mixed lymphocyte reaction); and isolating said placental stem cells from other cells to form a cell population. In another specific embodiment, the method comprises selecting placental stem cells that (a) adhere to a substrate, (b) express CD73, CD105, and CD200, and (c) detectably suppress CD4+ or CD8+ T cell proliferation in an MLR; and isolating said placental stem cells from other cells to form a cell population. In another specific embodiment, provided herein is a method of producing a cell population comprising selecting placental stem cells that (a) adhere to a substrate, (b) express CD200 and OCT-4, and (c) detectably suppress CD4+ or CD8+ T cell proliferation in an MLR; and isolating said placental stem cells from other cells to form a cell population. In another specific embodiment, provided herein is a method of producing a cell population comprising selecting placental stem cells that (a) adhere to a substrate, (b) express CD73 and CD105, (c) form embryoid-like bodies when cultured under conditions allowing the formation of embryoid-like bodies, and (d) detectably suppress CD4+ or CD8+ T cell proliferation in an MLR; and isolating said placental stem cells from other cells to form a cell population. In another specific embodiment, the method comprises selecting placental stem cells that (a) adhere to a substrate, (b) express CD73, CD105, and (c) detectably suppress CD4+ or CD8+ T cell proliferation in an MLR; and isolating said placental stem cells from other cells to form a cell population. A method of producing a cell population comprising selecting placental stem cells that (a) adhere to a substrate, (b) express OCT-4, (c) form embryoid-like bodies when cultured under conditions allowing the formation of embryoid-like bodies, and (d) detectably suppress CD4+ or CD8+ T cell proliferation in an MLR; and isolating said placental stem cells from other cells to form a cell population.

In a specific embodiment of the methods of producing an immunosuppressive placental stem cell population, said T cells and said placental cells are present in said MLR at a ratio of about 5:1. The placental cells used in the method can be derived from the whole placenta, or primarily from amnion, or amnion and chorion. In another specific embodiment, the placental cells suppress CD4+ or CD8+ T cell proliferation by at least 50%, at least 75%, at least 90%, or at least 95% in said MLR compared to an amount of T cell proliferation in said MLR in the absence of said placental cells. The method can additionally comprise the selection and/or production of a placental stem cell population capable of immunomodulation, e.g., suppression of the activity of, other immune cells, e.g., an activity of a natural killer (NK) cell.

5.2.4 Growth in Culture

The growth of the placental stem cells described herein, as for any mammalian cell, depends in part upon the particular medium selected for growth. Under optimum conditions, placental stem cells typically double in number in 3-5 days. During culture, the placental stem cells provided herein adhere to a substrate in culture, e.g. the surface of a tissue culture container (e.g., tissue culture dish plastic, fibronectin-coated plastic, and the like) and form a monolayer.

Populations of isolated placental cells that comprise the placental stem cells provided herein, when cultured under appropriate conditions, form embryoid-like bodies, that is, three-dimensional clusters of cells grow atop the adherent stem cell layer. Cells within the embryoid-like bodies express markers associated with very early stem cells, e.g., OCT-4, Nanog, SSEA3 and SSEA4. Cells within the embryoid-like bodies are typically not adherent to the culture substrate, as are the placental stem cells described herein, but remain attached to the adherent cells during culture. Embryoid-like body cells are dependent upon the adherent placental stem cells for viability, as embryoid-like bodies do not form in the absence of the adherent stem cells. The adherent placental stem cells thus facilitate the growth of one or more embryoid-like bodies in a population of placental cells that comprise the adherent placental stem cells. Without wishing to be bound by theory, the cells of the embryoid-like bodies are thought to grow on the adherent placental stem cells much as embryonic stem cells grow on a feeder layer of cells. Mesenchymal stem cells, e.g., bone marrow-derived mesenchymal stem cells, do not develop embryoid-like bodies in culture.

5.2.5 Differentiation

The placental stem cells, useful in the methods of treating diseases, disorder or conditions associated with, or caused by inappropriate or harmful immune response, e.g., inflammation, provided herein, are differentiable into different committed cell lineages. For example, the placental stem cells can be differentiated into cells of an adipogenic, chondrogenic, neurogenic, or osteogenic lineage. Such differentiation can be accomplished, e.g., by any method known in the art for differentiating, e.g., bone marrow-derived mesenchymal stem cells into similar cell lineages, or by methods described elsewhere herein.

The placental stem cells and umbilical cord stem cells provided herein can exhibit the capacity to differentiate into a particular cell lineage in vitro, in vivo, or in vitro and in vivo. In a specific embodiment, the placental stem cells and umbilical cord stem cells provided herein can be differentiated in vitro when placed in conditions that cause or promote differentiation into a particular cell lineage, but do not detectably differentiate in vivo, e.g., in a NOD-SCID mouse model.

5.3 Methods of Obtaining Placental Stem Cells

5.3.1 Stem Cell Collection Composition

Placental stem cells can be collected and isolated according to the methods provided herein. Generally, stem cells are obtained from a mammalian placenta using a physiologically-acceptable solution, e.g., a stem cell collection composition. A stem cell collection composition is described in detail in related U.S. Provisional Application No. 60/754,969, entitled "Improved Composition for Collecting and Preserving Placental Stem Cells and Methods of Using the Composition" filed on Dec. 29, 2005.

The stem cell collection composition can comprise any physiologically-acceptable solution suitable for the collection and/or culture of stem cells, for example, a saline solution (e.g., phosphate-buffered saline, Kreb's solution, modified Kreb's solution, Eagle's solution, 0.9% NaCl. etc.), a culture medium (e.g., DMEM, HDMEM, etc.), and the like.

The stem cell collection composition can comprise one or more components that tend to preserve placental stem cells, that is, prevent the placental stem cells from dying, or delay the death of the placental stem cells, reduce the number of placental stem cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The stem cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE, hyaluronidase, and the like.

The stem cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram(+) and/or Gram(−) bacteria, e.g., *Pseudomonas aeruginosa, Staphylococcus aureus*, and the like.

The stem cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 μM to about 100 μM); a reducing agent (e.g., N-acetylcysteine present at about 0.1 mM to about 5 mM); an agent that prevents calcium entry into cells (e.g., verapamil present at about 2 μM to about 25 μM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/1 to about 100,000 units/1); or an amiloride containing compound (e.g., amiloride, ethyl isopropyl amiloride, hexamethylene amiloride, dimethyl amiloride or isobutyl amiloride present at about 1.0 μM to about 5 μM).

5.3.2 Collection and Handling of Placenta

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the placenta or the stem cells harvested therefrom. For example, human placental stem cells can be used, in light of the medical history, for personalized medicine for the infant associated with the placenta, or for parents, siblings or other relatives of the infant.

Prior to recovery of placental stem cells, the umbilical cord blood and placental blood are removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifeBank Inc., Cedar Knolls, N.J., ViaCord, Cord Blood Registry and Cryocell. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of stem cells by, e.g., perfusion or tissue dissociation. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in pending U.S. patent application Ser. No. 11/230,760, filed Sep. 19, 2005.

Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to stem cell collection, can be stored under sterile conditions and at either room temperature or at a temperature of 5 to 25° C. (centigrade). The placenta may be stored for a period of longer than forty eight hours, and preferably for a period of four to twenty-four hours prior to perfusing the placenta to remove any residual cord blood. The placenta is preferably stored in an anticoagulant solution at a temperature of 5 to 25° C. (centigrade). Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before placental stem cells are collected.

The mammalian placenta or a part thereof, once collected and prepared generally as above, can be treated in any art-known manner, e.g., can be perfused or disrupted, e.g., digested with one or more tissue-disrupting enzymes, to obtain stem cells.

5.3.3 Physical Disruption and Enzymatic Digestion of Placental Tissue

In one embodiment, stem cells are collected from a mammalian placenta by physical disruption, e.g., enzymatic digestion, of the organ, e.g., using the stem cell collection composition described in Section 5.3.1, above. For example, the placenta, or a portion thereof, may be, e.g., crushed, sheared, minced, diced, chopped, macerated or the like, while in contact with, e.g., a buffer, medium or a stem cell collection composition, and the tissue subsequently digested with one or more enzymes. The placenta, or a portion thereof, may also be physically disrupted and digested with one or more enzymes, and the resulting material then immersed in, or mixed into, a buffer, medium or a stem cell collection composition. Any method of physical disruption can be used, provided that the method of disruption leaves a plurality, more preferably a majority, and more preferably at least 60%, 70%, 80%, 90%, 95%, 98%, or 99% of the cells in said organ viable, as determined by, e.g., trypan blue exclusion.

The placenta can be dissected into components prior to physical disruption and/or enzymatic digestion and stem cell recovery. For example, placental stem cells can be obtained from the amniotic membrane, chorion, placental cotyledons, or any combination thereof, or umbilical cord, or any combination thereof. Preferably, placental stem cells are obtained from placental tissue comprising amnion and chorion, or amnion-chorion and umbilical cord. In one embodiment, stem cells are obtained from amnion-chorion and umbilical cord in about a 1:1 weight ratio. Typically, placental stem cells can be obtained by disruption of a small block of placental tissue, e.g., a block of placental tissue that is about 1, 2, 3, 4, 5, 6, 7, 8, 9, 10, 20, 30, 40, 50, 60, 70, 80, 90, 100, 200, 300, 400, 500, 600, 700, 800, 900 or about 1000 cubic millimeters in volume.

A preferred stem cell collection composition comprises one or more tissue-disruptive enzyme(s). Enzymatic digestion preferably uses a combination of enzymes, e.g., a combination of a matrix metalloprotease and a neutral protease, for example, a combination of collagenase and dispase. In one embodiment, enzymatic digestion of placental tissue uses a combination of a matrix metalloprotease, a neutral protease, and a mucolytic enzyme for digestion of hyaluronic acid, such as a combination of collagenase, dispase, and hyaluronidase or a combination of LIBERASE (Boehringer Mannheim Corp., Indianapolis, Ind.) and hyaluronidase. Other enzymes that can be used to disrupt placenta tissue include papain, deoxyribonucleases, serine proteases, such as trypsin, chymotrypsin, or elastase. Serine proteases may be inhibited by alpha 2 microglobulin in serum and therefore the medium used for digestion is usually serum-free. EDTA and DNase are commonly used in enzyme digestion procedures to increase the efficiency of cell recovery. The digestate is preferably diluted so as to avoid trapping stem cells within the viscous digest.

Any combination of tissue digestion enzymes can be used. Typical concentrations for tissue digestion enzymes include, e.g., 50-200 U/mL for collagenase I and collagenase IV, 1-10 U/mL for dispase, and 10-100 U/mL for elastase. Proteases can be used in combination, that is, two or more proteases in the same digestion reaction, or can be used sequentially in order to liberate placental stem cells. For example, in one embodiment, a placenta, or part thereof, is digested first with an appropriate amount of collagenase I at 2 mg/ml for 30 minutes, followed by digestion with trypsin, 0.25%, for 10 minutes, at 37° C. Serine proteases are preferably used consecutively following use of other enzymes.

In another embodiment, the tissue can further be disrupted by the addition of a chelator, e.g., ethylene glycol bis(2-aminoethyl ether)-N,N,N'N'-tetraacetic acid (EGTA) or ethylenediaminetetraacetic acid (EDTA) to the stem cell collection composition comprising the stem cells, or to a solution in which the tissue is disrupted and/or digested prior to isolation of the stem cells with the stem cell collection composition.

It will be appreciated that where an entire placenta, or portion of a placenta comprising both fetal and maternal cells (for example, where the portion of the placenta comprises the chorion or cotyledons), the placental stem cells collected will comprise a mix of placental stem cells derived from both fetal and maternal sources. Where a portion of the placenta that comprises no, or a negligible number of, maternal cells (for example, amnion), the placental stem cells collected will comprise almost exclusively fetal placental stem cells.

5.3.4 Placental Perfusion

Placental stem cells can also be obtained by perfusion of the mammalian placenta. Methods of perfusing mammalian placenta to obtain stem cells are disclosed, e.g., in Hariri, U.S. Application Publication No. 2002/0123141, and in related U.S. Provisional Application No. 60/754,969, entitled "Improved Composition for Collecting and Preserving Placental Stem Cells and Methods of Using the Composition" filed on Dec. 29, 2005.

Placental stem cells can be collected by perfusion, e.g., through the placental vasculature, using, e.g., a stem cell collection composition as a perfusion solution. In one embodiment, a mammalian placenta is perfused by passage of perfusion solution through either or both of the umbilical artery and umbilical vein. The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® or plastic cannula, that is connected to a sterile connection apparatus, such as sterile tubing. The sterile connection apparatus is connected to a perfusion manifold.

In preparation for perfusion, the placenta is preferably oriented (e.g., suspended) in such a manner that the umbilical artery and umbilical vein are located at the highest point of the placenta. The placenta can be perfused by passage of a perfusion fluid, e.g., the stem cell collection composition provided herein, through the placental vasculature, or through the placental vasculature and surrounding tissue. In one embodiment, the umbilical artery and the umbilical vein are connected simultaneously to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. In another embodiment, the perfusion solution is passed through the umbilical veins and collected from the umbilical artery, or is passed through the umbilical artery and collected from the umbilical veins.

In one embodiment, the proximal umbilical cord is clamped during perfusion, and more preferably, is clamped within 4-5 cm (centimeter) of the cord's insertion into the placental disc.

The first collection of perfusion fluid from a mammalian placenta during the exsanguination process is generally colored with residual red blood cells of the cord blood and/or placental blood. The perfusion fluid becomes more colorless as perfusion proceeds and the residual cord blood cells are washed out of the placenta. Generally from 30 to 100 ml (milliliter) of perfusion fluid is adequate to initially exsanguinate the placenta, but more or less perfusion fluid may be used depending on the observed results.

The volume of perfusion liquid used to collect placental stem cells may vary depending upon the number of stem cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days. Where the placenta is to be perfused a plurality of times, it may be maintained or cultured under aseptic conditions in a container or other suitable vessel, and perfused with the stem cell collection composition, or a standard perfusion solution (e.g., a normal saline solution such as phosphate buffered saline ("PBS")) with or without an anticoagulant (e.g., heparin, warfarin sodium, coumarin, bishydroxycoumarin), and/or with or without an antimicrobial agent (e.g., β-mercaptoethanol (0.1 mM); antibiotics such as streptomycin (e.g., at 40-100 µg/ml), penicillin (e.g., at 40 U/ml), amphotericin B (e.g., at 0.5 µg/ml). In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In a preferred embodiment, perfusion of the placenta and collection of perfusion solution, e.g., stem cell collection composition, is repeated until the number of recovered nucleated cells falls below 100 cells/ml. The perfusates at different time points can be further processed individually to recover time-dependent populations of cells, e.g., stem cells. Perfusates from different time points can also be pooled.

Without wishing to be bound by any theory, after exsanguination and a sufficient time of perfusion of the placenta, placental stem cells are believed to migrate into the exsanguinated and perfused microcirculation of the placenta where they are collected, preferably by washing into a collecting vessel by perfusion. Perfusing the isolated placenta not only serves to remove residual cord blood but also provide the placenta with the appropriate nutrients, including oxygen. The placenta may be cultivated and perfused with a similar solution which was used to remove the residual cord blood cells, preferably, without the addition of anticoagulant agents.

Perfusion as described herein results in the collection of significantly more placental stem cells than the number obtainable from a mammalian placenta not perfused with said solution, and not otherwise treated to obtain stem cells (e.g., by tissue disruption, e.g., enzymatic digestion). In this context, "significantly more" means at least 10% more. Perfusion yields significantly more placental stem cells than, e.g., the number of placental stem cells obtainable from culture medium in which a placenta, or portion thereof, has been cultured.

Stem cells can be isolated from placenta by perfusion with a solution comprising one or more proteases or other tissue-disruptive enzymes. In a specific embodiment, a placenta or portion thereof (e.g., amniotic membrane, amnion and chorion, placental lobule or cotyledon, or combination of any of the foregoing) is brought to 25-37° C., and is incubated with one or more tissue-disruptive enzymes in 200 mL of a culture medium for 30 minutes. Cells from the perfusate are collected, brought to 4° C., and washed with a cold inhibitor mix comprising 5 mM EDTA, 2 mM dithiothreitol and 2 mM beta-mercaptoethanol. The stem cells are washed after several minutes with a cold (e.g., 4° C.) stem cell collection composition described elsewhere herein.

It will be appreciated that perfusion using the pan method, that is, whereby perfusate is collected after it has exuded from the maternal side of the placenta, results in a mix of fetal and maternal cells. As a result, the cells collected by this method comprise a mixed population of placental stem cells of both fetal and maternal origin. In contrast, perfusion solely through the placental vasculature, whereby perfusion fluid is passed through one or two placental vessels and is collected solely through the remaining vessel(s), results in the collection of a population of placental stem cells almost exclusively of fetal origin.

5.3.5 Isolation, Sorting, and Characterization of Placental Stem Cells

Stem cells from mammalian placenta, whether obtained by perfusion or enzymatic digestion, can initially be purified from (i.e., be isolated from) other cells by Ficoll gradient centrifugation. Such centrifugation can follow any standard protocol for centrifugation speed, etc. In one embodiment, for example, cells collected from the placenta are recovered from perfusate by centrifugation at 5000×g for 15 minutes at room temperature, which separates cells from, e.g., contaminating debris and platelets. In another embodiment, placental perfusate is concentrated to about 200 ml, gently layered over Ficoll, and centrifuged at about 1100×g for 20 minutes at 22° C., and the low-density interface layer of cells is collected for further processing.

Cell pellets can be resuspended in fresh stem cell collection composition, or a medium suitable for stem cell maintenance, e.g., IMDM serum-free medium containing 2 U/ml heparin and 2 mM EDTA (GibcoBRL, NY). The total mononuclear cell fraction can be isolated, e.g., using Lymphoprep (Nycomed Pharma, Oslo, Norway) according to the manufacturer's recommended procedure.

As used herein, "isolating" placental stem cells means to remove at least 20%, 30%, 40%, 50%, 60%, 70%, 80%, 90%, 95% or 99% of the cells with which the stem cells are normally associated in the intact mammalian placenta. A stem cell from an organ is "isolated" when it is present in a population of cells that comprises fewer than 50% of the cells with which the stem cell is normally associated in the intact organ.

Placental cells obtained by perfusion or digestion can, for example, be further, or initially, isolated by differential trypsinization using, e.g., a solution of 0.05% trypsin with 0.2% EDTA (Sigma, St. Louis Mo.). Differential trypsinization is possible because placental stem cells typically detach from plastic surfaces within about five minutes whereas other adherent populations typically require more than 20-30 minutes incubation. The detached placental stem cells can be harvested following trypsinization and trypsin neutralization, using, e.g., Trypsin Neutralizing Solution (TNS, Cambrex). In one embodiment of isolation of adherent cells, aliquots of, for example, about $5\text{-}10\times10^6$ cells are placed in each of several T-75 flasks, preferably fibronectin-coated T75 flasks. In such an embodiment, the cells can be cultured with commercially available Mesenchymal Stem Cell Growth Medium (MSCGM) (Cambrex), and placed in a tissue culture incubator (37° C., 5% $CO_2$). After 10 to 15 days, non-adherent cells are removed from the flasks by washing with PBS. The PBS is then replaced by MSCGM. Flasks are preferably examined daily for the presence of various adherent cell types and in particular, for identification and expansion of clusters of fibroblastoid cells.

The number and type of cells collected from a mammalian placenta can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using antibodies to CD34, one can determine, using the techniques above, whether a cell comprises a detectable amount of CD34; if so, the cell is $CD34^+$. Likewise, if a cell produces enough OCT-4 RNA to be detectable by RT-PCR, or significantly more OCT-4 RNA than an adult cell, the cell is $OCT\text{-}4^+$ Antibodies to cell surface markers (e.g., CD markers such as CD34) and the sequence of stem cell-specific genes, such as OCT-4, are well-known in the art.

Placental cells, particularly cells that have been isolated by Ficoll separation, differential adherence, or a combination of both, may be sorted using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one sorting scheme, stem cells from placenta are sorted on the basis of expression of the markers CD34, CD38, CD44, CD45, CD73, CD105, OCT-4 and/or HLA-G. This can be accomplished in connection with procedures to select stem cells on the basis of their adherence properties in culture. For example, an adherence selection stem can be accomplished before or after sorting on the basis of marker expression. In one embodiment, for example, cells are sorted first on the basis of their expression of CD34; $CD34^-$ cells are retained, and cells that are $CD200^+$ $HLA\text{-}G^+$, are separated from all other $CD34^-$ cells. In another embodiment, cells from placenta are based on their expression of markers CD200 and/or HLA-G; for example, cells displaying either of these markers are isolated for further use. Cells that express, e.g., CD200 and/or HLA-G can, in a specific embodiment, be further sorted based on their expression of CD73 and/or CD105, or epitopes recognized by antibodies SH2, SH3 or SH4, or lack of expression of CD34, CD38 or CD45. For example, in one embodiment, placental cells are sorted by expression, or lack thereof, of CD200, HLA-G, CD73, CD105, CD34, CD38 and CD45, and placental cells that are $CD200^+$, $HLA\text{-}G^+$, $CD73^+$, $CD105^+$, $CD34^-$, $CD38^-$ and $CD45^-$ are isolated from other placental cells for further use.

In another embodiment, magnetic beads can be used to separate cells. The cells may be sorted using a magnetic activated cell sorting (MACS) technique, a method for separating particles based on their ability to bind magnetic beads (0.5-100 μm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Placental stem cells can also be characterized and/or sorted based on cell morphology and growth characteristics. For example, placental stem cells can be characterized as having, and/or selected on the basis of, e.g., a fibroblastoid appearance in culture. Placental stem cells can also be characterized as having, and/or be selected, on the basis of their ability to form embryoid-like bodies. In one embodiment, for example, placental cells that are fibroblastoid in shape, express CD73 and CD105, and produce one or more embryoid-like bodies in culture are isolated from other placental cells. In another embodiment, OCT-4+ placental cells that produce one or more embryoid-like bodies in culture are isolated from other placental cells.

In another embodiment, placental stem cells can be identified and characterized by a colony forming unit assay. Colony forming unit assays are commonly known in the art, such as Mesen Cult™ medium (Stem Cell Technologies, Inc., Vancouver British Columbia)

Placental stem cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods well known in the art, such as by determining the maximum number of population doubling in an extended culture.

Placental stem cells can also be separated from other placental cells using other techniques known in the art, e.g., selective growth of desired cells (positive selection), selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

5.4 Culture of Placental Stem Cells

5.4.1 Culture Media

Isolated placental stem cells, or placental stem cell population, or cells or placental tissue from which placental stem cells grow out, can be used to initiate, or seed, cell cultures. Cells are generally transferred to sterile tissue culture vessels either uncoated or coated with extracellular matrix or ligands such as laminin, collagen (e.g., native or denatured), gelatin, fibronectin, ornithine, vitronectin, and extracellular membrane protein (e.g., MATRIGEL (BD Discovery Labware, Bedford, Mass.)).

Placental stem cells can be cultured in any medium, and under any conditions, recognized in the art as acceptable for the culture of stem cells. Preferably, the culture medium comprises serum. Placental stem cells can be cultured in, for example, DMEM-LG (Dulbecco's Modified Essential Medium, low glucose)/MCDB 201 (chick fibroblast basal medium) containing ITS (insulin-transferrin-selenium), LA+BSA (linoleic acid-bovine serum albumin), dextrose, L-ascorbic acid, PDGF, EGF, IGF-1, and penicillin/streptomycin; DMEM-HG (high glucose) comprising 10% fetal bovine serum (FBS); DMEM-HG comprising 15% FBS; IMDM (Iscove's modified Dulbecco's medium) comprising 10% FBS, 10% horse serum, and hydrocortisone; M199 comprising 10% FBS, EGF, and heparin; α-MEM (minimal essential medium) comprising 10% FBS, GlutaMAX™ and gentamicin; DMEM comprising 10% FBS, GlutaMAX™ and gentamicin, etc. A preferred medium is DMEM-LG/MCDB-201 comprising 2% FBS, ITS, LA+BSA, dextrose, L-ascorbic acid, PDGF, EGF, and penicillin/streptomycin.

Other media in that can be used to culture placental stem cells include DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMIEM/F12, RPMI 1640, advanced DMEM (Gibco), DMEM/MCDB201 (Sigma), and CELL-GRO FREE.

The culture medium can be supplemented with one or more components including, for example, serum (e.g., fetal bovine serum (FBS), preferably about 2-15% (v/v); equine (horse) serum (ES); human serum (HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1 (IGF-1), leukemia inhibitory factor (LIF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination.

5.4.2 Expansion and Proliferation of Placental Stem Cells

Once an isolated placental stem cell, or isolated population of stem cells (e.g., a stem cell or population of stem cells separated from at least 50% of the placental cells with which the stem cell or population of stem cells is normally associated in vivo), the stem cell or population of stem cells can be proliferated and expanded in vitro. For example, a population of placental stem cells can be cultured in tissue culture containers, e.g., dishes, flasks, multiwell plates, or the like, for a sufficient time for the stem cells to proliferate to 70-90% confluence, that is, until the stem cells and their progeny occupy 70-90% of the culturing surface area of the tissue culture container.

Placental stem cells can be seeded in culture vessels at a density that allows cell growth. For example, the cells may be seeded at low density (e.g., about 1,000 to about 5,000 cells/cm$^2$) to high density (e.g., about 50,000 or more cells/cm$^2$). In a preferred embodiment, the cells are cultured at about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at about 25° C. to about 40° C., preferably 37° C. The cells are preferably cultured in an incubator. The culture medium can be static or agitated, for example, using a bioreactor. Placental stem cells preferably are grown under low oxidative stress (e.g., with addition of glutathione, ascorbic acid, catalase, tocopherol, N-acetylcysteine, or the like).

Once 70%-90% confluence is obtained, the cells may be passaged. For example, the cells can be enzymatically treated, e.g., trypsinized, using techniques well-known in the art, to separate them from the tissue culture surface. After removing the cells by pipetting and counting the cells, about 20,000-100,000 stem cells, preferably about 50,000 stem cells, are passaged to a new culture container containing fresh culture medium. Typically, the new medium is the same type of medium from which the stem cells were removed. Provided herein are populations of placental stem cells that have been passaged at least 1, 2, 3, 4, 5, 6, 7, 8, 9, 10, 12, 14, 16, 18, or 20 times, or more, and combinations of the same.

5.4.3 Placental Stem Cell Populations

The methods of treatment provided herein, in certain embodiments, use populations of placental stem cells. Placental stem cell populations can be isolated directly from one or more placentas; that is, the placental stem cell population can be a population of placental cells, comprising placental stem cells, obtained from, or contained within, perfusate, or obtained from, or contained within, digestate (that is, the collection of cells obtained by enzymatic digestion of a placenta or part thereof). Isolated placental stem cells as described herein can also be cultured and expanded to produce placental stem cell populations. Populations of placental cells comprising placental stem cells can also be cultured and expanded to produce placental stem cell populations.

Placental stem cell populations described herein comprise placental stem cells, for example, placental stem cells as described herein. In various embodiments, at least 10%, 20%, 30%, 40%, 50%, 60%, 70%, 80%, 90%, 95%, or 99% of the cells in an isolated placental stem cell population are placental stem cells. That is, a placental stem cell population can comprise, e.g., as much as 1%, 5%, 10%, 20%, 30%, 40%, 50%, 60%, 70%, 80%, 90% non-stem cells.

Provided herein are methods of producing isolated placental stem cell population by, e.g., selecting placental stem cells, whether derived from enzymatic digestion or perfusion, that express particular markers and/or particular culture or morphological characteristics. In one embodiment, for example, a cell population can be produced by a method comprising selecting placental cells that (a) adhere to a substrate, and (b) express CD200 and HLA-G; and isolating said cells from other cells to form a cell population. In another embodiment, the method of producing a cell population comprises selecting placental cells that (a) adhere to a substrate, and (b) express CD73, CD105, and CD200; and isolating said cells from other cells to form a cell population. In another embodiment, the method of producing a cell population comprises selecting placental cells that (a) adhere to a substrate and (b) express CD200 and OCT-4; and isolating said cells from other cells to form a cell population. In another embodiment, the method of producing a cell population comprises selecting placental cells that (a) adhere to a substrate, (b) express CD73 and CD105, and (c) facilitate the formation of one or more embryoid-like bodies in a population of placental cells comprising said stem cell when said population is cultured under conditions that allow for the formation of an embryoid-like body; and isolating said cells from other cells to form a cell population. In another embodiment, the method of producing a cell population comprises selecting placental cells that (a) adhere to a substrate, and (b) express CD73, CD105 and HLA-G; and isolating said cells from other cells to form a cell population. In another embodiment, the method of producing a cell population comprises selecting placental cells that (a) adhere to a substrate, (b) express OCT-4, and (c) facilitate the formation of one or more embryoid-like bodies in a population of placental cells comprising said stem cell when said population is cultured under conditions that allow for the formation of an embryoid-like body; and isolating said cells from other cells to form a cell population. In any of the above embodiments, the method can additionally comprise selecting placental cells that express ABC-p (a placenta-specific ABC transporter protein; see, e.g., Allikmets et al., Cancer Res. 58(23):5337-9 (1998)). The method can also comprise selecting cells exhibiting at least one characteristic specific to, e.g., a mesenchymal stem cell, for example, expression of CD29, expression of CD44, expression of CD90, or expression of a combination of the foregoing.

In the above embodiments, the substrate can be any surface on which culture and/or selection of cells, e.g., placental stem cells, can be accomplished. Typically, the substrate is plastic, e.g., tissue culture dish or multiwell plate plastic. Tissue culture plastic can be coated with a biomolecule, e.g., laminin or fibronectin.

Cells, e.g., placental stem cells, can be selected for a placental stem cell population by any means known in the art of cell selection. For example, cells can be selected using an antibody or antibodies to one or more cell surface markers, for example, in flow cytometry or FACS. Selection can be accomplished using antibodies in conjunction with magnetic beads. Antibodies that are specific for certain stem cell-related markers are known in the art. For example, antibodies to OCT-4 (Abcam, Cambridge, Mass.), CD200 (Abcam), HLA-G (Abcam), CD73 (BD Biosciences Pharmingen, San Diego, Calif.), CD105 (Abcam; BioDesign International, Saco, Me.), etc. Antibodies to other markers are also available commercially, e.g., CD34, CD38 and CD45 are available from, e.g., StemCell Technologies or BioDesign International.

The isolated placental stem cell population can comprise placental cells that are not stem cells, or cells that are not placental cells.

Isolated placental stem cell populations can be combined with one or more populations of non-stem cells or non-placental cells. For example, an isolated population of placental stem cells can be combined with blood (e.g., placental blood or umbilical cord blood), blood-derived stem cells (e.g., stem cells derived from placental blood or umbilical cord blood), populations of blood-derived nucleated cells, bone marrow-derived mesenchymal cells, bone-derived stem cell populations, crude bone marrow, adult (somatic) stem cells, populations of stem cells contained within tissue, cultured stem cells, populations of fully-differentiated cells (e.g., chondrocytes, fibroblasts, amniotic cells, osteoblasts, muscle cells, cardiac cells, etc.) and the like. Cells in an isolated placental stem cell population can be combined with a plurality of cells of another type in ratios of about 100,000,000:1, 50,000,000:1, 20,000,000:1, 10,000,000:1, 5,000,000:1, 2,000,000:1, 1,000,000:1, 500,000:1, 200,000:1, 100,000:1, 50,000:1, 20,000:1, 10,000:1, 5,000:1, 2,000:1, 1,000:1, 500:1, 200:1, 100:1, 50:1, 20:1, 10:1, 5:1, 2:1, 1:1; 1:2; 1:5; 1:10; 1:100; 1:200; 1:500; 1:1,000; 1:2,000; 1:5,000; 1:10,000; 1:20,000; 1:50,000; 1:100,000; 1:500,000; 1:1,000,000; 1:2,000,000; 1:5,000,000; 1:10,000,000; 1:20,000,000; 1:50,000,000; or about 1:100,000,000, comparing numbers of total nucleated cells in each population. Cells in an isolated placental stem cell population can be combined with a plurality of cells of a plurality of cell types, as well.

In one, an isolated population of placental stem cells is combined with a plurality of hematopoietic stem cells. Such hematopoietic stem cells can be, for example, contained within unprocessed placental, umbilical cord blood or peripheral blood; in total nucleated cells from placental blood, umbilical cord blood or peripheral blood; in an isolated population of $CD34^+$ cells from placental blood, umbilical cord blood or peripheral blood; in unprocessed bone marrow; in total nucleated cells from bone marrow; in an isolated population of $CD34^+$ cells from bone marrow, or the like.

5.5 Preservation of Placental Stem Cells

Placental stem cells can be preserved, that is, placed under conditions that allow for long-term storage, or conditions that inhibit cell death by, e.g., apoptosis or necrosis.

Placental stem cells can be preserved using, e.g., a composition comprising an apoptosis inhibitor, necrosis inhibitor and/or an oxygen-carrying perfluorocarbon, as described in related U.S. Provisional Application No. 60/754,969, entitled "Improved Composition for Collecting and Preserving Placental Stem Cells and Methods of Using the Composition" filed on Dec. 25, 2005. In one embodiment, provided herein is a method of preserving a population of stem cells comprising contacting said population of stem cells with a stem cell collection composition comprising an inhibitor of apoptosis and an oxygen-carrying perfluorocarbon, wherein said inhibitor of apoptosis is present in an amount and for a time sufficient to reduce or prevent apoptosis in the population of stem cells, as compared to a population of stem cells not contacted with the inhibitor of apoptosis. In a specific embodiment, said inhibitor of apoptosis is a caspase inhibitor. In another specific embodiment, said inhibitor of apoptosis is a JNK inhibitor. In a more specific embodiment, said JNK inhibitor does not modulate differentiation or proliferation of said stem cells. In another embodiment, said stem cell collection composition comprises said inhibitor of apoptosis and said oxygen-carrying perfluorocarbon in separate phases. In another embodiment, said stem cell collection composition comprises said inhibitor of apoptosis and said oxygen-carrying perfluorocarbon in an emulsion. In another embodiment, the stem cell collection composition additionally comprises an emulsifier, e.g., lecithin. In another embodiment, said apoptosis inhibitor and said perfluorocarbon are between about 0° C. and about 25° C. at the time of contacting the stem cells. In another more specific embodiment, said apoptosis inhibitor and said perfluorocarbon are between about 2° C. and 10° C., or between about 2° C. and about 5° C., at the time of contacting the stem cells. In another more specific embodiment, said contacting is performed during transport of said population of stem cells. In another more specific embodiment, said contacting is performed during freezing and thawing of said population of stem cells.

In another embodiment, populations of placental stem cells can be preserved by a method comprising contacting said population of stem cells with an inhibitor of apoptosis and an organ-preserving compound, wherein said inhibitor of apoptosis is present in an amount and for a time sufficient to reduce or prevent apoptosis in the population of stem cells, as compared to a population of stem cells not contacted with the inhibitor of apoptosis. In a specific embodiment, the organ-preserving compound is UW solution (described in U.S. Pat. No. 4,798,824; also known as ViaSpan; see also Southard et al., *Transplantation* 49(2):251-257 (1990)) or a solution described in Stern et al., U.S. Pat. No. 5,552,267. In another embodiment, said organ-preserving compound is hydroxyethyl starch, lactobionic acid, raffinose, or a combination thereof. In another embodiment, the stem cell collection composition additionally comprises an oxygen-carrying perfluorocarbon, either in two phases or as an emulsion.

In another embodiment of the method, placental stem cells are contacted with a stem cell collection composition comprising an apoptosis inhibitor and oxygen-carrying perfluorocarbon, organ-preserving compound, or combination thereof, during perfusion. In another embodiment, said stem cells are contacted during a process of tissue disruption, e.g., enzymatic digestion. In another embodiment, placental stem cells are contacted with said stem cell collection compound after collection by perfusion, or after collection by tissue disruption, e.g., enzymatic digestion.

Typically, during placental cell collection, enrichment and isolation, it is preferable to minimize or eliminate cell stress due to hypoxia and mechanical stress. In another embodiment of the method, therefore, a stem cell, or population of stem cells, is exposed to a hypoxic condition during collection, enrichment or isolation for less than six hours during said preservation, wherein a hypoxic condition is a concentration of oxygen that is less than normal blood oxygen concentration. In a more specific embodiment, said population of stem cells is exposed to said hypoxic condition for less than two hours during said preservation. In another more specific embodiment, said population of stem cells is exposed to said hypoxic condition for less than one hour, or less than thirty minutes, or is not exposed to a hypoxic condition, during collection, enrichment or isolation. In another specific embodiment, said population of stem cells is not exposed to shear stress during collection, enrichment or isolation.

The placental stem cells described herein can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of, e.g., about 10% (v/v). Cryopreservation medium may comprise additional agents, for example, Plasmalyte, methylcellulose and/or glycerol. Placental stem cells are preferably cooled at about 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreserved cells preferably are thawed at a temperature of about 25° C. to about 40° C., preferably to a temperature of about 37° C.

5.6 Uses of Placental Stem Cells 5.6.1 Compositions Comprising Placental Stem Cells The methods of immunosuppression provided herein can use compositions comprising placental stem cells, or biomolecules therefrom. In the same manner, the pluralities and populations of placental stem cells provided herein can be combined with any physiologically-acceptable or medically-acceptable compound, composition or device for use in, e.g., research or therapeutics.

5.6.1.1 Cryopreserved Placental Stem Cells

The immunosuppressive placental stem cells, and populations of the cells, described herein can be preserved, for example, cryopreserved for later use. Methods for cryopreservation of cells, such as stem cells, are well known in the art. Placental stem cell populations can be prepared in a form that is easily administrable to an individual. For example, placental stem cells, or populations of the placental stem cells, described herein can be contained within a container that is suitable for medical use. Such a container can be, for example, a sterile plastic bag, flask, jar, or other container from which the placental stem cell population can be easily dispensed. For example, the container can be a blood bag or other plastic, medically-acceptable bag suitable for the intravenous administration of a liquid to a recipient. The container is preferably one that allows for cryopreservation of the combined stem cell population.

Cryopreserved immunosuppressive placental stem cell populations can comprise placental stem cells derived from a single donor, or from multiple donors. The placental stem cell population can be completely HLA-matched to an intended recipient, or partially or completely HLA-mismatched.

Thus, in one embodiment, provided herein is a composition comprising an immunosuppressive placental stem cell population in a container. In a specific embodiment, the stem cell population is cryopreserved. In another specific embodiment, the container is a bag, flask, or jar. In more specific embodiment, said bag is a sterile plastic bag. In a more specific embodiment, said bag is suitable for, allows or facilitates intravenous administration of said placental stem cell population. The bag can comprise multiple lumens or compartments that are interconnected to allow mixing of the placental stem cells and one or more other solutions, e.g., a drug, prior to, or during, administration. In another specific embodiment, the composition comprises one or more compounds that facilitate cryopreservation of the combined stem cell population. In another specific embodiment, said placental stem cell population is contained within a physiologically-acceptable aqueous solution. In a more specific embodiment, said physiologically-acceptable aqueous solution is a 0.9% NaCl solution. In another specific embodiment, said placental stem cell population comprises placental cells that are HLA-matched to a recipient of said stem cell population. In another specific embodiment, said combined stem cell population comprises placental cells that are at least partially HLA-mismatched to a recipient of said stem cell population. In another specific embodiment, said placental stem cells are derived from a plurality of donors.

5.6.1.2 Pharmaceutical Compositions

Immunosuppressive populations of placental stem cells, or populations of cells comprising placental stem cells, can be formulated into pharmaceutical compositions for use in vivo. Such pharmaceutical compositions comprise a population of placental stem cells, or a population of cells comprising placental stem cells, in a pharmaceutically-acceptable carrier, e.g., a saline solution or other accepted physiologically-acceptable solution for in vivo administration. Pharmaceutical compositions provided herein can comprise any of the placental stem cell populations, or placental stem cell types, described elsewhere herein. The pharmaceutical compositions can comprise fetal, maternal, or both fetal and maternal placental stem cells. The pharmaceutical compositions provided herein can further comprise placental stem cells obtained from a single individual or placenta, or from a plurality of individuals or placentae.

The pharmaceutical compositions provided herein can comprise any immunosuppressive number of placental stem cells. For example, a single unit dose of placental stem cells can comprise, in various embodiments, about, at least, or no more than $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or more placental stem cells.

The pharmaceutical compositions provided herein can comprise populations of cells that comprise 50% viable cells or more (that is, at least 50% of the cells in the population are functional or living). Preferably, at least 60% of the cells in the population are viable. More preferably, at least 70%, 80%, 90%, 95%, or 99% of the cells in the population in the pharmaceutical composition are viable.

The pharmaceutical compositions provided herein can comprise one or more compounds that, e.g., facilitate engraftment (e.g., anti-T-cell receptor antibodies, an immunosuppressant, or the like); stabilizers such as albumin, dextran 40, gelatin, hydroxyethyl starch, and the like.

5.6.1.3 Placental Stem Cell Conditioned Media

The placental stem cells provided herein can be used to produce conditioned medium that is immunosuppressive, that is, medium comprising one or more biomolecules secreted or excreted by the stem cells that have a detectable immunosuppressive effect on a plurality of one or more types of immune cells. In various embodiments, the conditioned medium comprises medium in which placental stem cells have grown for at least 1, 2, 3, 4, 5, 6, 7, 8, 9, 10, 11, 12, 13, 14 or more days. In other embodiments, the conditioned medium comprises medium in which placental stem cells have grown to at least 30%, 40%, 50%, 60%, 70%, 80%, 90% confluence, or up to 100% confluence. Such conditioned medium can be used to support the culture of a separate population of placental stem cells, or stem cells of another kind. In another embodiment, the conditioned medium comprises medium in which placental stem cells have been differentiated into an adult cell type. In another embodiment, the conditioned medium comprises medium in which placental stem cells and non-placental stem cells have been cultured.

Thus, in one embodiment, provided herein is a composition comprising culture medium from a culture of placental stem cells, wherein said placental stem cells (a) adhere to a substrate; (b) express CD200 and HLA-G, or express CD73, CD105, and CD200, or express CD200 and OCT-4, or express CD73, CD105, and HLA-G, or express CD73 and CD105 and facilitate the formation of one or more embryoid-like bodies in a population of placental cells that comprise the placental stem cells, when said population is cultured under conditions that allow formation of embryoid-like bodies, or express OCT-4 and facilitate the formation of one or more embryoid-like bodies in a population of placental cells that comprise the placental stem cells when said population is cultured under conditions that allow formation of embryoid-like bodies; and (c) detectably suppress $CD4^+$ or $CD8^+$ T cell proliferation in an MLR (mixed lymphocyte reaction), wherein said culture of placental stem cells has been cultured in said medium for 24 hours or more. In a specific embodiment, the composition further comprises a plurality of said placental stem cells. In another specific embodiment, the composition comprises a plurality of non-placental cells. In a more specific embodiment, said non-placental cells comprise $CD34^+$ cells, e.g., hematopoietic progenitor cells, such as peripheral blood hematopoietic progenitor cells, cord blood hematopoietic progenitor cells, or placental blood hematopoietic progenitor cells. The non-placental cells can also comprise other stem cells, such as mesenchymal stem cells, e.g., bone marrow-derived mesenchymal stem cells. The non-placental cells can also be one ore more types of adult cells or cell lines. In another specific embodiment, the composition comprises an anti-proliferative agent, e.g., an anti-MIP-1α or anti-MIP-1β antibody.

5.6.1.4 Matrices Comprising Placental Stem Cells

Further provided herein are matrices, hydrogels, scaffolds, and the like that comprise immunosuppressive placental stem cells, e.g., an immunosuppressive population of placental stem cells.

Placental stem cells provided herein can be seeded onto a natural matrix, e.g., a placental biomaterial such as an amniotic membrane material. Such an amniotic membrane material can be, e.g., amniotic membrane dissected directly from a mammalian placenta; fixed or heat-treated amniotic membrane, substantially dry (i.e., <20% $H_2O$) amniotic membrane, chorionic membrane, substantially dry chorionic membrane, substantially dry amniotic and chorionic membrane, and the like. Preferred placental biomaterials on which placental stem cells can be seeded are described in Hariri, U.S. Application Publication No. 2004/0048796.

Placental stem cells provided herein can be suspended in a hydrogel solution suitable for, e.g., injection. Suitable hydrogels for such compositions include self-assembling peptides, such as RAD16. In one embodiment, a hydrogel solution comprising the cells can be allowed to harden, for instance in a mold, to form a matrix having cells dispersed therein for implantation. Placental stem cells in such a matrix can also be cultured so that the cells are mitotically expanded prior to implantation. The hydrogel is, e.g., an organic polymer (natural or synthetic) that is cross-linked via covalent, ionic, or hydrogen bonds to create a three-dimensional open-lattice structure that entraps water molecules to form a gel. Hydrogel-forming materials include polysaccharides such as alginate and salts thereof, peptides, polyphosphazines, and polyacrylates, which are crosslinked ionically, or block polymers such as polyethylene oxide-polypropylene glycol block copolymers which are cross-linked by temperature or pH, respectively. In some embodiments, the hydrogel or matrix is biodegradable.

In some embodiments, the formulation comprises an in situ polymerizable gel (see, e.g., U.S. Patent Application Publication 2002/0022676; Anseth et al., *J. Control Release*, 78(1-3):199-209 (2002); Wang et al., *Biomaterials*, 24(22): 3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly(phosphazenes), poly(acrylic acids), poly (methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

The placental stem cells or co-cultures thereof can be seeded onto a three-dimensional framework or scaffold and implanted in vivo. Such a framework can be implanted in combination with any one or more growth factors, cells, drugs or other components that stimulate tissue formation or otherwise enhance or improve the practice of the methods of treatment described elsewhere herein.

Examples of scaffolds that can be used in the methods of treatment described herein include nonwoven mats, porous foams, or self assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly(ε-caprolactone)/poly(glycolic acid) (PCL/PGA) copolymer, formed by processes such as freeze-drying, or lyophilization (see, e.g., U.S. Pat. No. 6,355,699), can also be used as scaffolds.

In another embodiment, the scaffold is, or comprises, a nanofibrous scaffold, e.g., an electrospun nanofibrous scaffold. In a more specific embodiment, said nanofibrous scaffold comprises poly(L-lactic acid) (PLLA), type I collagen, a copolymer of vinylidene fluoride and trifluoroethylene (PVDF-TrFE), poly(-caprolactone), poly(L-lactide-co-ε-caprolactone) [P(LLA-CL)] (e.g., 75:25), and/or a copolymer of poly(3-hydroxybutyrate-co-3-hydroxyvalerate) (PHBV) and type I collagen. In another more specific embodiment, said scaffold promotes the differentiation of placental stem cells into chondrocytes. Methods of producing nanofibrous scaffolds, e.g., electrospun nanofibrous scaffolds, are known in the art. See, e.g., Xu et al., *Tissue Engineering* 10(7): 1160-1168 (2004); Xu et al., *Biomaterials* 25:877-886 (20040; Meng et al., *J. Biomaterials Sci., Polymer Edition* 18(1):81-94 (2007).

Placental stem cells described herein, e.g., immunosuppressive placental stem cells, can also be seeded onto, or contacted with, a physiologically-acceptable ceramic material including, but not limited to, mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS®, and mixtures thereof. Porous biocompatible ceramic materials currently commercially available include SURGIBONE® (CanMedica Corp., Canada), ENDOBON® (Merck Biomaterial France, France), CEROS® (Mathys, AG, Bettlach, Switzerland), and mineralized collagen bone grafting products such as HEALOS™ (DePuy, Inc., Raynham, Mass.) and VITOSS®, RHAKOSS™, and CORTOSS® (Orthovita, Malvern, Pa.). The framework can be a mixture, blend or composite of natural and/or synthetic materials.

In another embodiment, placental stem cells can be seeded onto, or contacted with, a felt, which can be, e.g., composed of a multifilament yarn made from a bioabsorbable material such as PGA, PLA, PCL copolymers or blends, or hyaluronic acid.

The placental stem cells described herein can, in another embodiment, be seeded onto foam scaffolds that may be composite structures. Such foam scaffolds can be molded into a useful shape, such as that of a portion of a specific structure in the body to be repaired, replaced or augmented. In some embodiments, the framework is treated, e.g., with 0.1M acetic acid followed by incubation in polylysine, PBS, and/or collagen, prior to inoculation of the immunosuppressive placental stem cells in order to enhance cell attachment. External surfaces of a matrix may be modified to improve the attachment or growth of cells and differentiation of tissue, such as by plasma-coating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the scaffold comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN™ (The Polymer Technology Group, Inc., Berkeley, Calif.). The scaffold can also comprise anti-thrombotic agents such as heparin; the scaffolds can also be treated to alter the surface charge (e.g., coating with plasma) prior to seeding with placental stem cells.

5.6.2 Genetically Modified Placental Stem Cells

In another aspect, provided herein are placental stem cells and umbilical cord stem cells that are genetically modified, e.g., to produce a nucleic acid or polypeptide of interest. Genetic modification can be accomplished, e.g., using virus-based vectors including, but not limited to, non-integrating replicating vectors, e.g., papilloma virus vectors, SV40 vectors, adenoviral vectors; integrating viral vectors, e.g., retrovirus vector or adeno-associated viral vectors; or replication-defective viral vectors. Other methods of introducing DNA into cells include the use of liposomes, electroporation, a particle gun, direct DNA injection, or the like.

Stem cells can be, e.g., transformed or transfected with DNA controlled by or in operative association with, one or more appropriate expression control elements, for example, promoter or enhancer sequences, transcription terminators, polyadenylation sites, internal ribosomal entry sites. Preferably, such a DNA incorporates a selectable marker. Following the introduction of the foreign DNA, engineered stem cells can be, e.g., grown in enriched media and then switched to selective media. In one embodiment, the DNA used to engineer a placental stem cell comprises a nucleotide sequence encoding a polypeptide of interest, e.g., a cytokine, growth factor, differentiation agent, or therapeutic polypeptide.

The DNA used to engineer the stem cell can comprise any promoter known in the art to drive expression of a nucleotide sequence in mammalian cells, e.g., human cells. For example, promoters include, but are not limited to, CMV promoter/enhancer, SV40 promoter, papillomavirus promoter, Epstein-Barr virus promoter, elastin gene promoter, and the like. In a specific embodiment, the promoter is regulatable so that the nucleotide sequence is expressed only when desired. Promoters can be either inducible (e.g., those associated with metallothionein and heat shock proteins) or constitutive.

In another specific embodiment, the promoter is tissue-specific or exhibits tissue specificity. Examples of such promoters include but are not limited to: myelin basic protein gene control region (Readhead et al., 1987, *Cell* 48:703) (oligodendrocyte cells); elastase I gene control region (Swit et al., 1984, *Cell* 38:639; Ornitz et al., 1986, *Cold Spring Harbor Symp. Quant. Biol.* 50:399; MacDonald, 1987, *Hepatology* 7:425) (pancreatic acinar cells); insulin gene control region (Hanahan, 1985, *Nature* 315:115) (pancreatic beta cells); myosin light chain-2 gene control region (Shani, 1985, *Nature* 314:283) (skeletal muscle).

Placental stem cells may be engineered to "knock out" or "knock down" expression of one or more genes. The expression of a gene native to a cell can be diminished by, for example, inhibition of expression by inactivating the gene completely by, e.g., homologous recombination. In one embodiment, for example, an exon encoding an important region of the protein, or an exon 5' to that region, is interrupted by a positive selectable marker, e.g., neo, preventing the production of normal mRNA from the target gene and resulting in inactivation of the gene. A gene may also be inactivated by creating a deletion in part of a gene or by deleting the entire gene. By using a construct with two regions of homology to the target gene that are far apart in the genome, the sequences intervening the two regions can be deleted (Mombaerts et al., 1991, *Proc. Nat. Acad. Sci. U.S.A.* 88:3084). Antisense, DNAzymes, small interfering RNA, and ribozyme molecules that inhibit expression of the target gene can also be used to reduce the level of target gene activity in the stem cells. For example, antisense RNA molecules which inhibit the expression of major histocompatibility gene complexes (HLA) have been shown to be most versatile with respect to immune responses. Triple helix molecules can be utilized in reducing the level of target gene activity. See, e.g., L. G. Davis et al. (eds), 1994, BASIC METHODS IN MOLECULAR BIOLOGY, 2nd ed., Appleton & Lange, Norwalk, Conn., which is incorporated herein by reference.

In a specific embodiment, placental or umbilical cord stem cells can be genetically modified with a nucleic acid molecule comprising a nucleotide sequence encoding a polypeptide of interest, wherein expression of the polypeptide of interest is controllable by an exogenous factor, e.g., polypeptide, small organic molecule, or the like. Such a polypeptide can be a therapeutic polypeptide. In a more specific embodiment, the polypeptide of interest is IL-12 or interleukin-1 receptor antagonist (IL-1Ra). In another more specific embodiment, the polypeptide of interest is a fusion of interleukin-1 receptor antagonist and dihydrofolate reductase (DHFR), and the exogenous factor is an antifolate, e.g., methotrexate. Such a construct is useful in the engineering of placental or umbilical cord stem cells that express IL-1Ra, or a fusion of IL-1Ra and DHFR, upon contact with methotrexate. Such a construct can be used, e.g., in the treatment of rheumatoid arthritis. In this embodiment, the fusion of IL-1Ra and DHFR is translationally upregulated upon exposure to an antifolate such as methotrexate. Therefore, in another specific embodiment, the nucleic acid used to genetically engineer a placental stem cell or umbilical cord stem cell can comprise nucleotide sequences encoding a first polypeptide and a second polypeptide, wherein said first and second polypeptides are expressed as a fusion protein that is translationally upregulated in the presence of an exogenous factor. The polypeptide can be expressed transiently or long-term (e.g., over the course of weeks or months).

Such a nucleic acid molecule can additionally comprise a nucleotide sequence encoding a polypeptide that allows for positive selection of engineered stem cells, or allows for visualization of the engineered stem cells. In another more specific embodiment, the nucleotide sequence encodes a polypeptide that is, e.g., fluorescent under appropriate visualization conditions, e.g., luciferase (Luc). In a more specific embodiment, such a nucleic acid molecule can comprise IL-1Ra-DHFR-IRES-Luc, where IRES is an internal ribosomal entry site.

5.6.3 Immortalized Placental Stem Cell Lines

Mammalian placental cells can be conditionally immortalized by transfection with any suitable vector containing a growth-promoting gene, that is, a gene encoding a protein that, under appropriate conditions, promotes growth of the transfected cell, such that the production and/or activity of the growth-promoting protein is regulatable by an external factor. In a preferred embodiment the growth-promoting gene is an oncogene such as, but not limited to, v-myc, N-myc, c-myc, p53, SV40 large T antigen, polyoma large T antigen, Ela adenovirus or E7 protein of human papillomavirus.

External regulation of the growth-promoting protein can be achieved by placing the growth-promoting gene under the control of an externally-regulatable promoter, e.g., a promoter the activity of which can be controlled by, for example, modifying the temperature of the transfected cells or the composition of the medium in contact with the cells. in one embodiment, a tetracycline (tet)-controlled gene expression system can be employed (see Gossen et al., *Proc. Natl. Acad. Sci. USA* 89:5547-5551, 1992; Hoshimaru et al., *Proc. Natl. Acad. Sci. USA* 93:1518-1523, 1996). In the absence of tet, a tet-controlled transactivator (tTA) within this vector strongly activates transcription from $ph_{CMV^{*}-1}$, a minimal promoter from human cytomegalovirus fused to tet operator sequences. tTA is a fusion protein of the repressor (tetR) of the transposon-10-derived tet resistance operon of *Escherichia coli* and the acidic domain of VP16 of herpes simplex virus. Low, non-toxic concentrations of tet (e.g., 0.01-1.0 µg/mL) almost completely abolish transactivation by tTA.

In one embodiment, the vector further contains a gene encoding a selectable marker, e.g., a protein that confers drug resistance. The bacterial neomycin resistance gene ($neo^R$) is one such marker that may be employed within the methods described herein. Cells carrying $neo^R$ may be selected by means known to those of ordinary skill in the art, such as the addition of, e.g., 100-200 µg/mL G418 to the growth medium.

Transfection can be achieved by any of a variety of means known to those of ordinary skill in the art including, but not limited to, retroviral infection. In general, a cell culture may be transfected by incubation with a mixture of conditioned medium collected from the producer cell line for the vector and DMEM/F12 containing N2 supplements. For example, a placental cell culture prepared as described above may be infected after, e.g., five days in vitro by incubation for about 20 hours in one volume of conditioned medium and two volumes of DMEM/F12 containing N2 supplements. Transfected cells carrying a selectable marker may then be selected as described above.

Following transfection, cultures are passaged onto a surface that permits proliferation, e.g., allows at least 30% of the cells to double in a 24 hour period. Preferably, the substrate is a polyornithine/laminin substrate, consisting of tissue culture plastic coated with polyornithine (10 µg/mL) and/or laminin (10 µg/mL), a polylysine/laminin substrate or a surface treated with fibronectin. Cultures are then fed every 3-4 days with growth medium, which may or may not be supplemented with one or more proliferation-enhancing factors. Proliferation-enhancing factors may be added to the growth medium when cultures are less than 50% confluent.

The conditionally-immortalized placental stem cell lines can be passaged using standard techniques, such as by trypsinization, when 80-95% confluent. Up to approximately the twentieth passage, it is, in some embodiments, beneficial to maintain selection (by, for example, the addition of G418 for cells containing a neomycin resistance gene). Cells may also be frozen in liquid nitrogen for long-term storage.

Clonal cell lines can be isolated from a conditionally-immortalized human placental stem cell line prepared as described above. In general, such clonal cell lines may be isolated using standard techniques, such as by limit dilution or using cloning rings, and expanded. Clonal cell lines may generally be fed and passaged as described above.

Conditionally-immortalized human placental stem cell lines, which may, but need not be, clonal, may generally be induced to differentiate by suppressing the production and/or activity of the growth-promoting protein under culture conditions that facilitate differentiation. For example, if the gene encoding the growth-promoting protein is under the control of an externally-regulatable promoter, the conditions, e.g., temperature or composition of medium, may be modified to suppress transcription of the growth-promoting gene. For the tetracycline-controlled gene expression system discussed above, differentiation can be achieved by the addition of tetracycline to suppress transcription of the growth-promoting gene. In general, 1 µg/mL tetracycline for 4-5 days is sufficient to initiate differentiation. To promote further differentiation, additional agents may be included in the growth medium.

5.6.4 Assays

Placental stem cells can be used in assays to determine the influence of culture conditions, environmental factors, molecules (e.g., biomolecules, small inorganic molecules. etc.) and the like on stem cell proliferation, expansion, and/or differentiation, compared to placental stem cells not exposed to such conditions.

In one embodiment, placental stem cells can be assayed for changes in proliferation, expansion or differentiation upon contact with a molecule. In one embodiment, for example, provided herein is a method of identifying a compound that modulates the proliferation of a plurality of placental stem cells, comprising contacting said plurality of stem cells with said compound under conditions that allow proliferation, wherein if said compound causes a detectable change in proliferation of said plurality of stem cells compared to a plurality of stem cells not contacted with said compound, said compound is identified as a compound that modulates proliferation of placental stem cells. In a specific embodiment, said compound is identified as an inhibitor of proliferation. In another specific embodiment, said compound is identified as an enhancer of proliferation.

In another embodiment, compounds can be identified that modulate the expansion of a plurality of placental stem cells, comprising contacting said plurality of stem cells with said compound under conditions that allow expansion, wherein if said compound causes a detectable change in expansion of said plurality of stem cells compared to a plurality of stem cells not contacted with said compound, said compound is identified as a compound that modulates expansion of placental stem cells. In a specific embodiment, said compound is identified as an inhibitor of expansion. In another specific embodiment, said compound is identified as an enhancer of expansion.

In another embodiment, a compound that modulates the differentiation of a placental stem cell can be identified by a method comprising contacting said stem cells with said compound under conditions that allow differentiation, wherein if said compound causes a detectable change in differentiation of said stem cells compared to a stem cell not contacted with said compound, said compound is identified as a compound that modulates proliferation of placental stem cells. In a specific embodiment, said compound is identified as an inhibitor of differentiation. In another specific embodiment, said compound is identified as an enhancer of differentiation.

5.6.5 Placental Stem Cell Bank

Stem cells from postpartum placentas can be cultured in a number of different ways to produce a set of lots, e.g., a set of individually-administrable doses, of placental stem cells. Such lots can, for example, be obtained from stem cells from placental perfusate or from enzyme-digested placental tissue. Sets of lots of placental stem cells, obtained from a plurality of placentas, can be arranged in a bank of placental stem cells for, e.g., long-term storage. Generally, adherent stem cells are obtained from an initial culture of placental material to form a seed culture, which is expanded under controlled conditions to form populations of cells from approximately equivalent numbers of doublings. Lots are preferably derived from the tissue of a single placenta, but can be derived from the tissue of a plurality of placentas.

In one embodiment, stem cell lots are obtained as follows. Placental tissue is first disrupted, e.g., by mincing, digested with a suitable enzyme, e.g., collagenase (see Section 5.2.3, above). The placental tissue preferably comprises, e.g., the entire amnion, entire chorion, or both, from a single placenta, but can comprise only a part of either the amnion or chorion. The digested tissue is cultured, e.g., for about 1-3 weeks, preferably about 2 weeks. After removal of non-adherent cells, high-density colonies that form are collected, e.g., by trypsinization. These cells are collected and resuspended in a convenient volume of culture medium, and defined as Passage 0 cells.

Passage 0 cells are then used to seed expansion cultures. Expansion cultures can be any arrangement of separate cell culture apparatuses, e.g., a Cell Factory by NUNC™. Cells in the Passage 0 culture can be subdivided to any degree so as to seed expansion cultures with, e.g., $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $1\times10^4$, $2\times10^4$, $3\times10^4$, $4\times10^4$, $5\times10^4$, $6\times10^4$, $7\times10^4$, $8\times10^4$, $9\times10^4$, or $10\times10^4$ stem cells. Preferably, from about $2\times10^4$ to about $3\times10^4$ Passage 0 cells are used to seed each expansion culture. The number of expansion cultures can depend upon the number of Passage 0 cells, and may be greater or fewer in number depending upon the particular placenta(s) from which the stem cells are obtained.

Expansion cultures are grown until the density of cells in culture reaches a certain value, e.g., about $1\times10^5$ cells/cm². Cells can either be collected and cryopreserved at this point, or passaged into new expansion cultures as described above. Cells can be passaged, e.g., 2, 3, 4, 5, 6, 7, 8, 9, 10, 11, 12, 13, 14, 15, 16, 17, 18, 19 or 20 times prior to use. A record of the cumulative number of population doublings is preferably maintained during expansion culture(s). The cells from a Passage 0 culture can be expanded for 2, 3, 4, 5, 6, 7, 8, 9, 10, 12, 14, 16, 18, 20, 22, 24, 26, 28, 30, 32, 34, 36, 38 or 40 doublings, or up to 60 doublings. Preferably, however, the number of population doublings, prior to dividing the population of cells into individual doses, is between about 15 and about 30, preferably about 20 doublings. The cells can be culture continuously throughout the expansion process, or can be frozen at one or more points during expansion.

Cells to be used for individual doses can be frozen, e.g., cryopreserved for later use. Individual doses can comprise, e.g., about 1 million to about 100 million cells per ml, and can comprise between about $10^6$ and about $10^9$ cells in total.

In a specific embodiment, of the method, Passage 0 cells are cultured for approximately 4 doublings, then frozen in a first cell bank. Cells from the first cell bank are frozen and used to seed a second cell bank, the cells of which are expanded for about another eight doublings. Cells at this stage are collected and frozen and used to seed new expansion cultures that are allowed to proceed for about eight additional doublings, bringing the cumulative number of cell doublings to about 20. Cells at the intermediate points in passaging can be frozen in units of about 100,000 to about 10 million cells per ml, preferably about 1 million cells per ml for use in subsequent expansion culture. Cells at about 20 doublings can be frozen in individual doses of between about 1 million to about 100 million cells per ml for administration or use in making a stem cell-containing composition. In one embodiment, the cells are diluted to about 2 million/ml in 10% HAS, 10% DMSO in Plasmalyte.

In a preferred embodiment, the donor from which the placenta is obtained (e.g., the mother) is tested for at least one pathogen. If the mother tests positive for a tested pathogen, the entire lot from the placenta is discarded. Such testing can be performed at any time during production of placental stem cell lots, including before or after establishment of Passage 0 cells, or during expansion culture. Pathogens for which the presence is tested can include, without limitation, hepatitis A, hepatitis B, hepatitis C, hepatitis D, hepatitis E, human immunodeficiency virus (types I and II), cytomegalovirus, herpesvirus, and the like.

5.6.6 Treatment of Diseases

Provided herein are methods of treating an individual having a disease, disorder or condition, wherein the disease, disorder or condition is caused by, or is associated with, an inappropriate or undesirable immune response, e.g., a disease, disorder or condition that can be treated beneficially by immunosuppression, comprising administering to the individual placental stem cells. In a specific embodiment, the amount is an amount sufficient to detectably suppress an immune response in the individual. Such an immune response can be, e.g., proliferation of T cells in an MLR or regression assay performed using T cells from the individual.

An individual having a disease, disorder or condition associated with or caused by an inappropriate or undesirable immune response, e.g., an individual having, or at risk of developing multiple sclerosis; a person having, or at risk of developing, an inflammatory bowel disease, e.g., Crohn's disease or ulcerative colitis; a person having or at risk of developing graft-versus-host disease; a person having or at risk of developing scleroderma; a person having or at risk of developing rheumatoid arthritis; a person having or at risk of developing diabetes; a person having or at risk of developing psoriasis; a person having or at risk of developing mycosis fungoides; and the like, can be treated with a plurality of placental stem cells, and, optionally, one or more therapeutic agents, at any time during the progression of the disease. For example, the individual can be treated immediately after diagnosis, or within 1, 2, 3, 4, 5, 6 days of diagnosis, or within 1, 2, 3, 4, 5, 6, 7, 8, 9, 10, 15, 20, 25, 30, 35, 40, 45, 50 or more weeks, or 1, 2, 3, 4, 5, 6, 7, 8, 9, 10 or more years after diagnosis. The individual can be treated once, or multiple times during the clinical course of the disease. The individual can be treated, as appropriate, during an acute attack, during remission, or during a chronic degenerative phase.

The placenta stem cells useful in the treatment of such a disease, disorder or condition can be any of the placental stem cells disclosed herein. In a specific embodiment, the placental stem cells express CD200 and HLA-G; express CD73, CD105, and CD200; express CD200 and OCT-4; express CD73, CD105 and HLA-G; express CD73 and CD105, and facilitate the formation of one or more embryoid-like bodies in a population of placental cells when said population is cultured under conditions that allow for the formation of embryoid-like bodies; or express OCT-4, and (c) facilitate the formation of one or more embryoid-like bodies in a population of placental cells when said population is cultured under conditions that allow for the formation of embryoid-like bodies; or any combination of the foregoing. In a specific embodiment, the placental stem cells are $CD10^+$, $CD105^+$, $CD200^+$, $CD34^-$ placental stem cells. In another specific embodiment, the placental stem cells are $CD117^-$.

In one embodiment, the individual is administered a dose of about 300 million placental stem cells. Dosage, however, can vary according to the individual's physical characteristics, e.g., weight, and can range from 1 million to 10 billion placental stem cells per dose, preferably between 10 million and 1 billion per dose, or between 100 million and 50 million placental stem cells per dose. The administration is preferably intravenous, but can be by any medically-acceptable route for the administration of live cells, e.g., parenterally, subcutaneously, intramuscularly, intraperitoneally, intraocularly, and the like. In one embodiment, the placental stem cells are from a cell bank. In one embodiment, a dose of placental stem cells, e.g., from amnion, amnion/chorion, chorion or umbilical cord, is contained within a blood bag or similar bag, suitable for bolus injection or administration by catheter.

In another embodiment, provided herein is a method of treating an individual having a disease, disorder or condition, wherein the disease, disorder or condition is caused by, or is associated with, an inappropriate or undesirable immune response, e.g., a disease, disorder or condition that can be treated beneficially by immunosuppression, comprising administering to the individual culture medium that has been conditioned placental stem cells, in an amount sufficient to detectably suppress an immune response in the individual. Such an immune response can be, e.g., proliferation of T cells in an MLR or regression assay performed using T cells from the individual.

Placental stem cells or umbilical cord stem cells, or medium conditioned by placental stem cells or umbilical cord stem cells, can be administered in a single dose, or in multiple doses. Where placental stem cells are administered in multiple doses, the doses can be part of a therapeutic regimen designed to relieve one or more acute symptoms of disease, disorder or condition, wherein the disease, disorder or condition is caused by, or is associated with, an inappropriate or undesirable immune response, or can be part of a long-term therapeutic regimen designed to prevent, or lessen the severity, of a chronic course of such a disease, disorder or condition.

5.6.7 Treatment of Multiple Sclerosis

In another aspect, provided herein is a method of treating an individual having multiple sclerosis, or a symptom associated with multiple sclerosis, comprising administering to the individual a plurality of placental stem cells, or medium conditioned by placental stem cells, in an amount and for a time sufficient to detectably modulate, e.g., suppress an immune response in the individual.

Multiple sclerosis (MS) is a chronic, recurrent inflammatory disease of the central nervous system. The disease results in injury to the myelin sheaths surrounding CNS and PNS axons, oligodendrocytes, and the nerve cells themselves. The disease is mediated by autoreactive T cells, particularly $CD4^+$ T cells, that proliferate, cross the blood-brain barrier, and enter the CNS under the influence of cellular adhesion molecules and pro-inflammatory cytokines. The symptoms of MS include sensory disturbances in the limbs, optic nerve dysfunction, pyramidal tract dysfunction, bladder dysfunction, bowel dysfunction, sexual dysfunction, ataxia, and diplopia.

Four different types or clinical courses of MS have been identified. The first, relapsing/remitting MS (RRMS) is characterized by self-limiting attacks of neurological dysfunction that manifest acutely, over the course of days to weeks, followed by a period of recovery, sometimes incomplete, over several months. The second type, secondary progressive MS (SPMS), begins as RRMS but changes such that the clinical course becomes characterized by a steady deterioration in function unrelated to acute attacks. The third, primary progressive MS (PPMS), is characterized by a steady decline in function from onset, with no acute attacks. The fourth type, progressive/relapsing MS (PRMS), also begins with a progressive course, with occasional attacks superimposed on the progressive decline in function.

Persons having MS are generally evaluated using a motor skills assessment, optionally with an MRI. For example, one motor skills assessment, the expanded disability status scale, scores gradations in an affected individual's abilities, as follows:

| | |
|---|---|
| 0.0 | Normal neurological examination |
| 1.0 | No disability, minimal signs in one FS |
| 1.5 | No disability, minimal signs in more than one FS |
| 2.0 | Minimal disability in one FS |
| 2.5 | Mild disability in one FS or minimal disability in two FS |
| 3.0 | Moderate disability in one FS, or mild disability in three or four FS. Fully ambulatory. |
| 3.5 | Fully ambulatory but with moderate disability in one FS and more than minimal disability in several others |
| 4.0 | Fully ambulatory without aid, self-sufficient, up and about some 12 hours a day despite relatively severe disability; able to walk without aid or rest some 500 meters |
| 4.5 | Fully ambulatory without aid, up and about much of the day, able to work a full day, may otherwise have some limitation of full activity or require minimal assistance; characterized by relatively severe disability; able to walk without aid or rest some 300 meters. |
| 5.0 | Ambulatory without aid or rest for about 200 meters; disability severe enough to impair full daily activities (work a full day without special provisions) |
| 5.5 | Ambulatory without aid or rest for about 100 meters; disability severe enough to preclude full daily activities |
| 6.0 | Intermittent or unilateral constant assistance (cane, crutch, brace) required to walk about 100 meters with or without resting |
| 6.5 | Constant bilateral assistance (canes, crutches, braces) required to walk about 20 meters without resting |
| 7.0 | Unable to walk beyond approximately five meters even with aid, essentially restricted to wheelchair; wheels self in standard wheelchair and transfers alone; up and about in wheelchair some 12 hours a day |
| 7.5 | Unable to take more than a few steps; restricted to wheelchair; may need aid in transfer; wheels self but cannot carry on in standard wheelchair a full day; May require motorized wheelchair |
| 8.0 | Essentially restricted to bed or chair or perambulated in wheelchair, but may be out of bed itself much of the day; retains many self-care functions; generally has effective use of arms |
| 8.5 | Essentially restricted to bed much of day; has some effective use of arms retains some self care functions |
| 9.0 | Confined to bed; can still communicate and eat. |
| 9.5 | Totally helpless bed patient; unable to communicate effectively or eat/swallow |
| 10.0 | Death due to MS |

In the above scoring system, "FS" refers to the eight functional systems measured, including pyramidal, cerebellar, brainstem, sensory, bowel and bladder, visual, cerebral, and other systems.

Other, similar scoring systems are known, including the Scripps neurological rating scale, the ambulatory index, and the multiple sclerosis functional composite score (MSFC).

The progress of MS has also been assessed by a determination of the attack rate.

The progress of MS has also been assessed by magnetic resonance imaging, which can detect neural lesions associated with MS (e.g., new lesions, enhancing lesions, or combined unique active lesions).

Thus, in one embodiment, provided herein is a method of treating an individual having MS, e.g., and individual who has been diagnosed with MS, comprising administering to the individual a plurality of placental stem cells sufficient to detectably suppress an immune response in the individual. In a specific embodiment, the MS is relapsing/remitting MS. In another specific embodiment, the MS is secondary progressive MS. In another specific embodiment, the MS is primary progressive MS. In another specific embodiment, the MS is progressive/relapsing MS. In another specific embodiment, the administering detectably improves one or more symptoms of MS in the individual. In more specific embodiments, the symptom is, e.g., one or more of a sensory disturbance in the limbs, an optic nerve dysfunction, a pyramidal tract dysfunction, a bladder dysfunction, a bowel dysfunction, a sexual dysfunction, ataxia, or diplopia. In another specific embodiment, said administering results in an improvement on the EDSS scale of at least one half point. In another specific embodiment, said administering results in the maintenance of function, according to at least one MS scoring system, over the course of, e.g., 1, 2, 3, 4, 5, 6, 7, 8, 9, 10, or 11 months, In another specific embodiment, said administering results in an improvement on the EDSS scale of at least one point. In another specific embodiment, said administering results in an improvement on the EDSS scale of at least two points. In other specific embodiments, said administering results in a detectable improvement on a multiple sclerosis assessment scale or on an MRI. The individual can be treated, as appropriate, during an acute attack, during remission, or during a chronic degenerative phase. In another embodiment, the placental stem cells are administered to a female having MS, post-partum, to maintain the state of remission or reduced occurrence of relapse experienced during pregnancy.

Also provided herein are methods for the treatment of an individual having MS, e.g., an individual who has been diagnosed as having MS, comprising administering to the individual a plurality of placental stem cells sufficient to detectably suppress an immune response in the individual, wherein the administering detectably improves one or more symptoms of MS in the individual, and one or more therapeutic agents. In one embodiment, the therapeutic agent is a glucocorticoid. In specific embodiments, the glucocorticoid is adrenocorticotropic hormone (ACTH), methylprednisolone, or dexamethasone. In another embodiment, the therapeutic agent is an immunomodulatory or immunosuppressive agent. In various specific embodiments, the immunomodulatory or immunosuppressive agent is IFNβ-1a, IFN-1b, glatiramer acetate, cyclophosphamide, methotrexate, azathioprine, cladribine, cyclosporine or mitoxantrone. In other embodiments, the therapeutic agent is intravenous immunoglobulin, plasma exchange, or sulfasalazine. In another embodiment, the individual is administered any combination of the foregoing therapeutic agents.

5.6.8 Treatment of Inflammatory Bowel Disease

In one embodiment, placental stem cells, placental stem cell populations, and/or compositions comprising placental stem cells or placental stem cell populations, are used to treat an individual having, or at risk of developing, inflammatory bowel disease (IBD), e.g., Crohn's disease or ulcerative colitis. Thus, in another aspect, provided herein is a method of treating an individual having inflammatory bowel disease, or a symptom associated with inflammatory bowel disease, comprising administering to the individual a plurality of placental stem cells, or medium conditioned by placental stem cells, in an amount and for a time sufficient to detectably modulate, e.g., suppress an immune response in the individual.

Crohn's Disease. In one embodiment, the IBD is Crohn's disease, sometimes referred to as ileitis or enteritis. Crohn's disease is a chronic disorder that causes inflammation of the digestive tract (also referred to as the gastrointestinal, or GI, tract). Crohn's disease can affect any part of the GI tract, from mouth to anus, but most commonly affects the lower part of the small intestine, referred to as the ileum. Five types of Crohn's disease are known. Gastroduodenal Crohn's disease affects the stomach and duodenum (the highest portion of the small intestine). Jejunoileitis is Crohn's disease of the jejunum, the longest portion of the small intestine. Ileitis is Crohn's disease of the ileum, the lower portion of the small intestine. Ileocolitis, the most common form of Crohn's disease, affects the ileum and colon. Finally, Crohn's colitis (Granulomatous colitis) affects the colon, and is distinguished from ulcerative colitis in that in Crohn's colitis, there are often areas of healthy tissue between areas of diseased tissue, and Crohn's colitis can involve only the colon, without involving the rectum. Crohn's disease is thought to arise from inappropriate reaction of the body's immune system to antigens in the GI tract, including, e.g., food, beneficial bacteria, etc., resulting in an accumulation of white blood cells in the lining of the intestines. Inflammation associated with Crohn's disease has also been attributed to the action of the cytokine tumor necrosis factor (TNF-α).

Ulcerative colitis. In another embodiment, the IBD is ulcerative colitis. Ulcerative colitis is a disease that causes inflammation and sores (ulcers) in the lining of the rectum and/or colon. Ulcers form where inflammation has killed the cells that usually line the colon; the ulcers typically subsequently bleed and produce pus. When inflammation occurs in the rectum and lower part of the colon, the disease is referred to as ulcerative proctitis. If the entire colon is affected, the disease is called pancolitis. If only the left side of the colon is affected, the disease is referred to as limited or distal colitis. Symptoms of ulcerative colitis include, but are not limited to, abdominal pain, bloody diarrhea, fevers, nausea, abdominal cramps, anemia, fatigue, weight loss, loss of appetite, rectal bleeding, loss of bodily fluids and nutrients, skin lesions, joint pain, and growth failure (in children). Ulcerative colitis can also cause complications such as inflammation of the eye, liver disease, and osteoporosis.

Thus, in one embodiment, provided herein is a method of treating an individual having an inflammatory bowel disease, comprising administering a therapeutically effective amount of placental stem cells to said individual, wherein said therapeutically effective amount is an amount that results in a detectable improvement in at least one symptom of said inflammatory bowel disease (IBD). In a specific embodiment, the IBD is Crohn's disease. In a more specific embodiment, said Crohn's disease is gastroduodenal Crohn's disease, jejunoileitis, ileitis, ileocolitis, or Crohn's colitis. In another more specific embodiment, said symptom is a symptom of Crohn's disease. In a more specific embodiment, said symptom of Crohn's disease is inflammation and swelling of a part of the GI tract, abdominal pain, frequent emptying of the bowel, and/or diarrhea. In another more specific embodiment, said symptom of Crohn's disease is rectal bleeding, anemia, weight loss, arthritis, skin problems, fever, thickening of the intestinal wall, formation of scar tissue in the intestines, formation of sores or ulcers in the intestine, development of one or more fistulas in the intestinal wall, development of one or more fissures in the anus, development of nutritional deficiencies (e.g., deficiencies in one or more of proteins, calories, vitamins), development of kidney stones, development of gallstones, or diseases of the liver or biliary system.

In another more specific embodiment, the IBD is ulcerative colitis. In a more specific embodiment, said ulcerative colitis is ulcerative proctitis, pancolitis, limited colitis or distal colitis. In another more specific embodiment, said symptom is a symptom of ulcerative colitis. In a more specific embodiment, said symptom is abdominal pain, bloody diarrhea, fevers, nausea, abdominal cramps, anemia, fatigue, weight loss, loss of appetite, rectal bleeding, loss of bodily fluids and nutrients, skin lesions, joint pain, and growth failure. In another more specific embodiment, the symptom is osteoporosis, eye inflammation, or liver disease.

In another specific embodiment, said individual to whom placental stem cells are administered is additionally administered one or more of a second therapy, wherein said second therapy comprises an anti-inflammatory agent, steroid, immune suppressor, and/or an antibiotic. Examples of anti-inflammatory drugs useful in the treatment of Crohn's disease or ulcerative colitis include, but are not limited to, mesalamine, 5-ASA (5-aminosalicylic acid) agents (e.g., ASACOL® (mesalamine, delayed-release), DIPENTUM (Osalazine), PENTASA® (mesalamine controlled-release)), sulfasalazine (a combination of 5-ASA and sulfapyridine), anti-inflammatory antibodies (e.g., Infliximab (REMI-CADE®)), and the like. Examples of steroids useful in the treatment of Crohn's disease or ulcerative colitis include, but are not limited to, cortisone, hydrocortisone, prednisone, methylprednisone, and the like. Typically, as practiced in the art, the dosage of steroid is first delivered in a relatively large dose, followed by smaller dosages as inflammation subsides. Examples of immune suppressors useful in the treatment of Crohn's disease include, but are not limited to, cyclosporine A, 6-mercaptopurine or azathioprine. Any antibiotic can be used in the treatment of Crohn's disease, including, e.g., ampicillin, sulfonamide, cephalosporin, tetracycline, and/or metronidazole. In another specific embodiment, the second therapy is an administration of porcine whipworms, e.g., ova of *Trichuris suis*.

5.6.9 Treatment of Graft Versus Host Disease

In another embodiment, provided herein is a method of treating an individual, e.g., a transplant recipient or individual who will receive a transplant, that has, or is experiencing a symptom of, or is at risk for developing, graft-versus-host disease (GVHD), comprising administering to the individual a therapeutically effective amount of placental stem cells, or culture medium conditioned by placental stem cells, wherein the therapeutically effective amount is an amount sufficient to cause a detectable improvement in one or more symptoms of GVHD, or sufficient to detectably reduce the onset of one or more symptoms of GVHD GVHD typically develops after, or as the result of, fully- or partially-allogeneic tissue transplantation, particularly after allogeneic hematopoietic stem cell transplantation, and can include one or more of dermatitis, enteritis and hepatitis that develops typically within 5-100 days of transplantation. GVHD can be acute or chronic. Acute GVHD may be characterized by the appearance of a pruritic or painful rash, typically by day 5 to 47 after transplantation. Hyperacute GVHD may also be accompanied by fever, generalized erythroderma, and desquamation. The liver may also become involved, as evidenced by raised (e.g., higher than normal) levels of bilirubin, alanine aminotransferase (ALT), aspartate aminotransferase (AST), and alkaline phosphatase (AP). Acute GVHD can also involve the colon, resulting in diarrhea, internal bleeding, cramping, abdominal pain, and ileus. Chronic GVHD can occur in transplant patients who have experienced acute GVHD, or who were previously asymptomatic. Manifestations of chronic GVHD include a burning sensation in the eye, eye irritation, photophobia, and eye pain due to decreased tear secretion; dryness of the mouth, sensitivity to spicy or acidic foods, abdominal pain, dysphagia (difficulty in swallowing), odynophagia (pain on swallowing), weight loss, obstructive lung disease, muscular weakness, neuropathic pain, and/or muscle cramps.

Therefore, in specific embodiments of the method, the therapeutically effective amount of placental stem cells is an amount sufficient to cause a detectable improvement in one or more symptoms of acute GVHD, or sufficient to detectably reduce the onset of one or more symptoms of acute GVHD. In more specific embodiments, said one or more symptoms comprise dermatitis, pruritic skin, rash, enteritis, hepatitis, fever, erythroderma, desquamation, a raised level of ALT, a raised level of AST, a raised level of AP; a raised level of Bilirubin; abdominal pain, cramping, internal bleeding, or ileus. In another specific embodiment of the method, the therapeutically effective amount of placental stem cells is an amount sufficient to cause a detectable improvement in one or more symptoms of chronic GVHD, or sufficient to detectably reduce the onset of one or more symptoms of chronic GVHD, where said one or more symptoms comprise a burning sensation in the eye, eye irritation, decreased tear production, photophobia, eye pain due to decreased tear secretion dryness of the mouth, sensitivity to spicy or acidic foods, abdominal pain, dysphagia (difficulty in swallowing), odynophagia (pain on swallowing), weight loss, obstructive lung disease (including any of wheezing dyspnea and/or chronic coughing), muscular weakness, neuropathic pain, and/or muscle cramps. In other specific embodiments of the method, symptoms of acute GVHD and/or chronic GVHD comprise hyperbilirubinemia, jaundice, portal hypertension, cirrhosis, hemorrhagic conjunctivitis, psudomembrane formation, lagophthalmos, chronic keratoconjunctivitis, sicca, punctuate keratopathy, atrophy of the oral mucosa, erythema, development of lichenoid lesions of the buccal or labial mucosae, bronchiolitis obliterans, vaginitis, vaginal strictures, autoimmune thrombocytopenia, and/or anemia.

The method is not limited by the nature of the donor or recipient. Transplantation can cross species lines. In preferred embodiments, the donor and recipient are the same species, e.g., are both human. The transplant recipient can be fully- or partially-allogeneic to the donor. The transplantation can be autologous. Transplant recipients or donors can be less than five years of age, from 1 to 10 years of age, from 5 to 15 years of age, from 10 to 20 years of age, from 15 to 25 years of age, from 20 to 30 years of age, from 25 to 35 years of age, from 30 to 40 years of age, from 35 to 45 years of age, from 40 to 50 years of age, from 45 to 55 years of age, from 50 to 60 years of age, from 55 to 65 years of age, from 60 to 70 years of age, or 70 years of age or older.

GVHD is generally graded by severity of symptoms. For example, in one embodiment, symptoms of GVHD are staged, and GVHD is graded from 0 (no GVHD)—IV (life-threatening GVHD) according to skin, liver, and/or intestinal symptoms, as shown in Tables 1 and 2:

TABLE 1

Staging of Acute Graft-Versus-Host Disease

| Stage | Skin | Liver (Bilirubin Level, mg/dL) | Intestine |
| --- | --- | --- | --- |
| + | Maculopapular rash on <25% of body surface | 2-3 | Diarrhea 500-1000 mL/d or persistent nausea |
| ++ | Maculopapular rash on 25-50% of body surface | 3-6 | Diarrhea 1000-1500 mL/d |
| +++ | Generalized erythroderma | 6-15 | Diarrhea >1500 mL/d |
| ++++ | Desquamation and bullae | >15 | Pain with or without ileus |

TABLE 2

Grading of Acute GVHD

| | Stage | | | |
| --- | --- | --- | --- | --- |
| Overall Grade | Skin | Liver | Gut | Functional Impairment |
| 0 (None) | 0 | 0 | 0 | 0 |
| I (Mild) | + to ++ | 0 | 0 | 0 |
| II (Moderate) | + to +++ | + | + | + |
| III (Severe) | ++ to +++ | ++ to +++ | ++ to +++ | ++ |
| IV (Life threatening) | ++ to ++++ | ++ to ++++ | ++ to ++++ | +++ |

Thus, in another embodiment of the method, the therapeutically effective amount of placental stem cells is an amount sufficient to cause an improvement in one or more symptoms of graft-versus-host disease, e.g., in an individual, e.g., an individual that has received a transplant (transplant recipient), such that said graft-versus-host disease is reduced in grade by at least one step. In specific embodiments, said graft-versus-host disease is reduced from grade IV to grade III; from grade IV to grade II; from grade IV to grade I; from grade IV to grade 0; from grade III to grade II; from grade III to grade I; from grade III to grade 0; from grade II to grade I; from grade II to grade 0; or from grade I to grade 0. In another embodiment of the method, the therapeutically effective amount of placental stem cells is an amount such that graft-versus-host disease in said individual does not develop past grade 0, grade I, grade II or grade II within 10, 20, 30, 40, 50, 60, 70, 80, 90, or 100 days post-transplantation.

In various specific embodiments, the individual having, or who is at risk for developing, GVHD are individuals receiving allogeneic hematopoietic cell transplants (e.g., individuals receiving no GVHD prophylaxis; older individuals; recipients of HLA-nonidentical hematopoietic stem cells; recipients of grafts from allosensitized donors; recipients of grafts from unrelated donors); individuals receiving solid organ transplants, particularly transplants of organs comprising lymphoid tissue, e.g., small bowel transplants; and individuals receiving unirradiated blood products (e.g., neonates and fetuses, individuals having congenital immunodeficiency syndromes, individuals receiving immunosuppressive chemotherapy, individuals receiving directed blood donations from partially HLA-identical, HLA-homologous donors), individuals receiving composite tissue allografts (that is, allografts having more than one tissue type); and the like. GVHD can also occur after autologous or syngeneic hematopoietic cell transplantation. In another specific embodiment, the individual has received radiation (e.g., has been irradiated) at a sub-lethal or lethal dose as an adjunct to transplantation.

In specific embodiments, the placental or umbilical cord stem cells are administered to the individual within 14, 13, 12, 11, 10, 9, 8, 7, 6, 5, 4, 3, 2 or 1 day prior to transplantation. In another specific embodiment, the placental or umbilical cord stem cells are administered concurrently with transplantation. In another specific embodiment, the placental or umbilical cord stem cells are administered within 1, 2, 3, 4, 5, 6, 7, 8, 9, 10, 11, 12, 13 or 14 days of transplantation. Administration of the placental or umbilical cord stem cells can be performed multiple times, e.g., multiple times before, with or after transplantation, or any combination thereof. In another embodiment, umbilical cord or placental stem cells are administered at any time post-transplantation when graft-versus-host disease of Grade II or worse is manifested in the individual (transplant recipient).

In another embodiment of the method, the individual, e.g., transplant recipient or an individual who will receive a transplant, is administered placental stem cells or umbilical cord stem cells and additionally at least one other therapeutic agent. In a specific embodiment, the therapeutic agent is athymocyte globulin, mycophenolate mofetil, sirolimus, Campath-1H, keratinocyte growth factor (KGF), suberoylanilide hydroxamic acid (SAHA), cortisone, hydrocortisone, prednisone, or methylprednisone. In another specific embodiment, the therapeutic agent is an immunosuppressive agent or immunomodulatory agent. Immunosuppressive agents and immunomodulatory agents applicable to GVHD are known in the art and include, but are not limited to, methothrexate, leflunomide, cyclophosphamide, cyclosporine A, macrolide antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators. peptide mimetics, and antibodies (e.g., human, humanized, chimeric, monoclonal, polyclonal, Fvs, ScFvs, Fab or F(ab)$_2$ fragments or epitope binding fragments), nucleic acid molecules (e.g., antisense nucleic acid molecules and triple helices), small molecules, organic compounds, and inorganic compounds. In particular, immunomodulatory agents include, but are not limited to, methothrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators. Examples of T cell receptor modulators include, but are not limited to, anti-T cell receptor antibodies (e.g., anti-CD4 antibodies (e.g., cM-T412 (Boeringer), IDEC-CE9. Is (IDEC and SKB), mAB 4162W94, ORTHOCLONE® and OKTcdr4a (Janssen-Cilag)), anti-CD3 antibodies (e.g., NUVION® (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH® 1H (Ilex)), anti-CD2 antibodies, anti-CD1a antibodies (e.g., Xanelim (Genentech)), and anti-B7 antibodies (e.g., IDEC-114) (IDEC))), CTLA4-immunoglobulin, thalidomide, or one of the compounds in Section 5.6.6, above. In a specific embodiment, a T cell receptor modulator is a CD2 antagonist. In other embodiments, a T cell receptor modulator is not a CD2 antagonist. In another specific embodiment, the agent is antibody MEDI-501 (T10B9). In another specific embodiment, a T cell receptor modulator is a CD2 binding molecule, preferably MEDI-507. In other embodiments, a T cell receptor modulator is not a CD2 binding molecule. Any combination of the above therapeutic agents, suitable for treatment of GVHD or a symptom of GVHD, can be administered. Such therapeutic agents can be administered in any combination with the placental stem cells or umbilical cord stem cells, at the same time or as a separate course of treatment.

5.6.10 Treatment of Rheumatoid Arthritis

In another embodiment, provided herein is a method of treating an individual that has, or is experiencing a symptom of, or is at risk for developing, rheumatoid arthritis (RA), comprising administering to the individual a therapeutically effective amount of placental stem cells or umbilical cord stem cells, or culture medium conditioned by placental stem cells or umbilical cord stem cells, wherein the therapeutically effective amount is an amount sufficient to cause a detectable improvement in one or more symptoms of RA, or sufficient to detectably reduce the onset of one or more symptoms of RA. Rheumatoid arthritis is a chronic, inflammatory autoimmune condition in which the body's immune system attacks the joints, and, typically, other tissues of the body.

In a specific embodiment, the administration is sufficient to cause a detectable improvement in one or more symptoms of RA, or sufficient to detectably reduce the onset of one or more symptoms of RA, in at least one joint in the individual with RA. In another specific embodiment, the administration is sufficient to cause a detectable improvement in one or more symptoms of RA, or sufficient to detectably reduce the onset of one or more symptoms of RA, in at least one non-joint tissue in the individual with RA. Examples of non-joint tissue that can be affected by RA include, but are not limited to, skin (dermis), lungs, autoimmune system or blood, renal tissue, cardiovascular tissue, ocular tissue, or neurological tissue.

In specific embodiments, the symptom of RA is, without limitation, morning stiffness (e.g., an hour in duration), soft-tissue swelling of one or more joints or joint groups, joint pain, subcutaneous nodules, rheumatoid factor present at above $95^{th}$ percentile, or radiological changes suggestive of joint erosion.

In a specific embodiment, the administration is sufficient to cause a detectable improvement in one or more conditions adjunct to RA, or sufficient to detectably reduce the onset of one or more conditions adjunct to RA. Examples of such conditions include, but are not limited to, pyoderma gangrenosum, neutrophilic dermatosis, Sweet's syndrome, viral infection, erythema nodosum, lobular panniculitis, atrophy of digital skin, palmar erythema, diffuse thinning (rice paper skin), skin fragility, subcutaneous nodules on an exterior surface, e.g., on the elbows, fibrosis of the lungs (e.g., as a consequence of methotrexate therapy), Caplan's nodules, vasculitic disorders, nail fold infarcts, neuropathy, nephropathy, amyloidosis, muscular pseudohypertrophy, endoscarditis, left ventricular failure, valulitis, scleromalacia, mononeuritis multiplex, atlanto-axial subluxation, and the like.

In another embodiment of the method, the individual having RA is administered placental stem cells or umbilical cord stem cells and additionally at least one other therapeutic agent. In specific embodiments, the therapeutic agent is, e.g., an analgesic, or an anti-inflammatory agent. In another specific embodiment, the therapeutic agent is a disease-modifying antirheumatic drug (DMARD). In a more specific embodiment, the DMARD is one or more of a xenobiotic (e.g., azathioprine, cyclosporine A, D-penicillamine, gold salts, hydroxychloroquine, leflunomide, methotrexate, minocycline or sulfasalazine) or a biological agent (e.g., tumor necrosis factor alpha (TNF-α) blockers, such as etanercept (ENBREL®), infliximab (REMICADE®), adalimumab (HUMIRA®), or one of the compounds disclosed in Section 5.6.8, above; interleukin-1 blockers; anti-B cell (CD20) antibody (e.g., rituximab or RITUXAN®); or blockers of T cell activation (e.g., abatacept or ORENCIA®). In another more specific embodiment, the analgesic or anti-inflammatory agent is a glucocorticoid, a non-steroidal anti-inflammatory drug, acetaminophen, ibuprofen, aspirin, an opiate, or lidocaine (topical). Any combination of the above therapeutic agents, suitable for treatment of GVHD or a symptom of GVHD, can be administered. Such therapeutic agents can be administered in any combination with the placental stem cells or umbilical cord stem cells, at the same time or as a separate course of treatment.

In a specific embodiment, a plurality of the placental stem cells or umbilical cord stem cells administered to an individual having RA have been genetically engineered to express a polypeptide therapeutic for RA. In a more specific embodiment, the polypeptide therapeutic for RA is IL-1Ra (interleukin-1 receptor antagonist). In another more specific embodiment, the polypeptide therapeutic for RA is a fusion protein comprising IL-1Ra and DHFR (dihydrofolate reductase). In a more specific embodiment, the placental stem cell or umbilical cord stem cell is transformed with a nucleic acid encoding IL-1Ra-DHFR fusion protein, wherein expression of the fusion protein is enhanced by an antifolate, e.g., methotrexate. In another specific embodiment, a plurality of a second type of stem cell is administered to the individual having RA, wherein a plurality of the second type of stem cell has been genetically engineered to express a polypeptide therapeutic for RA, e.g., any of the polypeptides disclosed above. In an even more specific embodiment, the nucleic acid encodes IL-1Ra-DHFR-IRES-Luc, where IRES is an internal ribosomal entry site, and Luc is luciferase. In another specific embodiment, said nucleic acid comprises a nucleotide sequence that enables control of expression of the IL-1Ra or IL-1Ra-DHFR fusion polypeptide.

Genetically engineered placental stem cells, umbilical cord stem cells, or other kind of stem cell, used to treat RA, can be administered to an individual with RA in any combination with such stem cells that have not been genetically modified.

5.6.11 Treatment of Scleroderma

In another embodiment, provided herein is a method of treating an individual that has, or is experiencing a symptom of, or is at risk for developing, scleroderma, comprising administering to the individual a therapeutically effective amount of placental stem cells or umbilical cord stem cells, or culture medium conditioned by placental stem cells or umbilical cord stem cells, wherein the therapeutically effective amount is an amount sufficient to cause a detectable improvement in one or more symptoms of scleroderma, or sufficient to detectably reduce the onset of one or more symptoms of scleroderma.

Scleroderma is a chronic disease characterized by excessive deposits of collagen in the skin or other organs. Scleroderma can be localized or generalized. The localized form of the disease, while disabling, tends not to be fatal. The generalized form of the disease, manifesting as diffuse scleroderma or systemic sclerosis, can be fatal as a result of heart, kidney, lung or intestinal damage. The three types of scleroderma are diffuse scleroderma and limited (CREST syndrome) scleroderma, which are systemic, and morphea/linear scleroderma, which is limited to the skin. Diffuse scleroderma is the most severe form, with victims experiencing rapid onset, widespread skin hardening, and significant internal organ damage, particularly to the lungs and gastrointestinal tract.

The limited form of scleroderma is much milder, exhibiting a slower onset and progression. Skin hardening is usually confined to the hands and face, internal organ involvement is less severe than in the diffuse form. Typically, Raynaud's phenomenon may precede scleroderma by several years. Raynaud's phenomenon is due to vasoconstriction of the small arteries of exposed peripheries—particularly the hands and feet—in the cold, and is classically characterized by a triphasic color change—first white, then blue and finally red on rewarming. The limited form is often referred to as CREST syndrome, where "CREST" is an acronym for the five main features, calcinosis (calcium deposits in soft tissue, e.g., the skin), Raynaud's syndrome, esophageal dysmotility, sclerodactyly (scleroderma of the fingers), and telangiectasia (spider veins).

Development of scleroderma has been correlated with the presence of autoantibodies, particularly anti-centromere and anti-scl70/anti-topoisomerase antibodies. Up to 90% of affected individuals have a detectable anti-nuclear antibody. Anti-centromere antibody is more common in the limited form (80-90%) than in the systemic form (10%), and anti-scl70 is more common in the diffuse form (30-40%) and in African-American patients.

Thus, in the method of treatment provided herein, the administration of placental stem cells or umbilical cord stem cells inhibits the development of, reduces the severity of, or reduces the progression of, one or more symptoms of scleroderma. In one embodiment, the scleroderma is limited scleroderma. In another embodiment, the scleroderma is diffuse scleroderma. In another embodiment, the scleroderma is morphea. In another specific embodiment, the symptom is one or more of hardening of the skin of the face, hardening of the skin of the fingers, Reynaud's syndrome, inappropriate vasoconstriction in an extremity, calcinosis, telangiectasia, or esophageal dysmotility. In another specific embodiment, administration of placental stem cells or umbilical cord stem cells detectably reduces the amount or concentration in a milliliter of blood from the individual of one or more anti-nuclear antibodies, e.g., an anti-centromere antibody or an anti-topoisomerase antibody.

In another embodiment, the method of treatment provided herein comprises the administration of a second therapy or therapeutic agent, wherein the second therapy or therapeutic agent is an anti-inflammatory drug, e.g., a steroidal anti-inflammatory drug, or a non-steroidal anti-inflammatory drug (NSAID), acetaminophen, naproxen, ibuprofen, acetylsalicylic acid, and the like. In a more specific embodiment in which an NSAID is administered, a proton pump inhibitor (PPI), e.g., omeprazole is also administered. In another embodiment, the second therapy is an immunosuppressant compound such as mycophenolate mofetil, cyclophosphamide or methotrexate. In another embodiment, where the affected individual has digital ulcerations and pulmonary hypertension, a vasodilator such as prostacyclin (iloprost) is administered.

In another embodiment, the second therapy is a second type of cell, e.g., hematopoietic stem cells, e.g., CD34$^+$ hematopoietic stem cells, in one or more doses of from about $10^5$ cells/kg to about $10^9$ cells/kg. In a specific embodiment, said second type of stem cell is a mesenchymal stem cell, e.g., a bone marrow-derived mesenchymal stem cell. The second type of stem cell, e.g., hematopoietic stem cell or mesenchymal stem cell, can be administered with the placental stem cells in any ratio, e.g., about 100:1, 75:1, 50:1, 25:1, 20:1, 15:1, 10:1, 5:1, 1:1, 1:5, 1:10, 1:15, 1:20, 1:25, 1:50, 1:75 or 1:100. Such mesenchymal stem cells can be obtained commercially or from an original source, e.g., bone marrow, bone marrow aspirate, adipose tissue, and the like.

Any combination of the above therapeutic agents, suitable for treatment of scleroderma or a symptom of scleroderma, can be administered. Such therapeutic agents can be administered in any combination with the placental stem cells or umbilical cord stem cells, at the same time or as a separate course of treatment.

Placental stem cells or umbilical cord stem cells can be administered to the individual suffering scleroderma in the form of a pharmaceutical composition, e.g., a pharmaceutical composition suitable for, e.g., intravenous, intramuscular or intraperitoneal injection.

5.6.12 Treatment of Psoriasis

In another embodiment, provided herein is a method of treating an individual that has, or is experiencing a symptom of, or is at risk for developing, psoriasis, comprising administering to the individual a therapeutically effective amount of placental stem cells or umbilical cord stem cells, or culture medium conditioned by placental stem cells or umbilical cord stem cells, wherein the therapeutically effective amount is an amount sufficient to cause a detectable improvement in one or more symptoms of psoriasis, sufficient to detectably reduce the onset of one or more symptoms of psoriasis, or sufficient to reduce the progress of psoriasis.

Psoriasis is a disease affecting the skin and joints, which commonly causes red scaly patches, called psoriatic plaques, to appear on the skin. Psoriatic patches are areas of inflammation and excessive skin production. Skin rapidly accumulates at these sites and takes a silvery-white appearance. Plaques frequently occur on the skin of the elbows and knees, but can affect any area including the scalp and genitals. Psoriasis is hypothesized to be immune-mediated.

Several different types of psoriasis have been identified, as follows:

Plaque psoriasis (psoriasis vulgaris), the most common form of psoriasis, typically appears as raised areas of inflamed skin covered with silvery white scaly skin, called plaques.

Flexural psoriasis (inverse psoriasis) appears as smooth inflamed patches of skin occurring in skin folds, for example, around the genitals (between the thigh and groin), the armpits, under an overweight stomach, and under the breasts.

Guttate psoriasis manifests as numerous small oval (teardrop-shaped) spots that appear over large areas of the body, such as the trunk, limbs, and scalp. Guttate psoriasis is associated with streptococcal throat infection.

Pustular psoriasis appears as raised bumps that are filled with non-infectious pus (pustules). Pustular psoriasis can be localized, commonly to the hands and feet (palmoplantar pustulosis), or generalized with widespread patches occurring randomly on any part of the body.

Nail psoriasis produces a variety of changes in the appearance of finger and toe nails, including discoloration under the nail plate, pitting of the nails, lines going across the nails, thickening of the skin under the nail, and the loosening (onycholysis) and crumbling of the nail.

Psoriatic arthritis involves joint and connective tissue inflammation, e.g., in the joints of the fingers and toes, which can result in a sausage-shaped swelling of the fingers and toes known as dactylitis. Psoriatic arthritis can also affect the hips, knees and spine (spondylitis).

Erythrodermic psoriasis manifests as the widespread inflammation and exfoliation of the skin over most of the body surface. It may be accompanied by severe itching, swelling and pain. It is often the result of an exacerbation of unstable plaque psoriasis, particularly following the abrupt withdrawal of systemic treatment. This form of psoriasis can be fatal, as the extreme inflammation and exfoliation disrupt the body's ability to regulate temperature and for the skin to perform barrier functions.

In one embodiment, the invention provides for the administration of an effective dose placental stem cells to an individual affected with psoriasis, wherein said effective dose is an amount of placental stem cells sufficient, e.g., to cause a detectable improvement in, reduce the severity of, or reduce the progression of, one or more of the symptoms of psoriasis listed above.

The severity of psoriasis can be evaluated, e.g., by the Psoriasis Area Severity Index (PAST). PASI combines the assessment of the severity of lesions and the area affected into a single score in the range 0 (no disease) to 72 (maximal disease).

To calculate the PASI, the body is divided into four sections: legs, the body (trunk area (stomach, chest, back, etc.); arms; and head. Each of these areas is scored by itself, and then the four scores are combined into the final PASI. For each section, the percent of area of skin afflicted with psoriasis is estimated and then transformed into a grade from 0 to 6, as follows:

| Percent Area Involved | Grade |
| --- | --- |
| 0 | 0 |
| <10 | 1 |
| 10-29% | 2 |
| 30-49 | 3 |
| 50-69 | 4 |
| 70-89 | 5 |
| 90-100 | 6 |

The severity is estimated by four different parameters, graded from 0 to 4: itching, erythema (redness), scaling and thickness. The sum of all four severity parameters is then calculated for each section of skin, multiplied by the area score for that area and multiplied by weight of respective section (0.1 for head, 0.2 for arms, 0.3 for body and 0.4 for legs). Example: $(I_{body}+E_{body}+S_{body}+T_{body}) \times A_{body} \times 0.3 = \text{Total}_{body}$. At the end the total PASI is calculated as a sum of PASIs for all four skin sections.

The degree of severity can also be assessed by photographing an individual afflicted with psoriasis, and calculating, by computer, the percent body area covered by psoriatic lesions.

Thus, in a specific embodiment of the method of treatment provided herein, the psoriasis is plaque psoriasis (psoriasis vulgaris), flexural psoriasis (inverse psoriasis), guttate psoriasis, pustular psoriasis, nail psoriasis, psoriatic arthritis, or erythrodermic psoriasis. In a specific embodiment of the method, the therapeutically effective amount of placental stem cells or umbilical cord stem cells, or culture medium conditioned by placental stem cells or umbilical cord stem cells is an amount sufficient to cause an improvement in, a delay in onset of, or a lessening of the progression of one or more symptoms of psoriasis, where said one or more symptoms are scaling of the skin, redness of the skin, thickening of the skin, formation of plaques, discoloration under the nail plate, pitting of the nails, lines going across the nails, thickening of the skin under the nail, onycholysis, development of pustules, joint or connective tissue inflammation, inflammation of the skin, or exfoliation of the skin. In another embodiment, the therapeutically effective amount of placental stem cells or umbilical cord stem cells, or culture medium conditioned by placental stem cells or umbilical cord stem cells is an amount sufficient to cause a 5, 10, 15, 20, 25, 30, 35, 40 or more point reduction in the Psoriasis Area Severity Index.

In another embodiment, the therapeutically effective amount of placental stem cells or umbilical cord stem cells, or culture medium conditioned by placental stem cells or umbilical cord stem cells, is administered in conjunction with a second therapy. The second therapy can be topical, e.g., creams or ointments comprising one or more of a corticosteroid (e.g., desoximetasone), a vitamin $D_3$ analog (e.g., calcipotriol), anthralin, argan oil, a retinoid, or coal tar. In another specific embodiment, the second therapy comprises one or more exposures, e.g., for about 1, 2, 3, 4, 5, 6, 7, 8, 9, 10, 12, 14, 16, 18 or 20 minutes, to ultraviolet light, e.g., UVB of a wavelength between about 280 nm to about 315 nm, particularly about 311 nm to about 312 nm. In another specific embodiment, the second therapy comprises topical administration of psoralen in combination with exposure to UVA light. In another specific embodiment, the second therapy comprises one or more systemic administrations of one or more of, e.g., methotrexate, cyclosporine, a retinoid, tioguanine, hydroxyurea, sulfasalazine, mycophenolate mofetil, azathioprine, oral tacrolimus and/or a fumaric acid ester.

5.6.13 Treatment of Lupus Erythematosus

In another embodiment, provided herein is a method of treating an individual that has, or is experiencing a symptom of, or is at risk for developing, lupus erythematosus (LE), comprising administering to the individual a therapeutically effective amount of placental stem cells or umbilical cord stem cells, or culture medium conditioned by placental stem cells or umbilical cord stem cells, wherein the therapeutically effective amount is an amount sufficient to cause a detectable improvement in one or more symptoms of LE, sufficient to detectably reduce the onset of one or more symptoms of LE, or sufficient to reduce the progress of LE.

Symptoms of LE are numerous, and the disease may progress differently in different individuals. Symptoms can include dermatological manifestations (e.g., malar rash (also called butterfly rash), discoid lupus (thick, red scaly patches on the skin), alopecia, mouth, nasal, and vaginal ulcers, and/or lesions on the skin); musculoskeletal manifestations (e.g., joint pain); hematological manifestations (e.g., anemia and iron deficiency, lower than normal platelet and white blood cell counts, antiphospholipid antibody syndrome (a thrombotic disorder in which autoantibodies to phospholipids are present in the patient's serum), and/or presence of anticardiolipin antibody in the blood); cardiac manifestations (e.g., pericarditis, myocarditis, and/or endocarditis); pulmonary manifestations (e.g., lung and/or pleura inflammation, pleuritis, pleural effusion, lupus pneumonitis, chronic diffuse interstitial lung disease, pulmonary hypertension, pulmonary emboli, and/or pulmonary hemorrhage); hepatic manifestations (e.g., autoimmune hepatitis; jaundice; presence of antinuclear antibody (ANA), smooth muscle antibody (SMA), liver/kidney microsomal antibody (LKM-1) and/or anti-mitochondrial antibody (AMA) in the bloodstream); renal manifestations (e.g., painless hematuria or proteinuria, lupus nephritis, renal failure, and/or development of membranous glomerulonephritis with "wire loop" abnormalities); neurological manifestations (e.g., seizures, psychosis, abnormalities in the cerebrospinal fluid); T-cell abnormalities (e.g., deficiency in CD45 phosphatase and/or increased expression of CD40 ligand); and/or nonspecific manifestations (e.g., lupus gastroenteritis, lupus pancreatitis, lupus cystitis, autoimmune inner ear disease, parasympathetic dysfunction, retinal vasculitis, systemic vasculitis, increased expression of FcεRIγ, increased and sustained calcium levels in T cells, increase of inositol triphosphate in the blood, reduction in protein kinase C phosphorylation, reduction in Ras-MAP kinase signaling, and/or a deficiency in protein kinase A I activity.

Thus, in a specific embodiment, said therapeutically effective amount of placental stem cells or umbilical cord stem cells, or culture medium conditioned by placental stem cells or umbilical cord stem cells is an amount effective to cause a detectable improvement in one or more symptoms of LE, sufficient to detectably reduce the onset of one or more symptoms of LE, or sufficient to reduce the worsening of one or more symptoms of LE, wherein said one or more symptoms comprises one or more dermatological, hematological, musculoskeletal, neurological, renal, hepatic, or T-cell manifestations of LE. In another specific embodiment, said therapeutically effective amount is an amount sufficient to cause a detectable improvement in one or more symptoms of LE, sufficient to detectably reduce the onset of one or more symptoms of LE, or sufficient to reduce the worsening of one or more symptoms of LE, wherein said one or more symptoms comprise malar rash, butterfly rash, discoid lupus, alopecia, mouth, nasal, and vaginal ulcers, lesions on the skin, joint pain anemia and/or iron deficiency, lower than normal platelet and white blood cell counts, antiphospholipid antibody syndrome, presence of anticardiolipin antibody in the blood, pericarditis, myocarditis, endocarditis, lung and/or pleural inflammation, pleuritis, pleural effusion, lupus pneumonitis, chronic diffuse interstitial lung disease, pulmonary hypertension, pulmonary emboli, pulmonary hemorrhage, autoimmune hepatitis; jaundice; presence of antinuclear antibody (ANA), smooth muscle antibody (SMA), liver/kidney microsomal antibody (LKM-1) and/or anti-mitochondrial antibody (AMA) in the bloodstream, painless hematuria or proteinuria, lupus nephritis, renal failure, and/or development of membranous glomerulonephritis with "wire loop" abnormalities); neurological manifestations (e.g., seizures, psychosis, abnormalities in the cerebrospinal fluid); T-cell abnormalities (e.g., deficiency in CD45 phosphatase and/or increased expression of CD40 ligand); and/or nonspecific manifestations (e.g., lupus gastroenteritis, lupus pancreatitis, lupus cystitis, autoimmune inner ear disease, parasympathetic dysfunction, retinal vasculitis, systemic vasculitis, increased expression of FcεRIγ, increased and sustained calcium levels in T cells, increase of inositol triphosphate in the blood, reduction in protein kinase C phosphorylation, reduction in Ras-MAP kinase signaling, and/or a deficiency in protein kinase A I activity.

Placental stem cells or umbilical cord stem cells can be administered to the individual suffering scleroderma in the form of a pharmaceutical composition, e.g., a pharmaceutical composition suitable for, e.g., intravenous, intramuscular or intraperitoneal injection.

5.6.14 Treatment of Mycosis Fungoides

In another embodiment, provided herein is a method of treating an individual that has, or is experiencing a symptom of, or is at risk for developing, mycosis fungoides, comprising administering to the individual a therapeutically effective amount of placental stem cells or umbilical cord stem cells, or culture medium conditioned by placental stem cells or umbilical cord stem cells, wherein the therapeutically effective amount is an amount sufficient to cause a detectable improvement in one or more symptoms of mycosis fungoides, sufficient to detectably reduce the onset of one or more symptoms of mycosis fungoides, or sufficient to reduce the progress of mycosis fungoides.

Mycosis fungoides is the most common of the cutaneous T-cell lymphomas, a group of rare cancers that grow in the skin. Sezary syndrome, a more rare form in which the T cells affect the peripheral blood as well as the skin, occurs in about 5% of all cases of mycosis fungoides. Mycosis fungoides generally progresses in stages defined by the skin symptoms: (1) patch phase, in which the skin has flat, red patches, or, in dark-skinned individuals very light or very dark patches, that are very itchy, and may be raised and hard (plaques); (2) skin tumors phase, in which red-violet raised lumps (nodules) appear, which may be dome-shaped (like a mushroom) or ulcerated; (3) skin redness (erythroderma) stage, in which the individual's skin develops large red areas that are very itchy and scaly, and in which skin of the palms and soles may thicken and crack; and (4) lymph node stage, in which mycosis fungoides begins to move to other parts of the body via the lymph nodes, which become inflamed, and often cancerous, and may spread to the liver, lungs, or bone marrow.

Thus in a specific embodiment, the therapeutically effective amount of placental stem cells or umbilical cord stem cells, or culture medium conditioned by placental stem cells or umbilical cord stem cells is an amount effective to cause a detectable improvement in one or more symptoms of mycosis fungoides, sufficient to detectably reduce the onset of one or more symptoms of mycosis fungoides, or sufficient to reduce the worsening of one or more symptoms of LE, wherein said one or more symptoms comprises one or more dermatological, hematological, musculoskeletal, neurological, renal, hepatic, or T-cell manifestations of mycosis fungoides. In another specific embodiment, said therapeutically effective amount is an amount sufficient to cause a detectable improvement in one or more symptoms of mycosis fungoides, sufficient to detectably reduce the onset of one or more symptoms of mycosis fungoides, or sufficient to reduce the worsening of one or more symptoms of mycosis fungoides, wherein said one or more symptoms comprise itchy light or dark patches on the skin, skin plaques, development of skin tumors, raised bumps on the skin, development of skin areas that are red, scaly and itchy, thickening of the skin of the soles or palms, cracking of the skin of the soles or palms, or inflammation of the lymph nodes.

In another embodiment, the therapeutically effective amount of placental stem cells or umbilical cord stem cells, or culture medium conditioned by placental stem cells or umbilical cord stem cells, is administered in conjunction with a second therapy or second therapeutic agent. In more specific embodiments, the second therapy or therapeutic agent is one or more of exposure of an affected area of said individual to sunlight or ultraviolet light, topical steroids, local superficial radiotherapy, total skin electron beam radiation, application of organic (Manuka) honey to skin affected by erythroderma, or biological therapies. In a more specific embodiment, said biological therapies comprise administration to the individual of one or more of an interferon, a retinoid, a rexinoid, vorinostat (e.g., ZOLINZA®).

5.6.15 Treatment of Diabetes

In another embodiment, provided herein is a method of treating an individual that has, or is experiencing a symptom of, or is at risk for developing, diabetes, comprising administering to the individual a therapeutically effective amount of adherent placental stem cells or adherent umbilical cord stem cells, or culture medium conditioned by placental stem cells or umbilical cord stem cells, wherein the therapeutically effective amount is an amount sufficient to cause a detectable improvement in one or more symptoms of diabetes, sufficient to detectably reduce the onset of one or more symptoms of diabetes, or sufficient to reduce the progress of diabetes. In a specific embodiment, the diabetes is diabetes mellitus Type 1, also known as Type 1 diabetes, Type I diabetes, T1D, or insulin-dependent diabetes mellitus (IDDM).

The placental stem cells can be administered one or more times during the course of the disease. Preferably, the stem cells are administered within 1, 2, 3, 4, 5, or 6 days, or 1 week, of first diagnosis. In one embodiment, said therapeutically effective amount of the stem cells is an amount sufficient to reverse, reduce the severity of, or otherwise ameliorate a symptom of diabetes mellitus Type 1, including abnormally high blood sugar, lack of insulin resistance as determined by a glucose tolerance test, fatigue, or loss of consciousness.

The placental stem cells can be administered in conjunction with a second therapy, e.g., transplanted pancreatic tissue and/or islet cells; autologous or allogeneic stem cell therapy, and the like.

5.6.16 Second Therapeutic Compositions and Second Therapies

In any of the above methods of treatment, the method can comprise the administration of a second therapeutic composition or second therapy. The recitation of specific second therapeutic compounds or second therapies in the methods of treating specific diseases, above, are not intended to be exclusive. For example, any of the diseases, disorders or conditions discussed herein can be treated with any of the anti-inflammatory compounds or immunosuppressive compounds described herein. In embodiments in which placental stem cells are administered with a second therapeutic agent, or with a second type of stem cell, the placental stem cells and second therapeutic agent and/or second type of stem cell can be administered at the same time or different times, e.g., the administrations can take place within 1, 2, 3, 4, 5, 6, 7, 8, 9 10, 20, 30, 40, or 50 minutes of each other, or 1, 2, 3, 4, 5, 6, 7, 8, 9, 10, 12, 14, 16, 18, 20, or 22 hours of each other, or within 1, 2, 3, 4, 5, 6, 7 8, 9 or 10 days of each other.

In a specific embodiment, treatment of a disease, disorder or condition related to or caused by an inappropriate, deleterious or harmful immune response comprises administration of a second type of stem cell, or population of a second type of stem cell. In a specific embodiment, said second type of stem cell is a mesenchymal stem cell, e.g., a bone marrow-derived mesenchymal stem cell. In other embodiments, the second type of stem cell is a multipotent stem cell, a pluripotent stem cell, a progenitor cell, a hematopoietic stem cell, e.g., a CD34$^+$ hematopoietic stem cell, an adult stem cell, an embryonic stem cell or an embryonic germ cell. The second type of stem cell, e.g., mesenchymal stem cell, can be administered with the placental stem cells or umbilical cord stem cells in any ratio, e.g., a ratio of about 100:1, 75:1, 50:1, 25:1, 20:1, 15:1, 10:1, 5:1, 1:1, 1:5, 1:10, 1:15, 1:20, 1:25, 1:50, 1:75 or 1:100. Mesenchymal stem cells can be obtained commercially or from an original source, e.g., bone marrow, bone marrow aspirate, adipose tissue, and the like.

In another specific embodiment, said second therapy comprises an immunomodulatory compound, wherein the immunomodulatory compound is 3-(4-amino-1-oxo-1,3-dihydroisoindol-2-yl)-piperidine-2,6-dione; 3-(4'aminoisoindolin-1'-one)-1-piperidine-2,6-dione; 4-(Amino)-2-(2,6-dioxo(3-piperidyl))-isoindoline-1,3-dione; or α-(3-aminophthalimido) glutarimide. In a more specific embodiment, said immunomodulatory compound is a compound having the structure

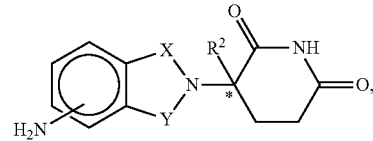

wherein one of X and Y is C=O, the other of X and Y is C=O or CH$_2$, and R$^2$ is hydrogen or lower alkyl, or a pharmaceutically acceptable salt, hydrate, solvate, clathrate, enantiomer, diastereomer, racemate, or mixture of stereoisomers thereof. In another more specific embodiment, said immunomodulatory compound is a compound having the structure

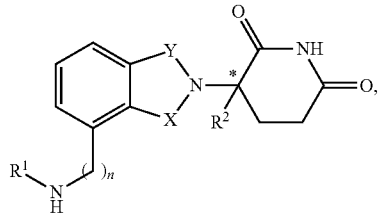

wherein one of X and Y is C=O and the other is CH$_2$ or C=O;

R$^1$ is H, (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$—O$_5$)heteroaryl, C(O)R$^3$, C(S)R$^3$, C(O)OR$^4$, (C$_1$-C$_8$)alkyl-N(R$^6$)$_2$, (C$_1$-C$_8$)alkyl-OR$^5$, (C$_1$-C$_8$)alkyl-C(O)OR$^5$, C(O)NHR$^3$, C(S)NHR$^3$, C(O)NR$^3$R$^3$, C(S)NR$^3$R$^3$ or (C$_1$-C$_8$)alkyl-O(CO)R$^5$;

R$^2$ is H, F, benzyl, (C$_1$-C$_8$)alkyl, (C$_2$-C$_8$)alkenyl, or (C$_2$-C$_8$)alkynyl;

R$^3$ and R$^{3'}$ are independently (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)

heteroaryl, $(C_0\text{-}C_8)$alkyl-$N(R^6)_2$, $(C_1\text{-}C_8)$alkyl-$OR^5$, $(C_1\text{-}C_8)$alkyl-$C(O)OR^5$, $(C_1\text{-}C_8)$alkyl-$O(CO)R^5$, or $C(O)OR^5$;

$R^4$ is $(C_1\text{-}C_8)$alkyl, $(C_2\text{-}C_8)$alkenyl, $(C_2\text{-}C_8)$alkynyl, $(C_1\text{-}C_4)$alkyl-$OR^5$, benzyl, aryl, $(C_0\text{-}C_4)$alkyl-$(C_1\text{-}C_6)$heterocycloalkyl, or $(C_0\text{-}C_4)$alkyl-$(C_2\text{-}C_5)$heteroaryl;

$R^5$ is $(C_1\text{-}C_8)$alkyl, $(C_2\text{-}C_8)$alkenyl, $(C_2\text{-}C_8)$alkynyl, benzyl, aryl, or $(C_2\text{-}O_5)$heteroaryl;

each occurrence of $R^6$ is independently H, $(C_1\text{-}C_8)$alkyl, $(C_2\text{-}C_8)$alkenyl, $(C_2\text{-}C_8)$alkynyl, benzyl, aryl, $(C_2\text{-}O_5)$heteroaryl, or $(C_0\text{-}C_8)$alkyl-$C(O)O$—$R^5$ or the $R^6$ groups can join to form a heterocycloalkyl group;

n is 0 or 1; and

\* represents a chiral-carbon center;

or a pharmaceutically acceptable salt, hydrate, solvate, clathrate, enantiomer, diastereomer, racemate, or mixture of stereoisomers thereof. In another more specific embodiment, said immunomodulatory compound is a compound having the structure

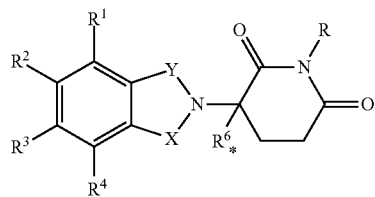

wherein:

one of X and Y is C=O and the other is $CH_2$ or C=O;

R is H or $CH_2OCOR'$;

(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or —$NHR^5$ and the remaining of $R^1$, $R^2$, $R^3$, or $R^4$ are hydrogen;

$R^5$ is hydrogen or alkyl of 1 to 8 carbons $R^6$ hydrogen, alkyl of 1 to 8 carbon atoms, benzo, chloro, or fluoro;

R' is $R^7$—$CHR^{10}$—$N(R^8R^9)$;

$R^7$ is m-phenylene or p-phenylene or —$(C_n$—$H_{2n})$— in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X_1CH_2CH_2$— in which $X_1$ is —O—, —S—, or —NH—;

$R^{10}$ (is hydrogen, alkyl of to 8 carbon atoms, or phenyl; and

\* represents a chiral-carbon center;

or a pharmaceutically acceptable salt, hydrate, solvate, clathrate, enantiomer, diastereomer, racemate, or mixture of stereoisomers thereof.

Any combination of the above therapeutic agents, suitable for treatment of inflammatory bowel disease or a symptom of inflammatory bowel disease, can be administered. Such therapeutic agents can be administered in any combination with the placental stem cells or umbilical cord stem cells, at the same time or as a separate course of treatment.

Placental stem cells or umbilical cord stem cells can be administered to the individual suffering IBD, e.g., Crohn's disease, in the form of a pharmaceutical composition, e.g., a pharmaceutical composition suitable for intravenous, intramuscular or intraperitoneal injection. Placental stem cells can be administered in a single dose, or in multiple doses. Where placental stem cells are administered in multiple doses, the doses can be part of a therapeutic regimen designed to relieve one or more acute symptoms of IBD, e.g., Crohn's disease, of can be part of a long-term therapeutic regimen designed to prevent, or lessen the severity, of a chronic course of the disease. In embodiments in which placental stem cells are administered with a second therapeutic agent, or with a second type of stem cell, the placental stem cells and second therapeutic agent and/or second type of stem cell can be administered at the same time or different times, e.g., the administrations can take place within 1, 2, 3, 4, 5, 6, 7, 8, 9 10, 20, 30, 40, or 50 minutes of each other, or 1, 2, 3, 4, 5, 6, 7, 8, 9, 10, 12, 14, 16, 18, 20, or 22 hours of each other, or within 1, 2, 3, 4, 5, 6, 7 8, 9 or 10 days of each other.

6. EXAMPLES

6.1 Example 1: Isolation of Adherent Placental Stem Cells

This example demonstrated the collection and isolation of adherent placental stem cells.

Materials and Methods. Placenta donors were recruited from expectant mothers that enrolled in private umbilical cord blood banking programs and provided informed consent permitting the use of the exsanguinated placenta following recovery of cord blood for research purposes. These donors permitted use of blinded data generated from the normal processing of their umbilical cord blood specimens for cryopreservation. This allowed comparison between the composition of the collected cord blood and the effluent perfusate recovered using this experimental method described below.

Following exsanguination of the umbilical cord and placenta, the placenta was placed in a sterile, insulated container at room temperature and delivered to the laboratory within 4 hours of birth. Placentas were discarded if, on inspection, they had evidence of physical damage such as fragmentation of the organ or avulsion of umbilical vessels. Placentas were maintained at room temperature (23+/−2° C.) or refrigerated (4° C.) in sterile containers for 2 to 20 hours. Periodically, the placentas were immersed and washed in sterile saline at 25+/−3° C. to remove any visible surface blood or debris. The umbilical cod was transected approximately 5 cm from its insertion into the placenta and the umbilical vessels were cannulated with Teflon or polypropylene catheters connected to a sterile fluid path allowing bidirectional perfusion of the placenta and recovery of the effluent fluid. The system employed herein enabled all aspects of conditioning, perfusion and effluent collection to be performed under controlled ambient atmospheric conditions as well as real-time monitoring of intravascular pressure and flow rates, core and perfusate temperatures and recovered effluent volumes. A range of conditioning protocols was evaluated over a 24 hour postpartum period and the cellular composition of the effluent fluid was analyzed by flow cytometry, light microscopy and colony forming unit assays.

Placental Conditioning. A placenta was maintained under varying conditions in an attempt to simulate and sustain a physiologically compatible environment for the proliferation and recruitment of placental stem cells. A cannula was flushed with IMDM serum-free medium (GibcoBRL, NY) containing 2 U/ml heparin (EJkins-Sinn, N.J.). Perfusion of the placenta was performed at a rate of 50 mL per minute until approximately 150 mL of perfusate was collected. This volume of perfusate was labeled the "early fraction". The placenta was perfused at the same rate to collect a second fraction of approximately 150 mL, which was labeled the "late fraction". During the course of the procedure, the placenta was gently massaged to aid in the perfusion process and assist in the recovery of cellular material. Effluent fluid was collected from the perfusion circuit by both gravity drainage and aspiration through the arterial cannula.

Placentas were obtained from delivery rooms along with cord blood after obtaining written parental consent, and were processed at room temperature within 12 to 24 hours after delivery. Before processing, the membranes were removed and the maternal site washed clean of residual blood. The umbilical vessels were cannulated with catheters made from 20 gauge Butterfly needles use for blood sample collection. Placentas were then perfused with heparinized (2 U/mL) Dulbecco's modified Eagle Medium (HDMEM) at the rate of 15 mL/minute for 10 minutes and the perfusates were collected from the maternal sites within one hour and the nucleated cells counted. The perfusion and collection procedures were repeated once or twice until the number of recovered nucleated cells fell below 100/µL. The perfusates were pooled and subjected to light centrifugation to remove platelets, debris and de-nucleated cell membranes. The nucleated cells were then isolated by Ficoll-Hypaque density gradient centrifugation and after washing, resuspended in HDMEM. For isolation of adherent cells, aliquots of 5-10× $10^6$ cells were placed in each of several T-75 flasks and cultured with commercially available Mesenchymal Stem Cell Growth Medium (MSCGM) obtained from BioWhittaker, and placed in a tissue culture incubator at 37° C., 5% $CO_2$. After 10 to 15 days, the non-adherent cells were removed by washing with PBS, which was then replaced by MSCGM. The flasks were examined daily for the presence of various adherent cell types and in particular, for identification and expansion of clusters of fibroblastoid cells.

Cell Recovery and Isolation. Cells were recovered from the perfusates by centrifugation at about 200×g for 15 minutes at room temperature. This procedure served to separate cells from contaminating debris and platelets. The cell pellets were resuspended in IMDM serum-free medium containing 2 U/ml heparin and 2 mM EDTA (GibcoBRL, NY). The total mononuclear cell fraction was isolated using Lymphoprep (Nycomed Pharma, Oslo, Norway) according to the manufacturer's recommended procedure and the mononuclear cell fraction was resuspended. Cells were counted using a hemocytometer. Viability was evaluated by trypan blue exclusion. Isolation of mesenchymal cells was achieved by differential trypsinization using a solution of 0.05% trypsin with 0.2% EDTA (Sigma). Differential trypsinization was possible because fibroblastoid cells detached from plastic surfaces within about five minutes whereas the other adherent populations required more than 20-30 minutes incubation. The detached fibroblastoid cells were harvested following trypsinization and trypsin neutralization using Trypsin Neutralyzing Solution (TNS, BioWhitaker). The cells were washed in HDMEM and resuspended in MSCGM. Flow cytometry of the cells was carried out using a Becton-Dickinson FACSCalibur instrument using FITC and PE labeled monoclonal antibodies selected on the basis of known markers for bone marrow-derived MSC (mesenchymal stem cells). Antibodies were purchased from B.D. and Caltag laboratories (South San Francisco, Calif.), and SH2, SH3 and SH4 antibody producing hybridomas were obtained from AM. Cul. and reactivities of the antibodies in their cultured supernatants were detected by FITC or PE labeled F(ab)$'_2$ goat anti-mouse antibodies. Lineage differentiation was carried out using the commercially available induction and maintenance culture media (BioWhittaker), used as per manufacturer's instructions.

Isolation of Placental Stem Cells. Microscopic examination of the adherent cells in the culture flasks revealed morphologically different cell types, including spindle-shaped cells, round cells with large nuclei and numerous perinuclear small vacuoles, and star-shaped cells with several projections, through one of which the cells were attached to the flask. No attempts were made to further characterize these types of adherent cells, because similar non-stem cells were observed in the culture of bone marrow, cord and peripheral blood. However, fibroblastoid cells, appearing last as clusters and appearing by visual inspection to be similar to bone marrow-derived mesenchymal stem cells, were isolated by differential trypsinization and subcultured in secondary flasks. Phase microscopy of the cells, which appeared rounded after trypsinization, showed them to be highly granulated, and similar to bone marrow-derived MSC produced in the laboratory or purchased from BioWhittaker.

When subcultured, these adherent placental cells, in contrast to their earlier phase, adhered within hours, assumed characteristic fibroblastoid shape, and formed a growth pattern similar to the reference bone marrow-derived MSC. Moreover, during subculturing and refeeding, the loosely bound mononuclear cells were washed out and the cultures remained homogeneous and devoid of any visible non-fibroblastoid cell contaminants.

In subsequent experiments, the cell surface marker phenotype, or, in the case of OCT-4, the gene expression phenotype, of these adherent cells, obtained from different perfusion experiments, was characterized. The results of these experiments are shown in Table 3, below:

TABLE 3

Characterization of placental stem cells (PLSC) collected from separate perfusion experiments.

| ID # | Medium | Frozen (Vials) | CD34 | CD45 | CD10 | CD29 | CD54 | SH2 | SH3 | SH4 | SSEA4 | CD44 | HLA1 | CD90 | Oct4 |
|---|---|---|---|---|---|---|---|---|---|---|---|---|---|---|---|
| PLSC-1 | BW | Y (2) | − | − | + | + | + | + | + | + | | | | | |
| PLSC-2 | BW | Y (6) | − | − | + | + | + | + | + | + | | | | | |
| PLSC-3 | BW | Y (2) | − | − | + | + | + | + | + | + | | | | | + |
| PLSC-4 | BW | None | | | | | | | | | | | | | |
| PLSC-5 | BW | Y (9) | − | − | + | + | + | + | + | + | | | | | |
| PLSC-6 | BW | Y (26) | − | − | +/low | + | + | + | + | + | | | | | + |
| PLSC-7 | BW | Y (2) | − | − | + | + | + | + | + | + | | | | | + |
| PLSC-8 | BW | Y (10) | − | − | + | + | + | + | + | + | | | | | + |
| PLSC-9 | BW | Y (11) | − | − | + | + | + | + | + | + | | | | | + |
| PLSC-10 | BW | Y (10) | − | − | + | + | + | + | + | + | | | | | + |
| PLSC-11 | D-5% FCS | Y (9) | | | | | | | | | | | | | |

TABLE 3-continued

Characterization of placental stem cells (PLSC) collected from separate perfusion experiments.

| ID # | Medium | Frozen (Vials) | CD34 | CD45 | CD10 | CD29 | CD54 | SH2 | SH3 | SH4 | SSEA4 | CD44 | HLA1 | CD90 | Oct4 |
|---|---|---|---|---|---|---|---|---|---|---|---|---|---|---|---|
| PLSC-12 | D-5% FCS | Y (7) | | | | | | | | | | | | | |
| PLSC-13 | D-5% FCS | Y (5) | | | | | | | | | | | | | |
| PLSC-14 | D-5% FCS | Y (9) | | | | | | | | | | | | | |
| PLSC-15 | Anthro-1 | Y (7) | − | − | + | + | + | + | + | + | | + | + | + | |
| PLSC-16 | Anthro-1 | Y (8) | − | − | + | + | + | + | + | + | | + | + | + | |
| PLSC-17 | Anthro-1 | Y (8) | − | − | + | + | + | + | + | + | | + | + | + | |
| PLSC-18 | Anthro-1 | Y (8) | − | − | + | + | + | + | + | + | | + | + | + | |
| PLSC-19 | BWtoA | Y (17) | − | − | + | + | + | + | + | + | | + | + | + | |
| PLSC-20 | BWtoA | Y (40) | − | − | + | + | + | + | + | + | | + | + | + | |
| PLSC-21 | BWtoA | Y (9) | − | − | + | + | + | + | + | + | +/− | + | + | + | |
| PLSC-22 | BWtoA | FTE | | | | | | | | | | | | | |
| PLSC-23 | Anthro-1 | Y (10) | − | − | + | + | + | + | + | + | | + | + | + | |
| PLSC-24 | Anthro-1 | FTE | | | | | | | | | | | | | |
| PLSC-25 | Anthro-1 | FTE | | | | | | | | | | | | | |
| PLSC-26 | Anthro-1 | Y (15) | − | − | + | + | + | + | + | + | | + | + | + | |
| PLSC-27 | Anthro-1 | Y (25) | − | − | + | + | + | + | + | + | | + | + | + | |

+: Detected by flow cytometry, or, for OCT-4, gene expression detected by RT-PCR
−: Not detected
Blank: Presence of marker was not tested
FTE: Failed to expand
D-5% FCS: DMEM-5% FCS
BWtoA: BW to Anthro-1 medium

6.2 Example 2: Culture of Placental Stem Cells

Placental stem cells are obtained from a post-partum mammalian placenta either by perfusion or by physical disruption, e.g., enzymatic digestion. The cells are cultured in a culture medium comprising 60% DMEM-LG (Gibco), 40% MCDB-201 (Sigma), 2% fetal calf serum (FCS) (Hyclone Laboratories), 1× insulin-transferrin-selenium (ITS), 1× lenolenic-acid-bovine-serum-albumin (LA-BSA), $10^{-9}$M dexamethasone (Sigma), $10^{-4}$M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/1000 U streptomycin.

The culture flask in which the cells are cultured is prepared as follows. T75 flasks are coated with fibronectin (FN), by adding 5 ml PBS containing 5 ng/ml human FN (Sigma F0895) to the flask. The flasks with FN solution are left at 37° C. for 30 min. The FN solution is then removed prior to cell culture. There is no need to dry the flasks following treatment. Alternatively, the flasks are left in contact with the FN solution at 4° C. overnight or longer; prior to culture, the flasks are warmed and the FN solution is removed.

Placental Stem Cells Isolated by Perfusion

Cultures of placental stem cells from placental perfusate are established as follows. Cells from a Ficoll gradient are seeded in FN-coated T75 flasks, prepared as above, at 50-100×10$^6$ cells/flask in 15 ml culture medium. Typically, 5 to 10 flasks are seeded. The flasks are incubated at 37° C. for 12-18 hrs to allow the attachment of adherent cells. 10 ml of warm PBS is added to each flask to remove cells in suspension, and mixed gently. 15 mL of the medium is then removed and replaced with 15 ml fresh culture medium. All medium is changed 3-4 days after the start of culture. Subsequent culture medium changes are performed, during which 50% or 7.5 ml of the medium is removed.

Starting at about day 12, the culture is checked under a microscope to examine the growth of the adherent cell colonies. When cell cultures become approximately 80% confluent, typically between day 13 to day 18 after the start of culture, adherent cells are harvested by trypsin digestion. Cells harvested from these primary cultures are designated passage 0 (zero).

Placental Stem Cells Isolated by Physical Disruption and Enzymatic Digestion

Placental stem cell cultures are established from digested placental tissue as follows. The perfused placenta is placed on a sterile paper sheet with the maternal side up. Approximately 0.5 cm of the surface layer on maternal side of placenta is scraped off with a blade, and the blade is used to remove a placental tissue block measuring approximately 1×2×1 cm. This placenta tissue is then minced into approximately 1 mm$^3$ pieces. These pieces are collected into a 50 ml Falcon tube and digested with collagenase IA (2 mg/ml, Sigma) for 30 minutes, followed by trypsin-EDTA (0.25%, GIBCO BRL) for 10 minutes, at 37° C. in water bath. The resulting solution is centrifuged at 400 g for 10 minutes at room temperature, and the digestion solution is removed. The pellet is resuspended to approximately 10 volumes with PBS (for example, a 5 ml pellet is resuspended with 45 ml PBS), and the tubes are centrifuged at 400 g for 10 minutes at room temperature. The tissue/cell pellet is resuspended in 130 mL culture medium, and the cells are seeded at 13 ml per fibronectin-coated T-75 flask. Cells are incubated at 37° C. with a humidified atmosphere with 5% $CO_2$. Placental Stem Cells are optionally cryopreserved at this stage.

Subculturing and Expansion of Placental Stem Cells

Cryopreserved cells can be quickly thawed in a 37° C. water bath. Placental stem cells are immediately removed from the cryovial with 10 ml warm medium and transferred to a 15 ml sterile tube. The cells are centrifuged at 400 g for 10 minutes at room temperature. The cells are gently resuspended in 10 ml of warm culture medium by pipetting, and viable cell counts are determined by Trypan blue exclusion. Cells are then seeded at about 6000-7000 cells per cm$^2$ onto FN-coated flasks, prepared as above (approximately 5×10$^5$ cells per T-75 flask). The cells are incubated at 37° C., 5% $CO_2$ and 90% humidity. When the cells reached 75-85% confluency, all of the spent media is aseptically removed from the flasks and discarded. 3 ml of 0.25% trypsin/EDTA (w/v) solution is added to cover the cell layer, and the cells are incubated at 37° C., 5% $CO_2$ and 90% humidity for 5 minutes. The flask is tapped once or twice to expedite cell detachment. Once >95% of the cells are rounded and detached, 7 ml of warm culture medium is added to each T-75 flask, and the solution is dispersed by pipetting over the cell layer surface several times.

After counting the cells and determining viability as above, the cells are centrifuged at 1000 RPM for 5 minutes at room temperature. Cells are passaged by gently resuspending the cell pellet from one T-75 flask with culture medium, and evenly plating the cells onto two FN-coated T-75 flasks.

Using the above methods, populations of adherent placental stem cells are identified that express markers CD105, CD117, CD33, CD73, CD29, CD44, CD10, CD90 and CD133. This population of cells did not express CD34 or CD45. Some, but not all cultures of these placental stem cells express HLA-ABC and/or HLA-DR.

6.3 Example 3: Isolation of Placental Stem Cells from Placental Structures

6.3.1 Materials & Methods

6.3.1.1 Isolation of the Phenotype of Interest

Five distinct populations of placental cells were obtained from the placentas of normal, full-term pregnancies. All donors provided full written consent for the use of their placentas for research purposes. Five populations of cells were examined: placental cells from (1) placental perfusate (from perfusion of the placental vasculature); and enzymatic digestions of (2) amnion, (3) chorion, (4) amnion-chorion plate and (5) umbilical cord cells from enzymatic digestion. The various tissues were cleaned in sterile PBS (Gibco-Invitrogen Corporation, Carlsbad, Calif.) and placed on separate sterile Petri dishes. The various tissues were minced using a sterile surgical scalpel and placed into 50 mL Falcon Conical tubes. The minced tissues were digested with 1× Collagenase (Sigma-Aldrich, St. Louis, Mo.) for 20 minutes in a 37° C. water bath, centrifuged, and then digested with 0.25% Trypsin-EDTA (Gibco-Invitrogen Corp) for 10 minutes in a 37° C. water bath. The various tissues were centrifuged after digestion and rinsed once with sterile PBS (Gibco-Invitrogen Corp). The reconstituted cells were then filtered twice, once with 100 μm cell strainers and once with 30 μm separation filters, to remove any residual extracellular matrix or cellular debris.

6.3.1.2 Cellular Viability Assessment and Cell Counts

The manual trypan blue exclusion method was employed post digestion to calculate cell counts and assess cellular viability. Cells were mixed with Trypan Blue Dye (Sigma-Aldrich) at a ratio of 1:1, and the cells were read on hemacytometer.

6.3.1.3 Cell Surface Marker Characterization

Cells that were HLA ABC⁻/CD45⁻/CD34⁻/CD133⁺ were selected for characterization. Cells having this phenotype were identified, quantified, and characterized by two of Becton-Dickinson flow cytometers, the FACSCalibur and the FACS Aria (Becton-Dickinson, San Jose, Calif., USA). The various placental cells were stained, at a ratio of about 10 μL of antibody per 1 million cells, for 30 minutes at room temperature on a shaker. The following anti-human antibodies were used: Fluorescein Isothiocyanate (FITC) conjugated monoclonal antibodies against HLA-G (Serotec, Raleigh, N.C.), CD10 (BD Immunocytometry Systems, San Jose, Calif.), CD44 (BD Biosciences Pharmingen, San Jose, Calif.), and CD105 (R&D Systems Inc., Minneapolis, Minn.); Phycoerythrin (PE) conjugated monoclonal antibodies against CD44, CD200, CD117, and CD13 (BD Biosciences Pharmingen); Phycoerythrin-Cy5 (PE Cy5) conjugated Streptavidin and monoclonal antibodies against CD117 (BD Biosciences Pharmingen); Phycoerythrin-Cy7 (PE Cy7) conjugated monoclonal antibodies against CD33 and CD10 (BD Biosciences); Allophycocyanin (APC) conjugated streptavidin and monoclonal antibodies against CD38 (BD Biosciences Pharmingen); and Biotinylated CD90 (BD Biosciences Pharmingen). After incubation, the cells were rinsed once to remove unbound antibodies and were fixed overnight with 4% paraformaldehyde (USB, Cleveland, Ohio) at 4° C. The following day, the cells were rinsed twice, filtered through a 30 μm separation filter, and were run on the flow cytometer(s).

Samples that were stained with anti-mouse IgG antibodies (BD Biosciences Pharmingen) were used as negative controls and were used to adjust the Photo Multiplier Tubes (PMTs). Samples that were single stained with anti-human antibodies were used as positive controls and were used to adjust spectral overlaps/compensations.

6.3.1.4 Cell Sorting and Culture

One set of placental cells (from perfusate, amnion, or chorion) was stained with 7-Amino-Actinomycin D (7AAD; BD Biosciences Pharmingen) and monoclonal antibodies specific for the phenotype of interest. The cells were stained at a ratio of 10 μL of antibody per 1 million cells, and were incubated for 30 minutes at room temperature on a shaker. These cells were then positively sorted for live cells expressing the phenotype of interest on the BD FACS Aria and plated into culture. Sorted (population of interest) and "All" (non-sorted) placental cell populations were plated for comparisons. The cells were plated onto a fibronectin (Sigma-Aldrich) coated 96 well plate at the cell densities listed in Table 4 (cells/cm²). The cell density, and whether the cell type was plated in duplicate or triplicate, was determined and governed by the number of cells expressing the phenotype of interest.

TABLE 4

Cell plating densities
96 Well Plate Culture
Density of Plated Cells

| Conditions | Sorted | All | All Max. Density |
|---|---|---|---|
| Cell Source | | A | |
| Set #1: | 40.6 K/cm² | 40.6 K/cm² | 93.8 K/cm² |
| Set #2 | 40.6 K/cm² | 40.6 K/cm² | 93.8 K/cm² |
| Set #3: | 40.6 K/cm² | 40.6 K/cm² | 93.8 K/cm² |
| Cell Source | | B | |
| Set #1: | 6.3 K/cm² | 6.3 K/cm² | 62.5 K/cm² |
| Set #2 | 6.3 K/cm² | 6.3 K/cm² | 62.5 K/cm² |
| Cell Source | | C | |
| Set #1: | 6.3 K/cm² | 6.3 K/cm² | 62.5 K/cm² |
| Set #2 | 6.3 K/cm² | 6.3 K/cm² | 62.5 K/cm² |

Complete medium (60% DMEM-LG (Gibco) and 40% MCDB-201 (Sigma); 2% fetal calf serum (Hyclone Labs.); 1× insulin-transferrin-selenium (ITS); 1× linoleic acid-bovine serum albumin (LA-BSA); $10^{-9}$M dexamethasone (Sigma); $10^{-4}$ M ascorbic acid 2-phosphate (Sigma); epidermal growth factor 10 ng/mL (R&D Systems); and platelet-derived growth factor (PDGF-BB) 10 ng/mL (R&D Systems)) was added to each well of the 96 well plate and the plate was placed in a 5% $CO_2/37°$ C. incubator. On day 7, 100 μL of complete medium was added to each of the wells. The 96 well plate was monitored for about two weeks and a final assessment of the culture was completed on day 12.

6.3.1.5 Data Analysis

FACSCalibur data was analyzed in FlowJo (Tree star, Inc) using standard gating techniques. The BD FACS Aria data was analyzed using the FACSDiva software (Becton-Dickinson). The FACS Aria data was analyzed using doublet discrimination gating to minimize doublets, as well as, standard gating techniques. All results were compiled in Microsoft Excel and all values, herein, are represented as average±standard deviation (number, standard error of mean).

6.3.2 Results

6.3.2.1 Cellular Viability

Post-digestion viability was assessed using the manual trypan blue exclusion method (FIG. 1). The average viability of cells obtained from the majority of the digested tissue (from amnion, chorion or amnion-chorion plate) was around 70%. Cells from amnion had an average viability of 74.35%±10.31% (n=6, SEM=4.21), chorion had an average viability of 78.18%±12.65% (n=4, SEM=6.32), amnion-chorion plate had an average viability of 69.05%±10.80% (n=4, SEM=5.40), and umbilical cord had an average viability of 63.30%±20.13% (n=4, SEM=10.06). Cells from perfusion, which did not undergo digestion, retained the highest average viability, 89.98±6.39% (n=5, SEM=2.86).

6.3.2.2 Cell Quantification

The five distinct populations of placenta derived cells were analyzed to determine the numbers of HLA ABC$^-$/CD45$^-$/CD34$^-$/CD133$^+$ cells. From the analysis of the BD FACSCalibur data, it was observed that the amnion, perfusate, and chorion contained the greatest total number of these cells, 30.72±21.80 cells (n=4, SEM=10.90), 26.92±22.56 cells (n=3, SEM=13.02), and 18.39±6.44 cells (n=2, SEM=4.55) respectively (data not shown). The amnion-chorion plate and umbilical cord contained the least total number of cells expressing the phenotype of interest, 4.72±4.16 cells (n=3, SEM=2.40) and 3.94±2.58 cells (n=3, SEM=1.49) respectively (data not shown).

Similarly, when the percent of total cells expressing the phenotype of interest was analyzed, it was observed that amnion and placental perfusate contained the highest percentages of cells expressing this phenotype (0.0319%±0.0202% (n=4, SEM=0.0101) and 0.0269%±0.0226% (n=3, SEM=0.0130) respectively (FIG. 2). Although umbilical cord contained a small number of cells expressing the phenotype of interest (FIG. 2), it contained the third highest percentage of cells expressing the phenotype of interest, 0.020±0.0226% (n=3, SEM=0.0131) (FIG. 2). The chorion and amnion-chorion plate contained the lowest percentages of cells expressing the phenotype of interest, 0.0184±0.0064% (n=2, SEM=0.0046) and 0.0177±0.0173% (n=3, SEM=0.010) respectively (FIG. 2).

Consistent with the results of the BD FACSCalibur analysis, the BD FACS Aria data also identified amnion, perfusate, and chorion as providing higher numbers of HLA ABC$^-$/CD45$^-$/CD34$^-$/CD133$^+$ cells than the remaining sources. The average total number of cells expressing the phenotype of interest among amnion, perfusate, and chorion was 126.47±55.61 cells (n=15, SEM=14.36), 81.65±34.64 cells (n=20, SEM=7.75), and 51.47±32.41 cells (n=15, SEM=8.37), respectively (data not shown). The amnion-chorion plate and umbilical cord contained the least total number of cells expressing the phenotype of interest, 44.89±37.43 cells (n=9, SEM=12.48) and 11.00±4.03 cells (n=9, SEM=1.34) respectively (data not shown).

BD FACS Aria data revealed that the B and A cell sources contained the highest percentages of HLA ABC$^-$/CD45$^-$/CD34$^-$/CD133$^+$ cells, 0.1523±0.0227% (n=15, SEM=0.0059) and 0.0929±0.0419% (n=20, SEM=0.0094) respectively (FIG. 3). The D cell source contained the third highest percentage of cells expressing the phenotype of interest, 0.0632±0.0333% (n=9, SEM=0.0111) (FIG. 3). The C and E cell sources contained the lowest percentages of cells expressing the phenotype of interest, 0.0623±0.0249% (n=15, SEM=0.0064) and 0.0457±0.0055% (n=9, SEM=0.0018) respectively (FIG. 3).

After HLA ABC$^-$/CD45$^-$/CD34$^-$/CD133$^+$ cells were identified and quantified from each cell source, its cells were further analyzed and characterized for their expression of cell surface markers HLA-G, CD10, CD13, CD33, CD38, CD44, CD90, CD105, CD117, CD200, and CD105.

6.3.2.3 Placental Perfusate-Derived Cells

Perfusate-derived cells were consistently positive for HLA-G, CD33, CD117, CD10, CD44, CD200, CD90, CD38, CD105, and CD13 (FIG. 4). The average expression of each marker for perfusate-derived cells was the following: 37.15%±38.55% (n=4, SEM=19.28) of the cells expressed HLA-G; 36.37%±21.98% (n=7, SEM=8.31) of the cells expressed CD33; 39.39%±39.91% (n=4, SEM=19.96) of the cells expressed CD117; 54.97%±33.08% (n=4, SEM=16.54) of the cells expressed CD10; 36.79%±11.42% (n=4, SEM=5.71) of the cells expressed CD44; 41.83%±19.42% (n=3, SEM=11.21) of the cells expressed CD200; 74.25%±26.74% (n=3, SEM=15.44) of the cells expressed CD90; 35.10%±23.10% (n=3, SEM=13.34) of the cells expressed CD38; 22.87%±6.87% (n=3, SEM=3.97) of the cells expressed CD105; and 25.49%±9.84% (n=3, SEM=5.68) of the cells expressed CD13.

6.3.2.4 Amnion-Derived Cells

Amnion-derived cells were consistently positive for HLA-G, CD33, CD117, CD10, CD44, CD200, CD90, CD38, CD105, and CD13 (FIG. 5). The average expression of each marker for amnion-derived was the following: 57.27%±41.11% (n=3, SEM=23.73) of the cells expressed HLA-G; 16.23%±15.81% (n=6, SEM=6.46) of the cells expressed CD33; 62.32%±37.89% (n=3, SEM=21.87) of the cells expressed CD117; 9.71%±13.73% (n=3, SEM=7.92) of the cells expressed CD10; 27.03%±22.65% (n=3, SEM=13.08) of the cells expressed CD44; 6.42%±0.88% (n=2, SEM=0.62) of the cells expressed CD200; 57.61%±22.10% (n=2, SEM=15.63) of the cells expressed CD90; 63.76%±4.40% (n=2, SEM=3.11) of the cells expressed CD38; 20.27%±5.88% (n=2, SEM=4.16) of the cells expressed CD105; and 54.37%±13.29% (n=2, SEM=9.40) of the cells expressed CD13.

6.3.2.5 Chorion-Derived Cells

Chorion-derived cells were consistently positive for HLA-G, CD117, CD10, CD44, CD200, CD90, CD38, and CD13, while the expression of CD33, and CD105 varied (FIG. 6). The average expression of each marker for chorion cells was the following: 53.25%±32.87% (n=3, SEM=18.98) of the cells expressed HLA-G; 15.44%±11.17% (n=6, SEM=4.56) of the cells expressed CD33; 70.76%±11.87% (n=3, SEM=6.86) of the cells expressed CD117; 35.84%±25.96% (n=3, SEM=14.99) of the cells expressed CD10; 28.76%±6.09% (n=3, SEM=3.52) of the cells expressed CD44; 29.20%±9.47% (n=2, SEM=6.70) of the cells expressed CD200; 54.88%±0.17% (n=2, SEM=0.12) of the cells expressed CD90; 68.63%±44.37% (n=2, SEM=31.37) of the cells expressed CD38; 23.81%±33.67% (n=2, SEM=23.81) of the cells expressed CD105; and 53.16%±62.70% (n=2, SEM=44.34) of the cells expressed CD13.

6.3.2.6 Amnion-Chorion Plate Placental Cells

Cells from amnion-chorion plate were consistently positive for HLA-G, CD33, CD117, CD10, CD44, CD200, CD90, CD38, CD105, and CD13 (FIG. 7). The average expression of each marker for amnion-chorion plate-derived cells was the following: 78.52%±13.13% (n=2, SEM=9.29) of the cells expressed HLA-G; 38.33%±15.74% (n=5, SEM=7.04) of the cells expressed CD33; 69.56%±26.41% (n=2, SEM=18.67) of the cells expressed CD117; 42.44%±53.12% (n=2, SEM=37.56) of the cells expressed CD10; 32.47%±31.78% (n=2, SEM=22.47) of the cells expressed CD44; 5.56% (n=1) of the cells expressed CD200; 83.33% (n=1) of the cells expressed CD90; 83.52% (n=1) of the cells expressed CD38; 7.25% (n=1) of the cells expressed CD105; and 81.16% (n=1) of the cells expressed CD13.

6.3.2.7 Umbilical Cord-Derived Cells

Umbilical cord-derived cells were consistently positive for HLA-G, CD33, CD90, CD38, CD105, and CD13, while the expression of CD117, CD10, CD44, and CD200 varied (FIG. 8). The average expression of each marker for umbilical cord-derived cells was the following: 62.50%±53.03% (n=2, SEM=37.50) of the cells expressed HLA-G; 25.67%±11.28% (n=5, SEM=5.04) of the cells expressed CD33; 44.45%±62.85% (n=2, SEM=44.45) of the cells expressed CD117; 8.33%±11.79% (n=2, SEM=8.33) of the cells expressed CD10; 21.43%±30.30% (n=2, SEM=21.43) of the cells expressed CD44; 0.0% (n=1) of the cells expressed CD200; 81.25% (n=1) of the cells expressed CD90; 64.29% (n=1) of the cells expressed CD38; 6.25% (n=1) of the cells expressed CD105; and 50.0% (n=1) of the cells expressed CD13.

A summary of all marker expression averages is shown in FIG. 9.

6.3.2.8 BD FACS Aria Sort Report

The three distinct populations of placental cells that expressed the greatest percentages of HLA ABC, CD45, CD34, and CD133 (cells derived from perfusate, amnion and chorion) were stained with 7AAD and the antibodies for these markers. The three populations were positively sorted for live cells expressing the phenotype of interest. The results of the BD FACS Aria sort are listed in Table 5.

TABLE 5

BD FACS Aria Sort Report

| Cell Source | Events Processed | Events Sorted (Phenotype of Interest) | % Of Total |
|---|---|---|---|
| Perfusate | 135540110 | 51215 | 0.037786 |
| Amnion | 7385933 | 4019 | 0.054414 |
| Chorion | 108498122 | 4016 | 0.003701 |

The three distinct populations of positively sorted cells ("sorted") and their corresponding non-sorted cells were plated and the results of the culture were assessed on day 12. Sorted perfusate-derived cells, plated at a cell density of 40,600/cm$^2$, resulted in small, round, non-adherent cells. Two out of the three sets of non-sorted perfusate-derived cells, each plated at a cell density of 40,600/cm$^2$, resulted in mostly small, round, non-adherent cells with several adherent cells located around the periphery of well. Non-sorted perfusate-derived cells, plated at a cell density of 93,800/cm$^2$, resulted in mostly small, round, non-adherent cells with several adherent cells located around the well peripheries.

Sorted amnion-derived cells, plated at a cell density of 6,300/cm$^2$, resulted in small, round, non-adherent cells. Non-sorted amnion-derived cells, plated at a cell density of 6,300/cm$^2$, resulted in small, round, non-adherent cells. Non-sorted amnion-derived cells plated at a cell density of 62,500/cm$^2$ resulted in small, round, non-adherent cells.

Sorted chorion-derived cells, plated at a cell density of 6,300/cm$^2$, resulted in small, round, non-adherent cells. Non-sorted chorion-derived cells, plated at a cell density of 6,300/cm$^2$, resulted in small, round, non-adherent cells. Non-sorted chorion-derived cells plated at a cell density of 62,500/cm$^2$, resulted in small, round, non-adherent cells. These cells became adherent upon subsequent culture.

Subsequent to the performance of the experiments related above, and further culture of the placental stem cells, it was determined that the labeling of the antibodies for CD117 and CD133, in which a streptavidin-conjugated antibody was labeled with biotin-conjugated phycoerythrin (PE), produced background significant enough to resemble a positive reading. This background had initially resulted in the placental stem cells being deemed to be positive for both markers. When a different label, APC or PerCP was used, the background was reduced, and the placental stem cells were correctly determined to be negative for both CD117 and CD133.

6.4 Example 4: Differentiation of Placental Stem Cells

Adherent placental stem cells were differentiated into several different cell lineages. Adherent placental stem cells were isolated from the placenta by physical disruption of tissue from anatomical sites within the placenta, including the amniotic membrane, chorion, placental cotyledons, or any combination thereof, and umbilical cord stem cells were obtained by physical disruption of umbilical cord tissue.

Placental stem cells and umbilical cord stem cells were established in a medium containing low concentrations of fetal calf serum and limited growth factors. Flow cytometry analysis showed that placental stem cells typically exhibited a CD200+ CD105+ CD73+ CD34− CD45− phenotype at percentages of ≥70%. Placental stem cells were found to differentiate down the adipocyte, chondrocyte and osteocyte lineages.

In an induction medium containing IBMX, insulin, dexamethasone and indomethacin, placental stem cells turned into fat laden adipocytes in 3 to 5 weeks. Under osteogenic induction culture conditions, placental stem cells were found to form bone nodules and have calcium depositions in their extracellular matrix. Chondrogenic differentiation of placental stem cells was performed in micropellets and was confirmed by formation of glycosaminoglycan in the tissue aggregates.

6.5 Example 5: Immunomodulation Using Placental Stem Cells

Placental stem cells possess an immunomodulatory effect, including suppression of the proliferation of T cells and natural killer cells. The following experiments demonstrate that placental stem cells have the ability to modulate the response of T cells to stimulation in two assays, the mixed lymphocyte reaction assay and the regression assay.

6.5.1 Mixed Lymphocyte Reaction Assays

The MLR measures the reaction of an effector population against a target population. The effectors can be lymphocytes or purified subpopulations, such as CD8+ T cells or NK cells. The target population is either allogeneic irradiated PBMCs, or as in the present studies, mature DCs. The responder population consists of allo-specific cells, estimated at 20% of total T cells. The modified placental stem cell MLR uses placental stem cells in the reaction.

Placental stem cells were plated in 96 well plate wells, and the effector population was added. Placental stem cells and 5(6)-carboxyfluorescein diacetate N-succinimidyl ester (CFSE) stained effectors were preincubated for 24 hours before targets, mature DCs, were added. After six days, supernatants and non-adherent cells were harvested. Supernatants were analyzed by Luminex bead analysis, and the cells were analyzed by flow cytometry.

Classically, the MLR produces a proliferative response in both the CD8+ and the CD4+ T cell compartment. This response is a naïve T cell response, as two allogeneic donors have never encountered each other before. Both CD4+ T cells and CD8+ T cells proliferated vigorously in the standard MLR. When placental stem cells were added to the MLR, the CD4 and CD8 T cell proliferation, as measured by the percentage of CFSE$^{Low}$ responder cells, was dampened.

The effect of adding placental stem cells to an MLR (PMLR) can be seen in FIGS. 10A and 10B (PMLR trace) and FIG. 11. The results were similar whether only CD4+ or CD8+ T cells were used individually, or whether equal amounts of CD4+ T cells and CD8+ T cells were used together. Placental stem cells obtained from the amnion-chorion or umbilical cord stroma suppressed the MLR to similar extents, and no difference in suppression was seen between CD4+ T cells and CD8+ T cells. This was also true for the bulk T cell reactions.

A separate MLR was performed using CD4+ T cells, CD8+ T cells, or both CD4+ and CD8+ T cells, and allogeneic dendritic cells (DC). Placental stem cells were added to the MLR, and the degree of proliferation of the T cells was assessed, using an MLR without placental stem cells as a control.

CD4+ and CD8+ T cells, and CD14+ monocytes, were isolated from buffy coats using Miltenyi MACS columns and beads, used according to manufacturer instructions. Dendritic cells were obtained by a six-day culture of monocytes in RPMI 1640 supplemented with 1% donor plasma, IL-4, and GM-CSF, and a two-day culture in RPMI 1640 supplemented with IL-1β, TNF-α, and IL-6. Allogeneic T cells and DC in the ratio T:DC of 10:1 were incubated to produce a classic 6 day MLR. T cell proliferation was assessed by staining T cells with CFSE (Carboxy-fluorescein diacetate, succinimidyl ester) before being added to the assay. CSFE is used to assess the degree of proliferation by measurement of dilution of the stain among daughter cell populations.

To this assay, placental stem cells (PSCs) were added at the ratio T:DC:PSC of 10:1:2. The reaction was set up in a 96-well plate in a final volume of 200 µL RPMI 1640 supplemented with 5% pooled human serum (R5). After six days, non-adherent cells were briefly resuspended and transferred to a 5 mL tube washed with RPMI, and stained with CD4 and CD8 antibody. Proliferation of the CD4 and CD8 compartment was assessed on a BD FACS Calibur.

Placental stem cells. Placental stem cells were obtained as described in Examples 1 and 2, above. Placental stem cells were obtained from the following placental tissues: amnion (AM), or amnion/chorion (AC). Umbilical cord stem cells were obtained from digestion of umbilical cord (UC). Fibroblasts (FB) and bone marrow-derived mesenchymal stem cells (MSCs) were added as controls.

Results. When placental stem cells are added to the MLR, T cell proliferation is dampened (FIG. 12). Placental stem cells used in the experiments reflected in FIG. 10 were derived from one placenta, designated 61665. For all placental stem cells tested, when either CD4+ and CD8+ T cells but not both were used, the CD4+ compartment was suppressed to a greater degree than the CD8+ compartment (FIG. 12A). Suppression by AM and UC placental stem cells of CD4+ activation was roughly equivalent to suppression mediated by MSCs, with a suppression of about 60%-75%. When the MLR was run using both CD4+ and CD8+ T cells, placental stem cells suppressed proliferation in the CD4+ compartment to a far greater degree than the CD8+ compartment (FIG. 12B). In particular, CD4+ T cell proliferation suppression by AM placental stem cells approached 90%, exceeding the suppression shown by MSCs. The difference in suppression between these two compartments was most striking for AM and AC placental stem cells.

Placental stem cells from different donors suppress T cell proliferation in the MLR to a different degree (FIG. 13). Placental stem cells from a different placenta, designated 65450, suppressed CD4+ and CD8+ T cell proliferation in the MLR differently than placental stem cells from placenta 61665. Strikingly, AC and UC PSCs from placenta 65450 suppressed T cell proliferation from 80% to 95%, exceeding the suppression in this assay by MSCs. AC placental stem cells from placenta 65450, however, did not suppress T cell proliferation to an appreciable degree (compare AM placental stem cell suppression in FIG. 10A).

Placental stem cells also suppressed the activity of Natural Killer (NK) cells in the MLR.

6.5.2 Regression Assay

Placental stem cells were shown in a regression assay to suppress a T cell response to a B cell line expressing Epstein-Barr virus (EBV) antigens. The regression assay is a recall assay that measures effector T cell mechanisms brought about by presentation of EBV antigen peptides on MHC Class I and II of EBV-transformed B cells. The assay is performed by mixing T cells with an artificially created transformed B cell line, the lymphoblastoid cell line (LCL) from the same donor. The LCL expresses nine Epstein-Barr virus antigens that elicit between them a range of adaptive T and B cell responses, although in the classic regression assay, only T cell effector mechanisms are measured. The regression assay offers a convenient way of measuring cytotoxicity to targets infected with a naturally occurring pathogen, in that the LCL expresses the activated B cell marker CD23. Therefore, the cell count of CD23-expressing cells is a measure of the number of LCL surviving in the assay.

The classic seventeen day regression assay gave results similar to those seen in the first cluster of bars in FIG. 14. No CD23$^+$ cells were detected, as they had all been killed by CD4$^+$ and CD8$^+$ T cells. With the addition of placental stem cells, seen in the next two clusters of bars, survival of CD23$^+$ cells was enhanced. Without wishing to be bound by theory, two explanations can be given for the observed effect. Either the T cells had died, and left behind the LCL to expand freely, or placental stem cells mainly increased the longevity of the LCL, having had less of an effect on the T cells.

In a separate regression assay, T cells and dendritic cells were obtained from laboratory donors. Epstein-Barr virus-transformed B cells lines, LCLs, were obtained by incubating peripheral blood mononuclear cells (PBMCs) with supernatant from a lytic EBV line, B95.8, and cyclosporin A for two weeks. The LCL expressed 9 EBV antigens. The outgrowing LCL line is maintained in RPMI 1640 supplemented with 10% fetal calf serum. The regression assay was performed by mixing CD4$^+$ or CD8$^+$ T cells with autologous LCL at a ratio T:LCL of 10:1. The assay was performed in a 96-well plate in 200 µL RPMI 1640 supplemented with 5% pooled human serum (R5). To this assay, placental stem cells are added in a ratio T:LCL:PSC of 10:1:2. The assay was run for 6, 10, or 17 days.

A six-day regression assay was performed using CSFE-labeled T cells. Placental stem cells from placenta 65450 suppressed T cell proliferation in the regression assay by about 65% to about 97%, a result that corresponds to the results for these PSCs in the MLR (FIG. 15). Again, UC and AC lines from placenta 65450 significantly suppressed T cell proliferation, while 65450 AM PSCs did not suppress proliferation.

In a separate experiment, it was determined that natural killer cells were suppressed in the MLR and regression assays, as well. NK cells, when the MLR or regression assay was run including 50 U/ml IL-2, the suppressive effect was about 45% (range about 40% to about 65%, SEM 5%).

Placental stem cells are not immunogenic. In no instance was more than 5% background T cell proliferation observed against placental stem cells from any donor or any placental anatomical site.

Requirement for cell-to-cell contact. The cytotoxic effect in the regression assay, and allo-recognition in the MLR, both depend on TCR (T cell receptor):MHC interactions between target and effector cells. The requirements for cell-to-cell contact in placental stem cell-mediated suppression was assessed using a transwell assay. In the assay, an MLR was conducted in which the T cells and placental stem cells were separated by a membrane. As seen in FIG. 16, the higher the number of placental stem cells used in the MLR, the higher the reduction of suppression, indicating that, particularly at higher densities, placental stem cells (UC) require significant contact with the T cells to suppress T cell proliferation.

A separate assay confirmed that immunosuppression of T cells by placental stem cells appears to at least partially involve a soluble factor. To determine whether the placental stem cells mediated immunosuppression is dependent on cell to cell contact, transwell assays were performed in which placental stem cells were placed in an insert at the bottom of which a membrane allowed passage only of soluble factors. At the floor of the well, separated from the placental stem cells, were the MLR or T cells alone. In order to determine if an observed effect depended on the relative dose of placental stem cells, the stem cells were added at different relative densities to T cells and DCs. When umbilical cord placental stem cells were separated from the MLR, the suppressive effect was partly abrogated. When placental stem cells were used at densities similar to that used in FIG. 11, the MLR suppression was abrogated 75% for CD4$^+$ T cells, and 85% for CD8$^+$ T cells (FIG. 17, FIG. 18). The suppressive effect was still at 66% when just a quarter dose of placental stem cells were used (UC OP 25), and dropped to background levels when 12,500 UC placental stem cells were added. No change in suppression with separation using an insert was observed (FIG. 17). At 25,000 placental stem cells, despite the still vigorous suppressive effect, the smallest relative drop in suppression on introduction of the insert was observed (FIG. 18).

6.6 Example 6: Contact Dependence of Placental Stem Cell Immunosuppression Differs from that of Bone Marrow-Derived Mesenchymal Stem Cells In an experiment to determine the degree of contact dependency in immunomodulation, umbilical cord stem cells showed a markedly different requirement for cell-to-cell contact for immunomodulation than that of bone marrow derived stem cells. In particular, placental stem cells depended more upon cell-to-cell contact to effect immunomodulation, particularly at higher numbers of placental or mesenchymal stem cells.

Bone marrow-derived stem cells (BMSCs) and umbilical cord stem cells (UC) have different requirements for cell-to-cell contact, depending on the ratio of adherent cells to T cells in a mixed leukocyte reaction assay (MLR). In a transwell experiment, in which placental stem cells were separated from T cells and dendritic cells (DCs) in the MLR, the suppression varied between the two types of adherent cell. FIG. 19 displays results from the open well and transwell side by side. When approximately 100,000 or 75,000 UC or BMSCs were used in the open well format, a similar suppression was observed. However, in the transwell format, UCs suppress the MLR to a lesser degree than do BMSCs, indicating a larger contact dependency at these higher placental stem cell/T cell ratios. When lower placental cell to T cell ratios were used, placental stem cells were more suppressive cell for cell.

From the suppression data, the degree of contact dependency was calculated. FIG. 20 shows the contact dependency of the UC and BMSC MLRs. Bone marrow-derived cells are less contact dependent at higher BM/T cell ratios than are UCs. In other words, UC placental stem cells and BMSCs behave differently with respect to an important mechanistic parameter, the need for cell-to-cell contact.

Regulatory T cells (Tregs) are necessary for BMSC-mediated T cell suppression. See Aggarwal & Pittenger, "Human Mesenchymal Stem Cells Modulate Allogeneic Immune Cell Responses," *Blood* 105(4):1815-1822 (2004). CD4+ CD25+ Tregs were depleted from healthy donor peripheral blood mononuclear cells (PBMCs), and a regression assay was performed using autologous EBV (Epstein-Barr virus)-transformed cells. UCs were added to some conditions. As can be seen in FIG. 21, there is no difference in placental stem cell-mediated suppression of the T cell response in the regression assay whether or not Tregs are present. Thus, while T regulatory T cells are reportedly necessary for BMSC-mediated T cell suppression, T regulatory cells do not appear to play a role in placental stem cell-mediated immune suppression.

An MLR was performed in which the T cells were taken from an MLR suppressed by placental stem cells, and the dendritic cells were added fresh. The T cells were stained with CFSE, which is distributed equally into daughter cells during proliferation. CFSE$^{Hi}$ cells are T cells that have not proliferated (e.g., the left-most peaks in the panels in FIG. 21). This population was obtained by sorting stained T cells on a FACS Aria. These cells were used in a second MLR with fresh dendritic cells. As can be seen in FIG. 22, no lasting suppression was observed, as the formerly suppressed cells proliferated well against the DCs. It is unlikely that the CFSE$^{Lo}$ cells (that is, daughter cells) would have been responsible for the suppression, as these cells themselves proliferated subsequently. The CFSE$^{Hi}$ population is made up of non-allo-specific cells that would not have proliferated against this DC donor, as well as T cells suppressed by placental stem cells. Once the placental stem cells were removed, the suppressed cells proliferated.

An MLR is suppressed by BMSCs when approximately 10% of the supernatant is replaced by the supernatant from a BMSC MLR. In sharp contrast, no change in T cell proliferation was observed when supernatant was replaced by supernatant from an MLR comprising placental stem cells, even when 75% of the medium was replaced (FIG. 23).

It is possible that DCs or resting T cells are affected by incubation with placental stem cells for different amounts of time before starting the MLR. This was tested by incubating placental stem cells or BMSCs with T cells (FIG. 24A) or DCs (FIG. 24B) for varying lengths of time before starting the assay. Preincubating T cells and placental stem cells does not alter the suppressive phenotype appreciably (FIG. 20A). However, BMSC T cell suppression changes depending of the length of DC/placental stem cell preincubation. As shown in FIG. 20B, suppression by BMSCs is strongest when DCs are added one day after the T cells. A much lower suppression appears, however, when DCs are added at the same time as T cells. Incubating DCs longer with BMSCs can reverse this loss of suppression. At two days preincubation, the suppression approaches the scenario where DCs are added a day after T cells (+1 day). No similar tendency is observed with placental stem cell-mediated suppression.

6.7 Example 7: Cytokine Profile of Placental Stem Cells and Umbilical Cord Stem Cells in the MLR and Regression Assay Umbilical cord stem cells (UC) and placental stem cells from amnion chorion plate (AC) were determined to secrete certain cytokines into the MLR medium.

In some assays, a cytokine array was used to measure the levels of cytokines and chemokines in the supernatants. Several factors were found to be secreted into supernatants, the most relevant to the MLR and regression assays being macrophage inflammatory protein (MIP)-1α and MIP-1β. Both of these chemoattractants attract T cells, and are secreted by CD8+ T cells in response to human immunodeficiency virus (HIV) infection. When assayed in the MLR, these chemoattractants' secretion correlated inversely with placental stem cell and MSC suppression of the MLR (FIG. 25). Neither placental stem cells nor MSCs secreted MIP-1α and MIP-1β.

In another study, a correlation was found in secretion of MCP-1 and IL-6, both of which are important immunoregulators (FIG. 26 and FIG. 27; compare with FIG. 11). While placental stem cells alone secreted no IL-6 or MCP-1, the UC and AC lines, both of which suppress the MLR and T cell proliferation in the regression assay (FIG. 11), secrete MCP-1 and IL-6 (FIG. 26 and FIG. 27). Although IL-6 is mostly associated with pro-inflammatory actions (see, e.g., Kishimoto et al., *Annu. Rev. Immunol.* 23:1-21 (2005)), it also has other functions, such as a protective role during liver damage in mice (see, e.g., Klein et al., *J. Clin. Invest* 115:860-869 (2005)).

In a separate study, AC used in an MLR or regression assay were analyzed for cytokine secretion. Cytokines were measured on a Luminex system in supernatants from 6-day stem cell cultures, stem cell MLRs or stem cell regression assays. MLRs included the stem cells, dendritic cells (DC), and T cells in a ratio of 2/1/10. Epstein-Barr virus (EBV) regression assays included stem cells, EBV tumor cells (Ts), and T cells at TS:stem cell:T ratio of 2:1:10.

Levels of IL-6 (11 ng/ml) and IL-8 (16 ng/ml) were found to stay constant in stem cell solo cultures, MLRs, and regression assays. The concentration of MCP-1 was determined to be about 2 ng/ml in stem cell solo cultures and non-suppressive control adherent cell MLRs and regression assays, but increased to about 10 ng/ml in suppressed stem cell MLRs and stem cell regression assays. These values fall within serum levels recorded for MCP-1.

Interleukin-2 (IL-2) is both a T cell survival factor and an obligate factor for CD4+ CD25+ T regulatory cells. This T cell subset is not required for T cell suppression by the AC stem cells, but IL-2 levels consistently decrease during MLR suppression by AC stem cells. MLR supernatants in the absence of AC stem cells contained about 35 pg/ml IL-2, whereas the MLRs that included AC stem cells contained up to 440 pg/ml IL-2.

The IL-2 concentrations correlated with suppression. For example, a CD4+ T cell MLR showing 85% suppression contained 330 pg/ml IL-2, and a CD8+ T cell MLR showing 85% suppression, using AC stem cells contained 66 pg/ml IL-2. These results indicate that IL-2 and MCP-1, traditionally known as stimulators of the immune response, may play a role in immune suppression.

6.8 Example 8: Production of Cryopreserved Stem Cell Product and Stem Cell Bank This Example demonstrates the isolation of placental stem cell and the production of a frozen stem cell-based product.

Summary: Placental tissue is dissected and digested, followed by primary and expansion cultures to achieve an expanded cell product that produces many cell doses. Cells are stored in a two-tiered cell bank and are distributed as a frozen cell product. All cell doses derived from a single donor placenta are defined as a lot, and one placenta lot is processed at a time using sterile technique in a dedicated room and Class 100 laminar flow hood. The cell product is defined as being CD105+, CD200+, CD10+, and CD34−, having a normal karyotype and no or substantially no maternal cell content.

6.8.1 Obtaining Stem Cells

Tissue Dissection and Digestion: A placenta is obtained less than 24 hours after expulsion. Placental tissue is obtained from amnion, a combination of amnion and chorion, or chorion. The tissue is minced into small pieces, about 1 mm in size. Minced tissue is digested in 1 mg/ml Collagenase 1A for 1 hour at 37° C. followed by Trypsin-EDTA for 30 minutes at 37° C. After three washes in 5% FBS in PBS, the tissue is resuspended in culture medium.

In another embodiment, a placenta is obtained les than 24 hours after expulsion. After cleaning the placenta, a hemostat is clamped to the distal end of the umbilical cord. The umbilical cord is cut at the junction with the placenta and transferred to a sterile dish. After cutting the cord below the hemostat, the cord is massaged to remove blood clots, and transferred to 500 ml PBS containing gentamicin and amphotericin B. 5 g of this cord is used. A scalpel is used to trim the remaining placental material by cutting in a radius of about 3 inches from the umbilical cord attachment point. Blood clots are forced from the remaining material, and 5 g of the amnion-chorion, centered at the umbilical cord root, is transferred to the same container as the umbilical cord. The umbilical cord and amnion-chorion tissue is sliced, then minced to pieces about 1 mm$^3$ in size. The tissue is then digested with 1 mg/ml Collagenase 1A (20 ml/g tissue) for 1 hour at 37° C. followed by Trypsin-EDTA (10 ml/g tissue) for 30 minutes at 37° C. After three washes in 5% FBS in PBS, the tissue is resuspended in culture medium (20 ml/g tissue) and transferred to T flasks at about 0.22 ml/cm$^2$.

Primary Culture: The purpose of primary culture is to establish cells from digested placental tissue. The digested tissue is suspended in culture medium and placed into Corning T-flasks, which are incubated in a humidified chamber maintained at 37° C. with 5% CO$_2$. Half of the medium is replenished after 5 days of culture. High-density colonies of cells form by 2 weeks of culture. Colonies are harvested with Trypsin-EDTA, which is then quenched with 2% FBS in PBS. Cells are centrifuged and resuspended in culture medium for seeding expansion cultures. These cells are defined as Passage 0 cells having doubled 0 times.

Expansion Culture: Cells harvested from primary culture, harvested from expansion culture, or thawed from the cell bank are used to seed expansion cultures. Cell Factories (NUNC™) are treated with 5% CO$_2$ in air at 50 ml/min/tray for 10 min through a sterile filter and warmed in a humidified incubator maintained at 37° C. with 5% CO$_2$. Cell seeds are counted on a hemacytometer with trypan blue, and cell number, viability, passage number, and the cumulative number of doublings are recorded. Cells are suspended in culture medium to about 2.3×10$^4$ cells/ml and 110 ml/tray are seeded in the Cell Factories. After 3-4 days and again at 5-6 days of culture, culture medium is removed and replaced with fresh medium, followed by another treatment with 5% CO$_2$ in air. When cells reach approximately 10$^5$ cells/cm$^2$, cells are harvested with Trypsin-EDTA, followed by quenching with 2% FBS in PBS. Cell are then centrifuged and resuspended in culture medium.

Cryopreservation: Cells to be frozen down are harvested from culture with Trypsin-EDTA (e.g., 0.044 ml/cm$^2$ for 5 minutes), quenched with 2% FBS in PBS, and counted on a hemacytometer. After centrifugation (e.g., at 300×g), cells are resuspended with 10% DMSO in FBS to a concentration of about 1 million cells/ml for cells to be used for assembly of a cell bank, and 10 million cells/ml for individual frozen cell doses. In another embodiment, the cells are diluted to about 2 million calls/ml in 10% HAS, 10% DMSO in Plasmalyte. The cell solution is transferred to a freezing container, which is placed in an isopropyl alcohol bath in a −80° C. freezer. The following day, cells are transferred to liquid nitrogen.

6.8.2 Design of a Stem Cell Bank

A "lot" is defined as all cell doses derived from a single donor placenta. Cells maintained normal growth, karyotype, and cell surface maker phenotype for over 8 passages and 30 doublings during expansion culture. Given this limitation, doses comprise cells from 5 passages and about 20 doublings. To generate a supply of equivalent cells, a single lot is expanded in culture and is stored in a two-tiered cell bank and frozen doses. In particular, cells harvested from the primary culture, which are defined as Passage 0 cells having undergone 0 doublings, are used to initiate an expansion culture. After the first passage, approximately 4 doublings occur, and cells are frozen in a Master Cell Bank (MCB). Vials from the MCB are used to seed additional expansion cultures. After two additional passages of cells thawed from the MCB, cells are frozen down in a Working Cell Bank (WCB), approximately 12 cumulative doublings. Vials from the WCB are used to seed an expansion culture for another 2 passages, resulting in Passage 5 cells at approximately 20 doublings that are frozen down into individual doses.

6.8.3 Thawing Cells for Culture

Frozen containers of cells are placed into a sealed plastic bag and immersed in a 37° C. water bath. Containers are gently swirled until all of the contents are melted except for a small piece of ice. Containers are removed from the sealed plastic bag and a 10× volume of culture medium is slowly added to the cells with gentle mixing. A sample is counted on the hemacytometer and seeded into expansion cultures.

6.8.4 Thawing Cells for Injection

Frozen containers of cells are transferred to the administration site in a dry nitrogen shipper. Prior to administration, containers are placed into a sealed plastic bag and immersed in a 37° C. water bath. Containers are gently swirled until all of the contents are melted except for a small piece of ice. Containers are removed from the sealed plastic bag and an equal volume of 2.5% HSA/5% Dextran is added. Cells are injected with no further washing.

6.8.5 Testing and Specifications

A maternal blood sample accompanies all donor placentas. The sample is screened for Hepatitis B core antibody and surface antigen, Hepatitis C Virus antibody and nucleic acid, and HIV I and II antibody and nucleic acid. Placental processing and primary culture begins prior to the receipt of test results, but continues only for placentas associated with maternal blood samples testing negative for all viruses. A lot is rejected if the donor tests positive for any pathogen. In addition, the tests described in Table 6 are performed on the MCB, the WCB, and a sample of the cell dose material derived from a vial of the WCB. A lot is released only when all specifications are met.

TABLE 6

Cell testing and specifications

| Test | Methods | Required Result |
|---|---|---|
| Sterility | BD BACTEC PEDS PLUS/F and BACTEC Myco/F Lytic | Negative |
| Endotoxin | LAL gel clot | ≤5 EU/ml* |
| Viability | Trypan Blue | >70% viable |
| Mycoplasma | Direct culture, DNA-fluorochrome (FDA PTC 1993) | Negative |
| Identity | Flow cytometry (see below) | CD105+, CD200+, CD10+, CD34− |
| Cell Purity | Microsatellite | No contaminating cell detected |
| Karyotype | G-banding and chromosome count on metaphase cells | Normal |

*For the product designed to be 40 ml of frozen cells/dose and a maximum of 5 EU/ml, the cell product is below the upper limit of 5 EU/kg/dose for recipients over 40 kg in body weight.

6.8.6 Surface Marker Phenotype Analysis

Cells are placed in 1% paraformaldehyde (PFA) in PBS for 20 minutes and stored in a refrigerator until stained (up to a week). Cells are washed with 2% FBS, 0.05% sodium azide in PBS (Staining Buffer) and then resuspended in staining buffer. Cells are stained with the following antibody conjugates: CD105-FITC, CD200-PE, CD34-PECy7, CD10-APC. Cells are also stained with isotype controls. After 30 minute incubation, the cells are washed and resuspended with Staining Buffer, followed by analysis on a flow cytometer. Cells having an increased fluorescence compared to isotype controls are counted as positive for a marker.

6.9 Treatment of Immune-Related Diseases Using Placental Stem Cells or Umbilical Cord Stem Cells This Example provides example treatment regimens for immune-related diseases or conditions.

6.9.1 Treatment of Crohn's Disease

An individual presents with ileocolitis, a form of Crohn's disease, and is experiencing abdominal pain, bloody diarrhea, and fever. The individual is administered $1-5 \times 10^8$ CD10+ CD34− CD105+ CD200+ placental stem cells and/or umbilical cord stem cells in 0.9% NaCl solution intravenously. The individual is monitored over the subsequent two weeks to assess reduction in one or more of the symptoms. The individual is monitored over the course of the next year, and placental stem cells in the same dose are administered as needed.

6.9.2 Treatment of Graft-Versus-Host Disease

An individual awaiting an allogeneic bone marrow transplant is administered $5-10 \times 10^8$ CD10+ CD34− CD105+ CD200+ placental stem cells and/or umbilical cord stem cells in 0.9% NaCl solution intravenously within 24 hours prior to bone marrow transplantation. Administration of the stem cells is repeated within 24 hours after bone marrow transplantation. The individual is monitored over the next 100 days, and is administered a follow-up dose of $5-10 \times 10^8$ CD10+ CD34− CD105+ CD200+ placental stem cells and/or umbilical cord stem cells is GVHD develops and progresses beyond Grade I.

6.9.3 Treatment of Rheumatoid Arthritis

An individual presents with rheumatoid arthritis in three or more joints. The individual is administered a combination of placental or umbilical cord stem cells and placental stem cells that have been modified to produce a fusion polypeptide comprising IL-1Ra and DHFR, wherein the two types of stem cells are administered in a 1:1 ratio. The engineered and non-engineered cells are $1-5 \times 10^8$ CD10+ CD34− CD105+ CD200+ placental stem cells and/or umbilical cord stem cells in 0.9% NaCl solution. The individual is given methotrexate at a standard dosage and monitored for reduction in joint inflammation.

EQUIVALENTS

The compositions and methods disclosed herein are not to be limited in scope by the specific embodiments described herein. Indeed, various modifications of the compositions and methods in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed:

1. A method of treating an individual having or at risk of developing a disease, disorder or condition associated with or caused by an inappropriate or unwanted immune response, comprising administering to the individual a therapeutically effective amount of placental stem cells, or culture medium conditioned by placental stem cells, wherein the therapeutically effective amount is an amount sufficient to cause a detectable improvement in one or more symptoms of said disease, disorder or condition, wherein said disease, disorder or condition is scleroderma, and wherein said placental stem cell is a CD10+, CD34−, CD105+, CD200+ placental stem cell.

2. The method of claim 1, wherein said placental stem cells express CD200 and HLA-G, or express CD73, CD105, and CD200, or express CD200 and OCT-4, or express CD73, CD105 and HLA-G, or express CD73 and CD105 and facilitate the formation of one or more embryoid-like bodies in a population of placental cells comprising said stem cell when said population is cultured under conditions that allow for the formation of an embryoid-like body, or express OCT-4 and facilitate the formation of one or more embryoid-like bodies in a population of placental cells comprising said stem cell when said population is cultured under conditions that allow for the formation of an embryoid-like body.

3. The method of claim 1, comprising administering a second therapeutic agent to said individual.

4. The method of claim 3, wherein said second therapeutic agent is an anti-inflammatory drug, a proton pump inhibitor, an immunosuppressant compound, or a vasodilator.

5. The method of claim 3, wherein said second therapeutic agent is an anti-inflammatory drug, an immunosuppressant compound, exposure to sunlight, exposure to ultraviolet light, a topical steroid, local superficial radiotherapy, total skin electron beam radiation, application of organic honey to skin affected by erythroderma, an interferon, a retinoid, a rexinoid, or vorinostat.

\* \* \* \* \*